United States Patent
Seelig et al.

(10) Patent No.: US 12,163,189 B2
(45) Date of Patent: *Dec. 10, 2024

(54) METHOD FOR PREPARATION AND HIGH-THROUGHPUT MICROBIAL SINGLE-CELL RNA SEQUENCING OF BACTERIA

(71) Applicant: UNIVERSITY OF WASHINGTON, Seattle, WA (US)

(72) Inventors: Georg Seelig, Seattle, WA (US); Anna Kuchina, Seattle, WA (US); Leandra Brettner, Seattle, WA (US); William DePaolo, Seattle, WA (US)

(73) Assignee: University of Washington, Seattle, WA (US)

( * ) Notice: Subject to any disclaimer, the term of this patent is extended or adjusted under 35 U.S.C. 154(b) by 405 days.

This patent is subject to a terminal disclaimer.

(21) Appl. No.: 16/949,949

(22) Filed: Nov. 20, 2020

(65) Prior Publication Data
US 2022/0162691 A1    May 26, 2022

Related U.S. Application Data

(60) Provisional application No. 62/941,101, filed on Nov. 27, 2019.

(51) Int. Cl.
 *C12Q 1/6874* (2018.01)
(52) U.S. Cl.
 CPC .................... *C12Q 1/6874* (2013.01)
(58) Field of Classification Search
 None
 See application file for complete search history.

(56) References Cited

U.S. PATENT DOCUMENTS

| 8,673,562 | B2 | 3/2014 | Drmanac |
| 8,771,957 | B2 | 7/2014 | Drmanac |
| 8,835,358 | B2 | 9/2014 | Fodor et al. |
| 8,871,686 | B2 | 10/2014 | Ghadessy et al. |

(Continued)

FOREIGN PATENT DOCUMENTS

| CA | 3064205 A1 | 11/2018 |
| CN | 10797089 A | 2/2020 |

(Continued)

OTHER PUBLICATIONS

Kuchina et al., "Microbial single-cell RNA sequencing by split-pool barcoding," bioRxiv preprint doi: https://doi.org/10.1101/869248, with 32 pages of Supplementary Materials; posted online Dec. 11, 2019. (Year: 2019).*

(Continued)

*Primary Examiner* — Kaijiang Zhang
(74) *Attorney, Agent, or Firm* — Christensen O'Connor Johnson Kindness PLLC

(57) ABSTRACT

Methods and kits for uniquely labeling nucleic acid molecules within a plurality of microbial cells are described. In an embodiment, the method comprises fixing and permeabilizing the plurality of microbial cells; dissociating microbial cell aggregates within a suspension comprising the plurality of microbial cells; reverse transcribing mRNA within the plurality of microbial cells to provide cDNA; and combinatorially labelling the cDNA to provide labelled cDNA.

17 Claims, 21 Drawing Sheets

Specification includes a Sequence Listing.

(56) References Cited

U.S. PATENT DOCUMENTS

| | | |
|---|---|---|
| 9,074,204 B2 | 7/2015 | Anderson et al. |
| 9,290,808 B2 | 3/2016 | Fodor et al. |
| 9,315,857 B2 | 4/2016 | Fu et al. |
| 9,506,918 B2 | 11/2016 | Fischer et al. |
| 9,637,784 B2 | 5/2017 | Drmanac |
| 9,708,659 B2 | 7/2017 | Fodor et al. |
| 9,727,810 B2 | 8/2017 | Fodor et al. |
| 9,816,137 B2 | 11/2017 | Fodor et al. |
| 9,845,502 B2 | 12/2017 | Fodor et al. |
| 10,002,316 B2 | 6/2018 | Fodor et al. |
| 10,144,950 B2 | 12/2018 | Nolan |
| 10,155,981 B2 | 12/2018 | Brenner et al. |
| 10,240,197 B1 | 3/2019 | Brenner et al. |
| 10,280,459 B1 | 5/2019 | Brenner et al. |
| 10,626,442 B2 | 4/2020 | Nolan |
| 10,697,013 B1 | 6/2020 | Brenner et al. |
| 10,900,065 B2 | 1/2021 | Seelig et al. |
| 10,982,256 B2 | 4/2021 | Nolan |
| 10,982,271 B2 | 4/2021 | Bava et al. |
| 10,995,362 B2 | 5/2021 | Dallett et al. |
| 11,168,355 B2 | 11/2021 | Seelig et al. |
| 11,214,794 B2 | 1/2022 | Nolan |
| 11,427,856 B2 | 8/2022 | Seelig et al. |
| 11,512,341 B1 | 11/2022 | Nolan |
| 11,555,216 B2 | 1/2023 | Seelig et al. |
| 11,560,585 B2 | 1/2023 | Nolan |
| 11,566,278 B2 | 1/2023 | Nolan |
| 11,634,751 B2 | 4/2023 | Seelig et al. |
| 11,634,752 B2 | 4/2023 | Nolan |
| 11,639,519 B1 | 5/2023 | Seelig et al. |
| 11,667,956 B2 | 6/2023 | Nolan |
| 11,680,283 B2 | 6/2023 | Seelig et al. |
| 11,692,214 B2 | 7/2023 | Nolan |
| 11,708,599 B2 | 7/2023 | Nolan |
| 11,732,290 B2 | 8/2023 | Nolan |
| 11,781,171 B1 | 10/2023 | Nolan |
| 2012/0220494 A1 | 8/2012 | Samuels et al. |
| 2013/0203605 A1 | 8/2013 | Shendure et al. |
| 2013/0274117 A1 | 10/2013 | Church et al. |
| 2014/0099637 A1 | 4/2014 | Nolan et al. |
| 2014/0256597 A1 | 9/2014 | He |
| 2014/0309118 A1 | 10/2014 | Bang et al. |
| 2014/0309119 A1 | 10/2014 | Jacobsen et al. |
| 2015/0298091 A1 | 10/2015 | Weitz et al. |
| 2015/0299784 A1 | 10/2015 | Fan et al. |
| 2015/0329852 A1 | 11/2015 | Nolan |
| 2015/0376609 A1 | 12/2015 | Hindson et al. |
| 2016/0024572 A1 | 1/2016 | Shishkin et al. |
| 2016/0115471 A1 | 4/2016 | Kim et al. |
| 2016/0122753 A1 | 5/2016 | Mikkelsen et al. |
| 2016/0138086 A1 | 5/2016 | Seelig et al. |
| 2016/0194699 A1 | 7/2016 | Borodina et al. |
| 2016/0251697 A1 | 9/2016 | Nolan |
| 2016/0378916 A1 | 12/2016 | Drmanac et al. |
| 2017/0009274 A1 | 1/2017 | Abate et al. |
| 2017/0233722 A1 | 8/2017 | Seelig |
| 2017/0321251 A1 | 11/2017 | Nolan |
| 2017/0362642 A1 | 12/2017 | Nolan et al. |
| 2018/0135042 A1 | 5/2018 | Rokhsar |
| 2018/0320241 A1 | 11/2018 | Nolan |
| 2020/0157603 A1 | 5/2020 | O'Huallachain et al. |
| 2020/0208197 A1 | 7/2020 | Nolan |
| 2021/0002733 A1 | 1/2021 | Nolan |
| 2021/0040538 A1 | 2/2021 | Nolan |
| 2022/0049286 A1 | 2/2022 | Dallett et al. |
| 2022/0056515 A1 | 2/2022 | Bava et al. |
| 2023/0049314 A1 | 2/2023 | Nolan |
| 2023/0081326 A1 | 3/2023 | Nolan |
| 2023/0167484 A1 | 6/2023 | Nolan |
| 2023/0193351 A1 | 6/2023 | Seelig et al. |
| 2023/0227891 A1 | 7/2023 | Seelig et al. |
| 2023/0265487 A1 | 8/2023 | Seelig et al. |
| 2023/0295688 A1 | 9/2023 | Seelig et al. |
| 2023/0304073 A1 | 9/2023 | Seelig et al. |
| 2023/0340567 A1 | 10/2023 | Seelig et al. |

FOREIGN PATENT DOCUMENTS

| | | |
|---|---|---|
| CN | 110910950 A | 3/2020 |
| EP | 3234602 B1 | 10/2017 |
| KR | 20200002705 A | 1/2020 |
| WO | 2012/045150 A1 | 4/2012 |
| WO | 2012/106385 A2 | 8/2012 |
| WO | 2012129363 A2 | 9/2012 |
| WO | 2014026032 A2 | 2/2014 |
| WO | 2014/137193 A1 | 9/2014 |
| WO | 2014/182528 A2 | 11/2014 |
| WO | 2016/100976 A2 | 6/2016 |
| WO | 2017044893 A1 | 3/2017 |
| WO | 2018/067792 A1 | 4/2018 |
| WO | 2019/173638 A1 | 9/2019 |
| WO | 2019/236599 A2 | 12/2019 |
| WO | 2020/089218 A1 | 5/2020 |

OTHER PUBLICATIONS

Crespi, B.J., "The evolution of social behavior in microorganisms," Trends Ecol. Evol. (Amst.), 16:178-183 (2001).

Xavier, J.B., "Social interaction in synthetic and natural microbial communities," Mol. Syst. Biol., 7:483 (2011).

Raj, A. and Van Oudenaarden, A., "Nature, Nurture, or Chance: Stochastic Gene Expression and Its Consequences," Cell, 135:216-226 (2008).

Eldar, A. and Elowitz, M.B., "Functional roles for noise in genetic circuits" Nature, 467:167-173 (2010).

Kuchina, A. et al., "Temporal competition between differentiation programs determines cell fate choice," Molecular Systems Biology, 7:557-557 (2014).

Elowitz, M.B., "Stochastic Gene Expression in a Single Cell," Science, 297:1183-1186 (2002).

Russell, J.R. et al., "Noise in a phosphorelay drives stochastic entry into sporulation in Bacillus subtilis," EMBO J., 36:2856-2869 (2017).

Stapels, D.A.C et al., "*Salmonella persisters* undermine host immune defenses during antibiotic treatment," Science, 362:1156-1160 (2018).

Locke, J.C.W. and Elowitz, M.B., "Using movies to analyse gene circuit dynamics in single cells," Nat. Rev. Microbiol., 7:383-392 (2009).

Rosenthal, A.Z. et al., "Metabolic interactions between dynamic bacterial subpopulations," Elife, 7 (2018), doi:10.7554/eLife.33099.

Rosenberg, A.B. et al., "Single-cell profiling of the developing mouse brain and spinal cord with split-pool barcoding," Science, eaam8999 (2018).

Fan, H.C. et al., "Combinatorial labeling of single cells for gene expression cytometry," Science, 347:1258367-1258367 (2015).

Macosko, E.Z. et al., "Highly Parallel Genome-wide Expression Profiling of Individual Cells Using Nanoliter Droplets," Cell, 161:1202-1214 (2015).

Klein, A.M. et al., "Droplet Barcoding for Single-Cell Transcriptomics Applied to Embryonic Stem Cells," Cell, 161:1187-1201 (2015).

Zheng, G.X.Y. et al., "Massively parallel digital transcriptional profiling of single cells," Nature Communications, 8:14049 (2017).

Cao, J. et al., "Comprehensive single-cell transcriptional profiling of a multicellular organism," Science, 357:661-667 (2017).

Howick, V.M. et al., "The Malaria Cell Atlas: Single parasite transcriptomes across the complete Plasmodium life cycle," Science, 365:eaaw2619 (2019).

Han, X. et al., "Mapping the Mouse Cell Atlas by Microwell-Seq," Cell, 172:1091-1107.e17 (2018).

Saunders, A. et al., "Molecular Diversity and Specializations among the Cells of the Adult Mouse Brain," Cell, 174:1015-1030.e16 (2018).

Davie, K. et al., "A Single-Cell Transcriptome Atlas of the Aging *Drosophila* Brain," Cell, 174:982-998.e20 (2018).

Zeisel, A. et al., "Molecular Architecture of the Mouse Nervous System," Cell, 174:999-1014.e22 (2018).

Kang, Y. et al., "Transcript amplification from single bacterium for transcriptome analysis," Genome Res., 21:925-935 (2011).

(56) References Cited

OTHER PUBLICATIONS

Wang, J. et al., "RNA-seq based transcriptomic analysis of single bacterial cells," Integr Biol., 7:1466-1476 (2015).
Arsène, F. et al., "The heat shock response of *Escherichia coli*," International Journal of Food Microbiology, 55:3-9 (2000).
Schumann, W., "The Bacillus subtilis heat shock stimulon," Cell Stress Chaperones, 8:207-217 (2003).
Thieringer, H.A. et al., "Cold shock and adaptation," BioEssays, 20:49-57 (1998).
Yoshida, K. et al., "myo-Inositol Catabolismin Bacillus subtilis," J. Biol. Chem., 283:10415-10424 (2008).
Miwa, Y. and Fujita, Y., "Involvement of two distinct catabolite-responsive elements in catabolite repression of the Bacillus subtilis myo-inositol (iol) operon," J. Bacteriol., 183:5877-5884 (2001).
Yoshida, K.-I. et al., "Interaction of a Repressor and its Binding Sites for Regulation of the Bacillussubtilis iol Divergon," Journal of Molecular Biology, 285:917-929 (1999).
Wu, X. et al., "A Toxin-Antitoxin Module in Bacillus subtilis Can Both Mitigate and Amplify Effects of Lethal Stress," PLOS One, 6:e23909 (2011).
Shelburne, C.E. et al., "The spectrum of antimicrobial activity of the bacteriocin subtilosin A," J Antimicrob Chemother., 59:297-300 (2007).
Patel, P.S. et al., "Bacillaene, a novel inhibitor of procaryotic protein synthesis produced by Bacillus subtilis: production, taxonomy, isolation, physico-chemical characterization and biological activity," J. Antibiot., 48:997-1003 (1995).
Gao, L. et al., "Plipastatin and surfactin coproduction by Bacillus subtilis pB2-L and their effects on microorganisms," Antonie van Leeuwenhoek, 110:1007-1018 (2017).
Hanlon, D.W. et al., "Identification of TlpC, a novel 62 kDa MCP-like protein from Bacillus subtilis," Microbiology, 140:1847-1854 (1994).
Allard-Massicotte, R. et al., "Bacillus subtilis Early Colonization of *Arabidopsis thaliana* Roots Involves Multiple Chemotaxis Receptors," mBio, 7 (2016), doi:10.1128/mBio.01664-16.
Howe, K.L. et al., "Ensembl Genomes 2020—enabling non-vertebrate genomic research," Nucleic Acids Res, doi:10.1093/nar/gkz890.
Dobin, C.A. et al., "STAR: ultrafast universal RNA-seq aligner," Bioinformatics, 29:15-21 (2013).
Wolf, F.A. et al., "SCANPY: large-scale single-cell gene expression data analysis," Genome Biology, 19:15 (2018).
Luecken, M.D. and Theis, F.J., "Current best practices in single-cell RNA-seq analysis: a tutorial," Mol. Syst. Biol., 15:e8746 (2019).
Stuart, T. et al., "Comprehensive Integration of Single-Cell Data," Cell, 177:1888-1902.e21 (2019).
Mukherjee, S. et al., "Scalable preprocessing for sparse scRNA-seq data exploiting prior knowledge," Bioinformatics, 34:i124-i132 (2018).
Johnson, W.E. et al., "Adjusting batch effects in microarray expression data using empirical Bayes methods," Biostatistics, 8:118-127 (2007).
Pederson, B., patsy version of ComBat for removing batch effects. (GitHub, 2012; https://github.com/brentp/combat.by).
Pedregosa, F. et al., "Scikit-learn: Machine Learning in Python," Journal of Machine Learning Research, 12:2825-2830 (2011).
Van Der Maaten, L., "Accelerating t-SNE using Tree-Based Algorithms," Journal of Machine Learning Research, 15:3221-3245 (2014).
McInnes, L. et al., "UMAP: Uniform Manifold Approximation and Projection for Dimension Reduction," arXiv:1802.03426 [cs, stat] (2018) (available at http://arxiv.org/abs/1802.03426).
Zhu, B. and Stülke, J., "SubtiWiki in 2018: from genes and proteins to functional network annotation of the model organism Bacillus subtilis," Nucleic Acids Res., 46:D743-D748 (2018).
Chai, Y. et al., "A Widely Conserved Gene Cluster Required for Lactate Utilization in Bacillus subtilis and Its Involvement in Biofilm Formation," Journal of Bacteriology, 191:2423-2430 (2009).

Tojo, S. et al., "Heavy Involvement of Stringent Transcription Control Depending on the Adenine or Guanine Species of the Transcription Initiation Site in Glucose and Pyruvate Metabolism in Bacillus subtilis," Journal of Bacteriology, 192:1573-1585 (2010).
Nicholson, W.L., "Bacillus subtilis ydjL (bdhA) Gene Encodes Acetoin Reductase/2,3-Butanediol Dehydrogenase," Applied and Environmental Microbiology, 74:6832-6838 (2008).
Asai, K. et al., ", Regulation of the transport system for C4-dicarboxylic acids in Bacillus subtilis," Microbiology, 146:263-271 (2000).
Blencke, H.-M. et al., "Transcriptional profiling of gene expression in response to glucose in Bacillus subtilis: regulation of the central metabolic pathways," Metabolic Engineering, 5:133-149 (2003).
Kormelink, T. et al., "Comparative genome analysis of central nitrogen metabolism and its control by GlnR in the class Bacilli," BMC Genomics, 13:191 (2012).
Randazzo, P. et al., "Revisiting the in vivo GlnR-binding sites at the genome scale in Bacillus subtilis," BMC Research Notes, 10 (2017), doi:10.1186/s13104-017-2703-9.
Heravi, K.M. and Altenbuchner, J., "Cross Talk among Transporters of the Phosphoenolpyruvate-Dependent Phosphotransferase System in Bacillus subtilis," Journal of Bacteriology, 200 (2018), doi:10.1128/JJB.00213-18.
Garrity, L.F. et al., "Unique regulation of carbohydrate chemotaxis in Bacillus subtilis by the phosphoenolpyruvate-dependent phosphotransferase system and the methyl-accepting chemotaxis protein McpC," J. Bacteriol., 180:4475-4480 (1998).
Jordan, S. et al., "Regulation of LiaRS-Dependent Gene Expression in Bacillus subtilis: Identification of Inhibitor Proteins, Regulator Binding Sites, and Target Genes of a Conserved Cell Envelope Stress-Sensing Two-Component System," Journal of Bacteriology, 188:5153-5166 (2006).
Ye, B.-C. et al., "Time-Resolved Transcriptome Analysis of Bacillus subtilis Responding to Valine, Glutamate, and Glutamine," PLoS One, 4:e7073 (2009).
Cárdenas, P.P. et al., RecX Facilitates Homologous Recombination by Modulating RecA Activities. PLoS Genetics, 8:e1003126 (2012).
Berka, R.M. et al., "Microarray analysis of the Bacillus subtilis K-state: genome-wide expression changes dependent on ComK," Molecular Microbiology, 43:1331-1345 (2002).
Park, J. et al., "Molecular Time Sharing through Dynamic Pulsing in Single Cells," Cell Syst., 6:216-229.e15 (2018).
Saint, M. et al., "Single-cell imaging and RNA sequencing reveal patterns of gene expression heterogeneity during fission yeast growth and adaptation," Nature Microbiology, 4:480-491 (2019).
Avraham, R. et al., "A highly multiplexed and sensitive RNA-seq protocol for simultaneous analysis of host and pathogen transcriptomes," Nature Protocols, 11(8):1477-1491 (2016).
Hwang, B. et al., "Single-cell RNA sequencing technologies and bioinformatics pipelines," Experimental and Molecular Medicine, 50:Article 96 (2018).
Tolonen, A.C. et al., "Dissecting the human microbiome with single-cell genomics," BioMed Central Genome Medicine, 9:56 (2017).
Xu, Y. et al., "Single-cell metagenomics: challenges and applications," Protein and Cell, 9(5):501-510 (2018).
Islam, S. et al., "Quantitative single-cell RNA-seq with unique molecular identifiers," Nature Methods, 11:163-166 (2014).
Tjaden, B. et al., "De novo assembly of bacterial transcriptomes from RNA-seq data," Genome Biology, 16:1 (2015).
Saliba, A.E. et al., "Single-cell RNA-seq ties macrophage polarization to growth rate of intracellular *Salmonella*," Nature Microbiology, 2:16206 (2017).
Bossert, M. et al., "Improving the Reliability of RNA-seq: Approaching Single-Cell Transcriptomics To Explore Individuality in Bacteria," in Information and Communication Theory in Molecular Biology, Ch. 7, pp. 181-198 (2017).
Blattman, S.B. et al., "Prokaryotic single-cell RNA sequencing by in situ combinatorial indexing," Nature Microbiology, 5:1192-1201 (2020).
Ma, Q. et al., "Single-Cell RNA Sequencing of Plant-Associated Bacterial Communities," Frontiers in Microbiology, 10:2452 (2019).

(56) References Cited

OTHER PUBLICATIONS

Avital, G. et al., "scDual-Seq: mapping the gene regulatory program of *Salmonella* infection by host and pathogen single-cell RNA-sequencing," Genome Biology, 18:200 (2017).
Mestre-Farràs, N. et al., "Using single-cell ma sequencing to study host-pathogen interactions," Master's Thesis, Department of Molecular Biology and Biotechnology, Feb. 15, 2018.
Liu, S. and Trapnell, C., Single-cell transcriptome sequencing: recent advances and remaining challenges. F1000Res. 5 (2016), doi:10.12688/f1000research.7223.1.
Wendisch, V.F. et al., Isolation of *Escherichia coli* mRNA and comparison of expression using mRNA and total RNA on DNA microarrays, Anal. Biochem., 290:205-213 (2001).
He, S. et al., "Validation of two ribosomal RNA removal methods for microbial metatranscriptomics," Nature Methods, 7:807-812 (2010).
Bartholomäus, A. et al., "Bacteria differently regulate mRNA abundance to specifically respond to various stresses," Philos Trans A Math Phys Eng Sci., 374:20150069 (2016), doi:10.1098/rsta.2015.0069.
Mohanty, B.K. and Kushner, S.R., "New Insights into the Relationship between tRNA Processing and Polyadenylation in *Escherichia coli*," Trends in Genetics, 35:434-445 (2019).
Haldenwang, W.G., "The sigma factors of Bacillus subtilis," Microbiol. Mol. Biol. Rev., 59:1-30 (1995).
Helmann, J.D., "Bacillus subtilis extracytoplasmic function (ECF) sigma factors and defense of the cell envelope," Current Opinion in Microbiology, 30:122-132 (2016).
Stülke, J. and Hillen, W., "Regulation of Carbon Catabolismin *bacillus* Species," Annual Review of Microbiology, 54:849-880 (2000).
Pechter, K.B. et al., "Two Roles for Aconitase in the Regulation of Tricarboxylic Acid Branch Gene Expression in Bacillus subtilis," Journal of Bacteriology, 195:1525-1537 (2013).
Singh, K.D. et al., "Carbon Catabolite Repression in Bacillus subtilis: Quantitative Analysis of Repression Exerted by Different Carbon Sources," Journal of Bacteriology, 190:7275-7284 (2008).
Yoshida, K.I. et al., "Organization and transcription of the myo-inositol operon, iol, of Bacillus subtilis," Journal of Bacteriology, 179:4591-4598 (1997).
Marciniak, B.C. et al., "High- and low-affinity cre boxes for CcpA binding in Bacillus subtilis revealed by genome-wide analysis," BMC Genomics, 13:401 (2012).
Ben-Jacob, E. and Schultz, D., "Bacteria determine fate by playing dice with controlled odds," Proceedings of the National Academy of Sciences, 107:13197-13198 (2010).
Granato, E.T. et al., "The Evolution and Ecology of Bacterial Warfare," Current Biology, 29:R521-R537 (2019).
Van Gestel, J. et al., "From Cell Differentiation to Cell Collectives: Bacillus subtilis Uses Division of Labor to Migrate," PLOS Biology, 13:e1002141 (2015).
Kearns, D.B. and Losick, R., "Cell population heterogeneity during growth of Bacillus subtilis," Genes Dev., 19:3083-3094 (2005).
López, D. et al., "Paracrine signaling in a bacterium," Genes Dev., 23:1631-1638 (2009).
Krüger, E. et al., "The clp proteases of Bacillus subtilis are directly involved in degradation of misfolded proteins," J. Bacteriol., 182:3259-3265 (2000).
Mhatre, E. et al., "The impact of manganese on biofilm development of Bacillus subtilis," Microbiology (Reading, Engl.), 162:1468-1478 (2016).
Wood, H.E. et al., "Characterization of PBSX, a defective prophage of Bacillus subtilis," J. Bacteriol., 172:2667-2674 (1990).
Goranov, A.I. et al., "Characterization of the Global Transcriptional Responses to Different Types of DNA Damage and Disruption of Replication in Bacillus subtilis," Journal of Bacteriology, 188:5595-5605 (2006).
Anderson, L.M. and Bott, K.F., "DNA packaging by the Bacillus subtilis defective bacteriophage PBSX," J. Virol., 54:773-780 (1985).

Shingaki, R. et al., "Chromosome DNA fragmentation and excretion caused by defective prophage gene expression in the early-exponential-phase culture of Bacillus subtilis," Canadian Journal of Microbiology, 49:313-325 (2003).
Nanda, A.M. et al., "Impact of Spontaneous Prophage Induction on the Fitness of Bacterial Populations and Host-Microbe Interactions," Journal of Bacteriology, 197:410-419 (2015).
Süel, G.M. et al., "An excitable gene regulatory circuit induces transient cellular differentiation," Nature, 440:545-550 (2006).
Hamoen, L.W. et al., "Controlling competence in Bacillus subtilis: shared use of regulators," Microbiology, 149:9-17 (2003).
Ogura, M. et al., "Whole-genome analysis of genes regulated by the Bacillus subtilis competence transcription factor ComK," J. Bacteriol., 184:2344-2351 (2002).
Grundy, F.J. et al., "Regulation of the Bacillus subtilis acetate kinase gene by CcpA," Journal of Bacteriology, 175:7348-7355 (1993).
Sastalla, I. et al., "Codon-Optimized Fluorescent Proteins Designed for Expression in Low-GC Gram-Positive Bacteria," Appl Environ Microbiol., 75:2099-2110 (2009).
Chastanet, A. et al., "Broadly heterogeneous activation of the master regulator for sporulation in Bacillus subtilis," Proceedings of the National Academy of Sciences, 107:8486-8491 (2010).
Luo, Y. et al., "Transcriptomic and Phenotypic Characterization of a Bacillus subtilis Strain without Extracytoplasmic Function Factors," Journal of Bacteriology, 192:5736-5745 (2010).
Ludwig, H. et al., "Transcription of glycolytic genes and operons in Bacillus subtilis: evidence for the presence of multiple levels of control of the gapA operon," Molecular Microbiology, 41:409-422 (2001).
Larsson, J.T., "Coordinated patterns of cytochrome bd and lactate dehydrogenase expression in Bacillus subtilis," Microbiology, 151:3323-3335 (2005).
Wei, Y. et al., "Bacillus subtilis YqkI Is a Novel Malic/Na + -Lactate Antiporter That Enhances Growth on Malate at Low Protonmotive Force," Journal of Biological Chemistry, 275:30287-30292 (2000).
Lowe, P.N. et al., "Dual role of a single multienzyme complex in the oxidative decarboxylation of pyruvate and branched-chain 2-oxo acids in Bacillus subtilis," Biochemical Journal, 215:133-140 (1983).
Smits, W.K. et al., "Temporal separation of distinct differentiation pathways by a dual specificity Rap-Phr system in Bacillus subtilis," Molecular Microbiology, 65:103-120 (2007).
U.S. Appl. No. 18/455,080, filed Aug. 24, 2023; Georg Seelig et al.
U.S. Appl. No. 18/455,113, filed Aug. 24, 2023; Georg Seelig et al.
U.S. Appl. No. 18/455,133, filed Aug. 24, 2023; Georg Seelig et al.
U.S. Appl. No. 18/455,152, filed Aug. 24, 2023; Georg Seelig et al.
Islam et al., 2013, "Quantitative single-cell RNA-seq with unique molecular identifiers," Nature Methods (Dec. 22, 2013).
Lee et al., 2014, "Highly Multiplexed Subcellular RNA Sequencing in Situ," 343 Science 1360-1363 (published Feb. 27, 2014).
Ligasová and Koberna, 2010, "In situ reverse transcription: the magic of strength and anonymity," 38(16) Nucleic Acids Research e167 (published Jul. 13, 2010).
Mamanova et al., 2010, "FRT-seq: Amplification-free, strand-specific, transcriptome sequencing," 7(2) Nature Methods 130 (Feb. 2010).
McDavid et al., 2012, "Data exploration, quality control and testing in single-cell qPCR," 29(4) Bioinformatics 461 (Dec. 24, 2012).
Miller et al., 2009, "TU-tagging: cell type specific RNA isolation from intact complex tissues," 6(6) Nature Methods 439 (Jun. 2009).
Picelli et al., 2014, "Full-length RNA-seq from single cells using Smart-seq2," Nature Protocols 171 (Jan. 2, 2014).
Plessy et al., 2012, "Population transcriptomics with single-cell resolution: A new field made possible by microfluidics," 35(2) Bioessays 131 (2012).
Politz & Singer, 1999, "In situ reverse transcription for detection of hybridization between oligonucleotides and their intracellular targets," Methods Jul. 1999; 18(3):281-5.
Schmid et al., 2012, "A Powerful Method for Transcriptional Profiling of Specific Cell Types in Eukaryotes: Laser-Assisted Microdissection and RNA Sequencing," 7(1) PLoS One e29685 (Jan. 26, 2012).
Shimizu et al., 2014, "Qualitative De Novo Analysis of Full Length cDNA and Quantitative Analysis of Gene Expression for Common

(56) References Cited

OTHER PUBLICATIONS

Marmoset (Callithrix jacchus) Transcriptomes Using Parallel Long-Read Technology and Short-Read Sequencing," 9(6) PLoS One e100936 (Jun. 2014).
Swaroop & Xu, 1993, cDNA libraries from human tissues and cell lines, 64 Cytogenetic Cell Genetics 292 (1993).
Tang et al., 2009, "mRNA-Seq whole-transcriptome analysis of a single cell," 6(5) Nature Methods 377 (Apr. 6, 2009).
Treutlein et al., 2014, Reconstruction lineage hierarchies of the distal lung epithelium using single-cell RNA-seq, 509 Nature 371 (May 15, 2014).
Vivancos, et al., 2010, "Strand-specific deep sequencing of the transcriptome," 20 Genome Research 989 (Jun. 2, 2010).
Vo & Jedlicka, 2014, "Protocols for metagenomic DNA extraction and Illumina amplicon library preparation for fecal and swab samples," Molecular Ecology Resources (Apr. 2014).
Wuest et al., 2013, "Cell-specific expression profiling of rare cell types as exemplified by its impact on our understanding of female gametophyte development," 16(1) Current Opinion in Plant Biology 41 (2013).
Ying et al., 1999, "Generation of Full-Length cDNA Library from Single Human Prostate Cancer Cells," 27(3) Biotechniques 410-14 (published Sep. 1999).
Yozwiak et al., 2010, "Human Enterovirus 109: a Novel Interspecies Recombinant Enterovirus Isolated from a Case of Acute Pediatric Respiratory Illness in Nicaragua," 84(18) J. Virology 9047 (Sep. 2010).
Zhang et al., 2012, "Strand-specific libraries for high throughput RNA sequencing (RNA-Seq) prepared without poly(A) selection," 3(9) Silence (2012).
Zhong et al., 2011, "High-Throughput Illumina Strand-Specific RNA Sequencing Library Preparation," Cold Spring Harbor Protocols 940 (Aug. 2011).
Civil Action No. 22-1597-CJB; Parse Biosciences Inc.'S First Supplemental and Amended Invalidity Contentions; Sep. 15, 2023; 33 pages.
Adey, et al., In vitro, long-range sequence information for de novo genome assembly via transposase contiguity, Genome Res. 24, 2041-2049, 2014.
Adey, et al., Rapid, low-input, low-bias construction of shotgun fragment libraries by high-density in vitro transposition, Genome Biol. 11, R119, 2010.
Amini, et al., Haplotype-resolved whole-genome sequencing by contiguity-preserving transposition and combinatorial indexing, Nat. Genet. 46, 1343-1349, Dec. 2014.
Boyle, et al., High-Resolution Mapping and Characterization of Open Chromatin Across the Genome, Cell 132, 3110-322, Jan. 25, 2008.
Buenrostro, et al., Transposition of native chromatin for fast and sensitive epigenomic profiling of open chromatin, DNA-binding proteins and nucleosome position, Nat. Methods 10, 1213-1218, Dec. 2013.
Casanovich, et al., Multiplex singe-cell profiling of chromatin accessibilty by combinatorial cellular indexing, Science, vol. 348, Issue 6237, pp. 910-914, May 22, 2015.
Deng, et al., Single-Cell RNA-Seq Reveals Dynamic, Random Monoallelic Gene Expression in Mammalian Cells, Science, 343, 193-196, Jan. 10, 2014.
Fan, et al., Combinatorial labeling of single cells for gene expression cytometry, Science, vol. 347, Issue 6222, 1258367, Feb. 6, 2015.
Fu, et al., Counting individual DNA Molecules by the stochastic attachment of diverse labels, Proc Natl Acad Sci. May 31, 2011; 108(22): 9026-31.
Fu, et al., Molecular Indexing Enables quantitative targeted RNA sequencing and reaveals poor efficiencies in standard library preparations, Proc Natl Acad Sci. Feb. 4, 2014; 111(5); 1891-1896.
Gole, et al., Massively Parallel Polymerase Cloning and Genome Sequencing of Single Cells Using Nanoliter Microwells, Nat. Biotechnol. 31, 1126-1132, Dec. 2013.
Jaitin, et al., Massively Parallel Single-Cell RNA-Seq for Marker-Free Decomposition of Tissues into Cell Types, Science 343, 776-779, Feb. 14, 2014.
Kivioja, et al., Counting absolute Nos. of molecules using unique molecular identifiers, Nature Methods, Jan. 2012, vol. 9, No. 1, 72-74.
Klein, et al.,Droplet Barcoding for Single-Cell Transcriptomics Applied to Embryonic Stem Cells, May 21, 2015, Cell 161, 1187-1201.
Macosko, et al., Highly Parallel Genome-Wide Expression Profiling of Individual Cells Using Nanoliter Droplets, Cell, 161, 1202-1214, May 21, 2015.
Mortazavi, et al., Mapping and quantifying mammalian transcriptomes by RNA-Seq, Nat Methods 5(7): 621-628, May 30, 2008.
Nagano, et al., Single-Cell Hi-C Reveals Cell-to-Cell Variability in Chromosome Structure, Nature 502, 59-64, Oct. 3, 2013.
Navin, et al., Tumour evolution inferred by single-cell sequencing, Nature 472, 90-94, Apr. 7, 2011.
Pan, et al., Single Cell Analysis: from Technology to Biology and Medicine, Single Cell Biol. 3, 106, 2014.
Regev, et al., The Human Cell Atlas, www.genome.gov/Multimedia/slides/GSPFuture2014/10_Regev.pdf.
Rotem, et al., High-Throughput Single-Cell Labeling (Hi-SCL) for RNA-Seq Using Drop-Based Microfluidics, PLoS One 10(5): e0116328, May 22, 2015.
Saliba, et al.,Single-cell RNA-seq: advances and future challenges, Nucleic Acids Res. 42, 8845-8860, Jul. 22, 2014.
Shalek, et al., Single-Cell transcriptomics reveals bimodality in expression and splicing in immune cells, Nature 498, 236-240, Jun. 13, 2013.
Shiroguchi, et al., Digital RNA sequencing minimizes sequence-dependent bias and amplification noise with optimized single-molecule barcodes, Proc Natl Acad Sci. Jan. 24, 2012; 109(4): 1347-52.
Smallwood, et al., Single-Cell Genome-Wide Bisulfite Sequencing for Assessing Epigenetic Heterogeneity, Nat. Methods 11, 817-820, Aug. 2014.
Stergachis, et al., Developmental Fate and Cellular Maturity Encoded in Human Regulatory DNA Landscapes, Cell 154, 888-903 Aug. 15, 2013.
The Encode Project Consortium, et al., An Integrated encyclopedia of DNA elements in the human genome, Nature 489, 57-74, 2012.
Thurman, et al., The Accessible Chromatin Landscape of the Human Genome, Nature 489, 75-82, Sep. 6, 2012.
Trapnell, et al., The Dynamics and Regulators of Cell Fate Decisions are Revealed by Pseudotemporal Ordering of Single Cells, Nat. Biotechnol. 32, 381-386, Apr. 2014.
Wu, et al., Quantitative Assessment of Single-Cell RNA-sequencing methods, Nat. Methods 11, 41-46, Jan. 2014.
Yang, et al., Global survey of escape from X inactivation by RNA-sequencing in mouse, Genome Res. 20, 614-622, 2010.
Jaitin, et al., "Massively Parallel Single-Cell RNA-Seq for Marker-Free Decomposition of Tissues into Cell Types," Science, 343(6172):776-779 online Supplement, 2014.
Matsuda, et al., "Comparison of Fixation Methods for Preservation of Morphology, RNAs, and Proteins From Paraffin-Embedded Human Cancer Cell-Implanted Mouse Models," Journal of Histochemistry & Cytochemistry, 59 (1):68-75, 2011.
U.S. Appl. No. 62/094,917, filed Dec. 19, 2014; Nolan.
U.S. Appl. No. 62/094,919, filed Dec. 19, 2014; Nolan.
U.S. Appl. No. 62/094,924, filed Dec. 19, 2014; Nolan.
Civil Action No. 1:22-CV-01597-CJB; Scale Biosciences, Inc.'s Initial Invalidity Contentions; 501 pages.
Moignard, V. et al., "Decoding the regulatory network of early blood development from single-cell gene expression measurements," Nature Biotechnology, 33(3):269-276, Mar. 2015.
Moriyama, M. et al., "Complement Receptor 2 Is Expressed in Neural Progenitor Cells and Regulates Adult Hippocampal Neurogenesis," The Journal of Neuroscience, 31(11):3981-3989, Mar. 16, 2011.

(56) References Cited

OTHER PUBLICATIONS

Murthy, M. et al., "Transcription factor Runx1 inhibits proliferation and promotes developmental maturation in a selected population of inner olfactory nerve layer olfactory ensheathing cells," Gene, 540:191-200, 2014.

Nagalski, A. et al., "Molecular anatomy of the thalamic complex and the underlying transcription factors," Brain Struct. Funct., 221:2493-2510, 2016.

Nakashima, K. et al., "Cerebellar Granule Cells Are Predominantly Generated by Terminal Symmetric Divisions of Granule Cell Precursors," Developmental Dynamics, 244:748-758, 2015.

Nielsen, J.V. et al., "Zbtb20-Induced CA1 Pyramidal Neuron Development and Area Enlargement in the Cerebral Midline Cortex of Mice," Cerebral Cortex, 20:1904-1914, Aug. 2010.

Ogawa, M. et al., "The reeler Gene-Associated Antigen on Cajal-Retzius Neurons Is a Crucial Molecule for Laminar Organization of Cortical Neurons," Neuron, 14:899-912, May 1995.

Pedregosa, F. et al., "Scikit-learn: Machine Learning in Python," Journal of Machine Learning Research, 12:2825-2830, published Oct. 2011.

Petracca, Y.L. et al., "The late and dual origin of cerebrospinal fluid-contacting neurons in the mouse spinal cord," Development, 143:880-891, 2016.

Picelli, S. et al., "Smart-seq2 for sensitive full-length transcriptome profiling in single cells," Nature Methods, 10:1096-1098, 2013.

Rosenberg, A.B. et al., "Scaling single cell transcriptomics through split pool barcoding," BioRxiv, 2017, available at: https://doi.org/10.1101/105163.

Rosenberg, A.B. et al., "Single-cell profiling of the developing mouse brain and spinal cord with split-pool barcoding," Science, 360(6385):176-182, 2018.

Rosenberg, A.B. et al., "Single-cell profiling of the developing mouse brain and spinal cord with split-pool barcoding—supplementary materials," retrieved from the Internet at https://science.sciencemag.org/content/sci/suppl/2018/03/14/science.aam8999.DC1/aam8999_Rosenberg_SM.pdf, Apr. 13, 2018, 55 pages.

Saab, A.S. et al., "Bergmann Glial AMPA Receptors Are Required for Fine Motor Coordination," Science, 337:749-753, Aug. 10, 2012.

Salero, E. and Hatten, M.E., "Differentiation of ES cells into cerebellar neurons," Proc. Natl. Acad. Sci. USA, 104 (8):2997-3002, Feb. 20, 2007.

Sánchez-Mendoza, E. et al., "Review: Could neurotransmitters influence neurogenesis and neurorepair after stroke?" Neuropathology and Applied Neurobiology, 39:722-735, 2013.

Sang, L. et al., "Control of the Reversibility of Cellular Quiescence by the Transcriptional Repressor HES1," Science, 321:1095-1100, Aug. 22, 2008.

Schilling, K. et al., "Besides purkinje cells and granule neurons: an appraisal of the cell biology of the interneurons of the cerebellar cortex," Histochem. Cell Biol., 130:601-615, 2008.

Seal, R.P. et al., "Injury-induced mechanical hypersensitivity requires C-low threshold mechanoreceptors," Nature, 462:651-655, Dec. 3, 2009.

Shekhar, K. et al. "Comprehensive Classification of Retinal Bipolar Neurons by Single-Cell Transcriptomics," Cell, 166:1308-1323, Aug. 25, 2016.

Song, H. et al., "Ascl1 and Helt act combinatorially to specific thalamic neuronal identity by repressing Dlxs activation," Developmental Biology, 398:280-291, 2015.

Sudarov, A. and Joyner, A.L., "Cerebellum morphogenesis: the foliation pattern is orchestrated by multi-cellular anchoring centers," Neural Development, 2:26, 21 p. Dec. 3, 2007.

Tasic, B. et al., "Adult mouse cortical cell taxonomy revealed by single cell transcriptomics," Nature Neuroscience, 19(2):335-346, Feb. 2016.

Thompson, C.L. et al., "A High-Resolution Spatiotemporal Atlas of Gene Expression of the Developing Mouse Brain," Neuron, 83:309-323, Jul. 16, 2014.

Thomsen, E.R. et al., "Fixed single-cell transcriptomic characterization of human radial glial diversity," Nature Methods, 13(1):87-93, Jan. 2016.

Tirosh, I. et al., "Dissecting the multicellular ecosystem of metastatic melanoma by single-cell RNA-seq," Science, 352(6282):189-196, Apr. 8, 2016, corrected Feb. 1, 2019.

Tritsch, N.S. et al., "Dopaminergic neurons inhibit striatal output through non-canonical release of GABA," Nature, 490:262-266, Oct. 11, 2012.

Qiu, X. et al., "Reversed graph embedding resolves complex single-cell trajectories," Nature Methods, 14(10:979-982, Oct. 2017.

Valcanis, H. and Tan, S-S., "Layer Specification of Transplanted Interneurons in Developing Mouse Neocortex," The Journal of Neuroscience, 23(12):5113-5122, Jun. 15, 2003.

Van Der Maaten, L., "Accelerating t-SNE using Tree-Based Algorithms," Journal of Machine Learning Research, 15:3221-3245, published Oct. 2014.

Venteicher, A.S. et al., "Decoupling genetics, linearges, and microenvironment in IDH-mutant gliomas by single-cell RNA-seq," Science, 335:eaai8478, 1391, Mar. 31, 2017.

Weisheit, G. et al., "Postnatal development of the murine cerebellar cortex: formation and early dispersal of basket, stellate and Golgi neurons," European Journal of Neuroscience, 24:466-478, 2006.

Wisniewska, M.B. et al., "LEF1/beta-Catenin Complex Regulates Transcription of the Cav3.1 Calcium Channel Gene (Cacna1g) in Thalamic Neurons of the Adult Brain," The Journal of Neuroscience, 30(14):4957-4969, Apr. 7, 2010.

Xie, Z. et al., "Zbtb20 is essential for the specification of CA1 field identity in the developing hippocampus," Proc. Natl. Acad. Sci. USA, 107(14):6510-6515, Apr. 6, 2010.

Yang, M.J. e tal., "Mitral and Tufted Cells Are Potential Cellular Targets of Nitration in the Olfactory Bulb of Aged Mice," PLoS One, 8(3):e59673, 11 pages, Mar. 2013.

Yao, Z. et al., "A Single-Cell Roadmap of Lineage Bifurcation in Human ESC Models of Embryonic Brain Development," Cell Stem Cell, 20:120-134, Jan. 15, 2017.

Zeisel, A. et al., "Cell types in the mouse cortex and hippocampus revealed by single-cell RNA-seq," Science, 347 (6226):1138-1142, Mar. 6, 2015.

Zhao, C. et al., "Mechanisms and Functional Implications of Adult Neurogenesis," Cell, 132:645-660, Feb. 22, 2008.

Zheng, C. et al., "Landscape of Infiltrating T Cells in Liver Cancer Revealed by Single-Cell Sequencing," Cell, 169:1342-1356, Jun. 15, 2017.

Zheng, G.X.Y. et al., "Massively parallel digital transcriptional profiling of single cells," Nature Communications, 8:14049 (12 pages), published Jan. 16, 2017.

Zorita, E. et al., "Starcode: sequence clustering based on all-pairs search," Bioinformatics, 31(12):1913-1919, 2015.

Shah, S. et al., "In Situ Transcription Profiling of Single Cells Reveals Spatial Organization of Cells in the Mouse Hippocampus," Neuron, 92:342-357, Oct. 19, 2016.

Burton, et al., 2013, "Chromosome-scale scaffolding of de novo genome assemblies based on chromatin interactions," 31(12) Nature Biotechnology 1119 (Nov. 3, 2013).

Cao, et al., 2017, "Comprehensive single cell transcriptional profiling of a multicellular organism by combinatorial indexing," bioRxiv, Cold Spring Harbor Laboratory; Feb. 2, 2017; doi: https://doi.org/10.1101/104844.

Croucher, et al., 2009, "A simple method for directional transcriptome sequencing using Illumina technology," 37(22) Nucleic Acids Research e148 (Oct. 8, 2009).

Eberwine, et al., 2014, "The promise of single-cell sequencing," 11(1) Nat. Methods 25 (Jan. 2014).

Gertz, et al., 2011, "Transposase mediated construction of RNA-seq libraries," 22 Genome Research 134-141 (published Nov. 29, 2011).

Gomez-Lozano, et al., 2012, "Genome-wide identification of novel small RNAs in Pseudomonas aeruginosa," 14(8) Env't Microbiology 2006 (Apr. 2012).

Gupta and Gupta, 2014, "Next Generation Sequencing and Its Applications," Animal Biotechnology. Models in Discovery and Translation (Ashish S. Verma and Anchal Singh, eds., Academic Press, Oxford) (2014).

(56) References Cited

OTHER PUBLICATIONS

Islam et al., 2011, "Characterization of the single-cell transcriptional landscape by highly multiplex RNA-seq," 21(7) Genome Research 1160 (May 4, 2011).
Abraham, H. et al., "p73 and Reelin in Cajal-Retzius Cells of the Developing Human Hippocampal Formation," Cerebral Cortex, 14(5):484-495, May 2004.
Alcamo, E.A. et al., "Satb2 Regulates Callosal Projection Neuron Identity in the Developing Cerebral Cortex," Neuron, 57:364-377, Feb. 7, 2008.
Alifragis, P. et al., "Lhx6 Regulates the Migration of Cortical Interneurons from the Ventral Telencephalon But Does Not Specify their GABA Phenotype," The Journal of Neuroscience, 24(24):5643-5648, Jun. 16, 2004.
Altman, J. and Bayer, S.A., "Development of the Precerebellar Nuclei in the Rat: I. The Precerebellar Neuroepithelium of the Rhombencephalon," The Journal of Comparative Neurology, 257:477-489, 1987.
Afsari, Z.H. et al., "Alteration of Glial Fibrillary Acidic Proteins Immunoreactivity in Astrocytes of the Spinal Cord Diabetic Rats," Anat. Rec. Adv. Integr. Anat. Evol. Biol., 291:390-399, 2008.
Belgard, T.G. et al., "A Transcriptomic Atlas of Mouse Neocortical Layers," Neuron, 71:605-616, Aug. 25, 2011.
Bonnet, F. et al., "Structure and Cellular Distribution of Mouse Brain Testican," The Journal of Biological Chemistry, 271(8):4373-4380, Feb. 23, 1996.
Brumovsky, P.R., "VGLUTs in Peripheral Neurons and the Spinal Cord: Time for a Review," ISRN Neurology, 213:829753, 28 pages, 2013.
Butovsky, O. et al., "Identification of a unique TGF-ß-dependent molecular and functional signature in microglia," Nature Neuroscience, 17(1):131-143, Jan. 2014.
Cahoy, J.D. et al., "A Transcriptome Database for Astrocytes, Neurons, and Oligodendrocytes: A New Resource for Understanding Brain Development and Function," The Journal of Neuroscience, 28(1):264-278, Jan. 2, 2008.
Cao, J. et al., "Comprehensive single-cell transcriptional profiling of a multicellular organism," Science, 357(6352):661-667, Aug. 18, 2017.
Cembrowski, M.S. et al., "Hipposeq: a comprehensive RNA-seq database of gene expression in hippocampal principal neurons," eLife, 5:e14997, 22 pages, Apr. 26, 2016.
Chang, J.C. et al., "Mitotic Events in Cerebellar Granule Progenitor Cells That Expand Cerebellar Surface Area Are Critical for Normal Cerebellar Cortical Lamination in Mice," J. Neuropathol. Exp. Neurol., 74(3):261-272, Mar. 2015.
Cheung, K-K. et al., "Dynamic expression of Dab2 in the mouse embryonic central nervous sytem," BMC Developmental Biology, 8:76, 11 pages, Aug. 4, 2008.
Chiu, Y-C. et al., "Foxp2 Regulates Neuronal Differentiation and Neuronal Subtype Specification," Developmental Neurobiology, 74:723-738, 2014.
Chuikov, S. et al., "Prdm16 promotes stem cell maintenance in multiple tissues, partly by regulating oxidative stress," Nature Cell Biology, 12(10):999-1006, Oct. 2010.
Corrales, J.D. et al., "The level of sonic hedgehog signaling regulates the complexity of cerebellar foliation," Development, 133(9):1811-1821, 2006.
Darmanis, S. et al., "A survey of human brain transcriptome diversity at the single cell level," Proc. Natl. Acad. Sci. USA, 112(23):7285-7290, Jun. 9, 2015.
Deangelis, M.M. et al., "Solid-phase reversible immobilization for the isolation of PCR Products," Nucleic Acids Research, 23(22):4742-4743, 1995.
Dobin, A. et al., "STAR: ultrafast universal RNA-seq aligner," Bioinformatics, 29(1):15-21, 2013.
Doyle, J.P. et al., "Application of a Translational Profiling Approach for the Comparative Analysis of CNS Cell Types," Cell, 135:749-762, Nov. 14, 2008.

D'souza, C.A. et al., "Identification of a set of genes showing regionally enriched expression in the mouse brain," BMC Neuroscience, 9:66, 14 pages, Jul. 14, 2008.
Ehmsen, J.T. et al., "The astrocytic transporter SLC7A10 (Asc-1) mediates glycinergic inhibition of spinal cord motor neurons," Scientific Reports, 6:35592, 13 pages, Oct. 19, 2016.
Enjin, A. et al., "Identification of Novel Spinal Cholinergic Genetic Subtypes Disclose Chodl and Pitx2 as Markers for Fast Motor Neurons and Partition Cells," The Journal of Comparative Neurology, 518:2284-2304, 2010.
Erlander, M.G. and Tobin, A.J., "The Structural and Functional heterogeneity of Glutamic Acid Decarboxylase: A Review," Neurochemical Research, 16(3):215-226, 1991.
Ester, M. et al., "A Density-Based Algorithm for Discovering Clusters—A Density-Based Algorithm for Discovering Clusters in Large Spatial Databases with Noise," Proc. Second Int. Conf. Knowl. Discov. Data Min., pp. 226-231, 1996.
Extended European Search Report dated May 20, 2021, in corresponding European Patent Application No. 18858002.1, 7 pages.
Grün, D. et al., "Single-cell messenger RNA sequencing reveals rare intestinal cell types," Nature, 525:251-255, Sep. 10, 2015.
Habib, N. et al., "Div-Seq: Single-nucleus RNA-Seq reveals dynamics of rare adult newborn neurons," Science, 353(6302):925-928, Aug. 26, 2016.
Hashimshony, T. et al., "CEL-Seq: Single-Cell RNA-Seq by Multiplexed Linear Amplification," Cell Reports, 2:666-673, Sep. 27, 2012.
He, L. et al., "Analysis of the brain mural cell transcriptome," Scientific Repeorts, 6:35108, 13 pages, 2016.
Herculano-Houzel, S., "The human brain in numbers a linearly scaled-up primate brain," Frontiers in Human Neuroscience, 3:31, 11 pages, Nov. 9, 2009.
Hesse, K. et al., "AP-δ Is a Crucial Transcriptional Regulator of the Posterior Midbrain," PLoS One, 6(8):e23483, 12 pages, Aug. 2011.
Hickman, S.E. et al., "The microglial sensome revealed by direct RNA sequencing," Nature Neuroscience, 16(12):1896-1905, Dec. 2013.
Honoré, A. et al., "Isolation, Characterization, and Genetic Profiling of Subpopulations of Olfactory Ensheathing Cells from the Olfactory Bulb," Glia, 60:404-413, 2012.
International Search Report and Written Opinion mailed Mar. 27, 2019, for PCT International Patent Application No. PCT/US2018/052283, filed Sep. 21, 2018, 17 pages.
Iwano, T. et al., "Prox1 postmitotically defines dentate gyrus cells by specifying granule cell identity over CA3 pyramidal cell fate in the hippocampus," Development, 139(16):3051-3062, 2012.
Kawasawa, Y.I. et al., "RNA-seq analysis of developing olfactory bulb projection neurons," Molecular and Cellular Neuroscience, 74:78-86, 2016.
Knight, H.M. et al., "GRIK4/KA1 Protein Expression in Human Brain and Correlation with Bipolar Disorder Risk Variant Status," American Journal of Medical Genetics Part B, Neuropsychiatric Genetics, 159B:21-29, 2012.
Lacar, B. et al., "Nuclear RNA-seq of single neurons reveals molecular signatures of activation," Nature Communications, 7:11022, 13 pages, 2016.
Lake, B.B. et al., "Neuronal subtypes and diversity revealed by single-nucleus RNA sequencing of the human brain," Science, 352(6293):1586-1590, Jun. 24, 2016.
Lalancette-Hebert, M. et al., "Gamma motor neurons survive and exacerbate alpha motor neuron degeneration in ALS," Proc. Natl. Acad. Sci. USA, 113:E8316-E8325, published online Dec. 7, 2016.
Lavado, A. et al., "Prox1 Is Required for Granule Cell Maturation and Intermediate Progenitor Maintenance During Brain Neurogenesis," PLoS Biology, 8(8):e1000460, Aug. 2010.
Lein, E.S. et al., "Genome-wide atlas of gene expression in the adult mouse brain," Nature, 445:168-176, Jan. 11, 2007.
Levison, S.W. and Goldman, J.E., "Both Oligodendrocytes and Astrocytes Develop from Progenitors in the Subventricular Zone of Postnatal Rat Forebrain," Neuron, 10:201-212, Feb. 1993.
Lubeck, E. and Cai, L., "Single-cell systems biology by super-resolution imaging and combinatorial labeling," Nature Methods, 9(7):743-748, Jul. 2012.

(56) References Cited

OTHER PUBLICATIONS

Maricich, S.M. and Herrup, K., "Pax-2 Expression Defines a Subset of GABAergic Interneurons and Their Precursors in the Developing Murine Cerebellum," J. Neurobiol., 41:281-294, 1999.

Marques, S. et al., "Oligodendrocyte heterogeneity in the mouse juvenile and adult central nervous system," Science, 352(6291):1326-1329, Jun. 10, 2016.

Matcovitch-Natan, O. et al., "Mmicroglia development follows a stepwise program to regulate brain homeostasis," Science, 353(6301):aad8670-1-aad8670-12, 789, Aug. 19, 2016.

Miyashita, T. et al., "Neurotrophin-3 Is Involved in the Formation of Apical Dendritic Bundles in Cortical Layer 2 of the Rat," Cerebral Cortex, 20:229-240, Jan. 2010.

\* cited by examiner

Stress/UPR

Chaperonin *groEL*

Protease *clpPC*

Metal uptake

SEQUENCE LISTING

<160> NUMBER OF SEQ ID NOS: 2

<210> SEQ ID NO 1
<211> LENGTH: 129
<212> TYPE: PRT
<213> ORGANISM: Gallus gallus

<400> SEQUENCE: 1

```
Lys Val Phe Gly Arg Cys Glu Leu Ala Ala Ala Met Lys Arg His Gly
1               5                   10                  15

Leu Asp Asn Tyr Arg Gly Tyr Ser Leu Gly Asn Trp Val Cys Ala Ala
                20                  25                  30

Lys Phe Glu Ser Asn Phe Asn Thr Gln Ala Thr Asn Arg Asn Thr Asp
            35                  40                  45

Gly Ser Thr Asp Tyr Gly Ile Leu Gln Ile Asn Ser Arg Trp Trp Cys
        50                  55                  60

Asn Asp Gly Arg Thr Pro Gly Ser Arg Asn Leu Cys Asn Ile Pro Cys
65                  70                  75                  80

Ser Ala Leu Leu Ser Ser Asp Ile Thr Ala Ser Val Asn Cys Ala Lys
                85                  90                  95

Lys Ile Val Ser Asp Gly Asn Gly Met Asn Ala Trp Val Ala Trp Arg
            100                 105                 110

Asn Arg Cys Lys Gly Thr Asp Val Gln Ala Trp Ile Arg Gly Cys Arg
        115                 120                 125

Leu
```

<210> SEQ ID NO 2
<211> LENGTH: 465
<212> TYPE: PRT
<213> ORGANISM: Escherichia coli

<400> SEQUENCE: 2

```
Met Phe Thr Arg Val Ala Asn Phe Cys Arg Lys Val Leu Ser Arg Glu
1               5                   10                  15

Glu Ser Glu Ala Glu Gln Ala Val Ala Arg Pro Gln Val Thr Val Ile
                20                  25                  30

Pro Arg Glu Gln His Ala Ile Ser Arg Lys Asp Ile Ser Glu Asn Ala
            35                  40                  45

Leu Lys Val Met Tyr Arg Leu Asn Lys Ala Gly Tyr Glu Ala Trp Leu
        50                  55                  60

Val Gly Gly Gly Val Arg Asp Leu Leu Leu Gly Lys Lys Pro Lys Asp
65                  70                  75                  80

Phe Asp Val Thr Thr Asn Ala Thr Pro Glu Gln Val Arg Lys Leu Phe
                85                  90                  95

Arg Asn Cys Arg Leu Val Gly Arg Arg Phe Arg Leu Ala His Val Met
            100                 105                 110

Phe Gly Pro Glu Ile Ile Glu Val Ala Thr Phe Arg Gly His His Glu
        115                 120                 125

Gly Asn Val Ser Asp Arg Thr Thr Ser Gln Arg Gly Gln Asn Gly Met
        130                 135                 140

Leu Leu Arg Asp Asn Ile Phe Gly Ser Ile Glu Glu Asp Ala Gln Arg
145                 150                 155                 160

Arg Asp Phe Thr Ile Asn Ser Leu Tyr Tyr Ser Val Ala Asp Phe Thr
                165                 170                 175

Val Arg Asp Tyr Val Gly Gly Met Lys Asp Leu Lys Asp Gly Val Ile
            180                 185                 190
```

```
                    -continued

Arg Leu Ile Gly Asn Pro Glu Thr Arg Tyr Arg Glu Asp Pro Val Arg
        195                 200                 205

Met Leu Arg Ala Val Arg Phe Ala Ala Lys Leu Gly Met Arg Ile Ser
    210                 215                 220

Pro Glu Thr Ala Glu Pro Ile Pro Arg Leu Ala Thr Leu Leu Asn Asp
225                 230                 235                 240

Ile Pro Pro Ala Arg Leu Phe Glu Glu Ser Leu Lys Leu Leu Gln Ala
                245                 250                 255

Gly Tyr Gly Tyr Glu Thr Tyr Lys Leu Leu Cys Glu Tyr His Leu Phe
                260                 265                 270

Gln Pro Leu Phe Pro Thr Ile Thr Arg Tyr Phe Thr Glu Asn Gly Asp
            275                 280                 285

Ser Pro Met Glu Arg Ile Ile Glu Gln Val Leu Lys Asn Thr Asp Thr
    290                 295                 300

Arg Ile His Asn Asp Met Arg Val Asn Pro Ala Phe Leu Phe Ala Ala
305                 310                 315                 320

Met Phe Trp Tyr Pro Leu Leu Glu Thr Ala Gln Lys Ile Ala Gln Glu
                325                 330                 335

Ser Gly Leu Thr Tyr His Asp Ala Phe Ala Leu Ala Met Asn Asp Val
                340                 345                 350

Leu Asp Glu Ala Cys Arg Ser Leu Ala Ile Pro Lys Arg Leu Thr Thr
                355                 360                 365

Leu Thr Arg Asp Ile Trp Gln Leu Gln Leu Arg Met Ser Arg Arg Gln
    370                 375                 380

Gly Lys Arg Ala Trp Lys Leu Leu Glu His Pro Lys Phe Arg Ala Ala
385                 390                 395                 400

Tyr Asp Leu Leu Ala Leu Arg Ala Glu Val Glu Arg Asn Ala Glu Leu
                405                 410                 415

Gln Arg Leu Val Lys Trp Trp Gly Glu Phe Gln Val Ser Ala Pro Pro
                420                 425                 430

Asp Gln Lys Gly Met Leu Asn Glu Leu Asp Glu Glu Pro Ser Pro Arg
            435                 440                 445

Arg Arg Thr Arg Arg Pro Arg Lys Arg Ala Pro Arg Arg Glu Gly Thr
        450                 455                 460

Ala
465
```

METHOD FOR PREPARATION AND HIGH-THROUGHPUT MICROBIAL SINGLE-CELL RNA SEQUENCING OF BACTERIA

CROSS-REFERENCE(S) TO RELATED APPLICATION(S)

This application claims the benefit of U.S. Provisional Application No. 62/941,101, filed Nov. 27, 2019, which is incorporated herein by reference in its entirety.

STATEMENT REGARDING SEQUENCE LISTING

The sequence listing associated with this application is provided in text format in lieu of a paper copy and is hereby incorporated by reference into the specification. The name of the text file containing the sequence listing is 73023-Sequence_List_ST25.txt. The text file is 6 KB; was created on Nov. 20, 2020; and is being submitted via EFS-Web with the filing of the specification.

BACKGROUND

Gene expression in bacteria is highly heterogeneous even in isogenic populations grown under the same lab conditions. Bacteria can randomly differentiate into subpopulations that assume different roles for the survival of the community; a strategy known as bet hedging. For example, gene expression programs governing developmental and stress-response states such as competence or antibiotic resistance may switch on stochastically in a small number of single cells. Population level gene expression measurements are insufficient to resolve such rare states, which, to date, have been characterized only in tractable model systems and through methods such as fluorescence microscopy that can only measure a limited set of reporter genes at a time.

Single-cell RNA-seq (scRNA-seq) methods developed for eukaryotic cells can provide comprehensive gene expression profiles for tens of thousands of cells. Although the need for microbial scRNA-seq has been recognized, technical challenges have prevented adapting scRNA-seq technology to microbes. Specifically, bacteria have low mRNA content, about two orders of magnitude less than human cells and bacterial mRNA is not polyadenylated which makes separation from rRNA challenging. Bacteria have diverse cell walls and membranes which can interfere with the lysis or permeabilization steps required for scRNA-seq. Finally, their small size can hinder microfluidic single-cell isolation.

SUMMARY

The present disclosure provides methods and kits to address these and other related difficulties of working with bacterial cells for scRNA-seq. As discussed further herein, such methods can be referred to, in certain instances, as microSPLiT (Microbial Split-Pool Ligation Transcriptomics).

Accordingly, in an aspect, the present disclosure provides a method of uniquely labeling nucleic acid molecules within a plurality of microbial cells. In an embodiment, the method comprises fixing and permeabilizing the plurality of microbial cells; dissociating microbial cell aggregates within a suspension comprising the plurality of microbial cells; reverse transcribing mRNA within the plurality of microbial cells to provide cDNA; and combinatorially labelling the cDNA to provide labelled cDNA.

In another aspect, the present disclosure provides a kit for labelling nucleic acids within a microbial cell. In an embodiment, the kit comprises a reverse transcriptase enzyme; a cell wall-degradation enzyme; at least one reverse transcription primer comprising a 5' overhang sequence; a plurality of first nucleic acid tags. In an embodiment, each first nucleic acid tag comprises: a first strand comprising a 3' hybridization sequence extending from a 3' end of a first labeling sequence and a 5' hybridization sequence extending from a 5' end of the first labeling sequence, and a second strand comprising an overhang sequence, the overhang sequence comprising (i) a first portion complementary to at least one of the 5' hybridization sequence and the 5' overhang sequence of the reverse transcription primer, and (ii) a second portion complementary to the 3' hybridization sequence; and a plurality of second nucleic acid tags, wherein each second nucleic acid tag comprises: a first strand comprising a 3' hybridization sequence extending from a 3' end of a second labeling sequence and a 5' hybridization sequence extending from a 5' end of the second labeling sequence, and a second strand comprising an overhang sequence, the overhang sequence comprising (i) a first portion complementary to at least one of the 5' hybridization sequence and the 5' overhang sequence of the reverse transcription primer, and (ii) a second portion complementary to the 3' hybridization sequence, wherein the first labeling sequence is different from the second labeling sequence.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of claimed subject matter will become more readily appreciated as the same become better understood by reference to the following detailed description, when taken in conjunction with the accompanying drawings, wherein:

DETAILED DESCRIPTION

The present disclosure generally relates to methods of uniquely labelling or barcoding nucleic acid molecules within a plurality of microbial cells. The present disclosure also relates to kits for uniquely labeling or barcoding a plurality of microbial cells. The molecules to be labelled may include, but are not limited to, RNAs, cDNAs, and/or DNAs.

It will be readily understood that the embodiments, as generally described herein, are exemplary. The following more detailed description of various embodiments is not intended to limit the scope of the present disclosure, but is merely representative of various embodiments. Moreover, the order of the steps or actions of the methods disclosed herein can be changed by those skilled in the art without departing from the scope of the present disclosure. In other words, unless a specific order of steps or actions is required for proper operation of the embodiment, the order or use of specific steps or actions can be modified.

In an aspect, the method comprises fixing and permeabilizing the plurality of microbial cells; dissociating microbial cell aggregates within a suspension comprising the plurality of microbial cells; reverse transcribing mRNA within the plurality of microbial cells to provide cDNA; and combinatorially labelling the cDNA to provide labelled cDNA. In an embodiment, the microbial cells are microbial cells selected from bacteria, archaea, eukaryotes, and combinations thereof. In an embodiment, the microbial cells include bacteria.

Figure 1A:
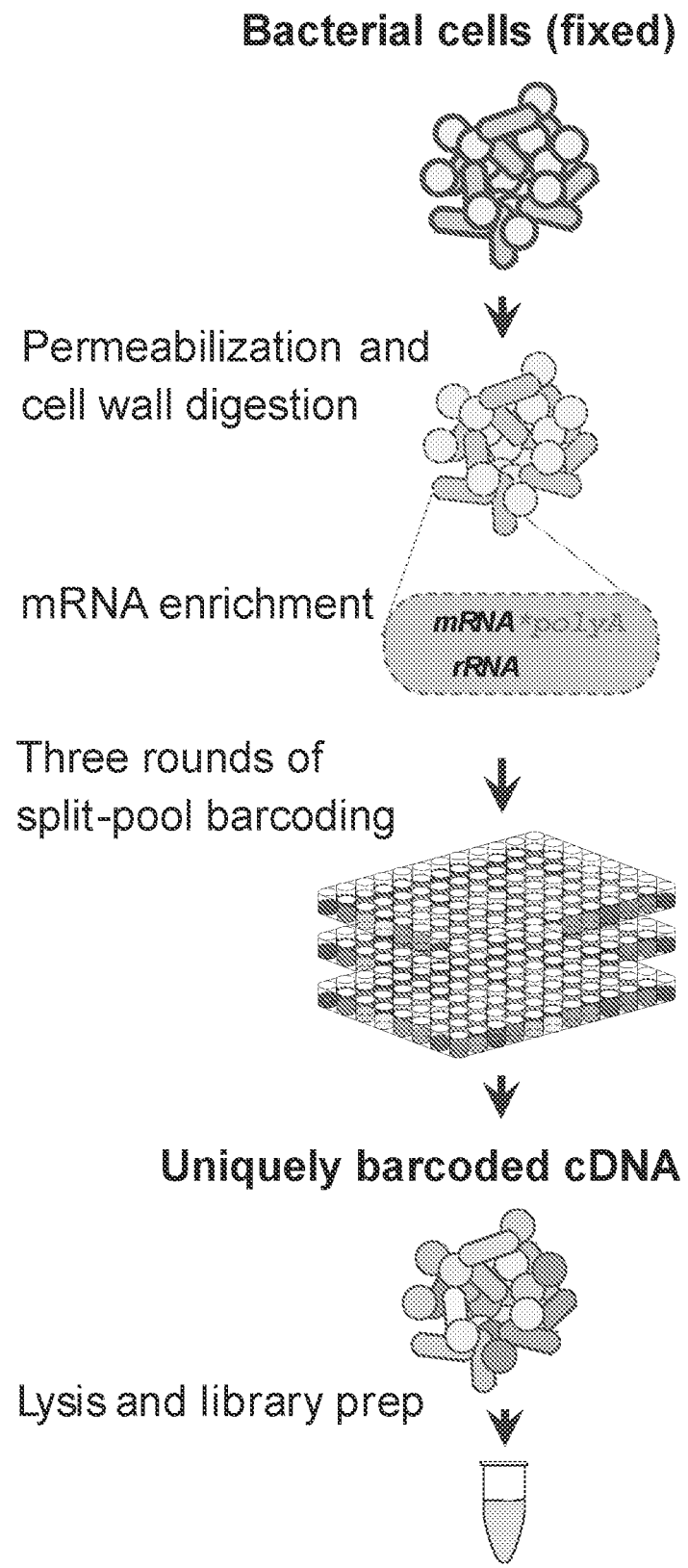
FIG. 1A schematically illustrates a method of uniquely labeling nucleic acid molecules within a plurality of microbial cells, in accordance with an embodiment of the disclosure.

In an embodiment, permeabilizing the plurality of microbial cells comprises fixing the plurality of microbial cells, as shown in FIG. 1A. For example, components of a microbial cell can be fixed or cross-linked such that the components are immobilized or held in place. The plurality of microbial cells can be fixed using formaldehyde in phosphate buffered saline (PBS). The plurality of microbial cells can be fixed, for example, in about 1-4% formaldehyde in PBS. In various embodiments, the plurality of microbial cells can be fixed using methanol (e.g., 100% methanol) at about −20° C. or at about 25° C. In various other embodiments, the plurality of microbial cells can be fixed using methanol (e.g., 100% methanol), at between about −20° C. and about 25° C. In yet various other embodiments, the plurality of microbial cells can be fixed using ethanol (e.g., about 70-100% ethanol) at about −20° C. or at room temperature. In yet various other embodiments, the plurality of microbial cells can be fixed using ethanol (e.g., about 70-100% ethanol) at between about −20° C. and room temperature. In still various other embodiments, the plurality of microbial cells can be fixed using acetic acid, for example, at about −20° C. In still various other embodiments, the plurality of microbial cells can be fixed using acetone, for example, at about −20° C. Other suitable methods of fixing the plurality of microbial cells are also within the scope of this disclosure.

In an embodiment, permeabilizing the plurality of microbial cells comprises contacting the plurality of microbial cells with a detergent. As discussed further herein, such detergents are useful in permeabilizing the plurality of microbial cells, such as to degrade cell walls. In an embodiment, the detergent is selected from the group consisting of Tween 20™, Triton X™, digitonin, maltosides, and combinations thereof. While particular detergents are listed, it will be understood that other detergents are suitable for permeabilizing microbial cells.

In an embodiment, permeabilizing the plurality of microbial cells comprises contacting the plurality of microbial cells with a cell wall-degradation and/or permeabilization enzyme configured to degrade cell walls of the plurality of microbial cells. Such cell wall-degradation enzymes are suitable to degrade cell walls of the plurality of microbial cells, such as by permeating the cells walls or otherwise creating holes within the cell walls of the microbial cells. In an embodiment, degradation does not include fully degrading or removing the cell walls. Rather, such cell wall degradation includes generating holes or perforations in the cell wall, while at least partially retaining the structural integrity of the cell wall such that internal contents of the microbial cell, such as nucleic acid molecules disposed therein, are generally retained within the microbial cell. As discussed further herein, the methods of the present disclosure include barcoding or otherwise labelling nucleic acid molecules within the microbial cells. In this regard, it is important to maintain the integrity of the cell wall to an extent that nucleic acid molecules, such as mRNA, are generally retained within the cell wall upon degrading the cell wall of the plurality of microbial cells. In an embodiment, contacting the plurality of microbial cells with the detergent occurs before contacting the plurality of microbial cells with the cell-wall degradation enzyme.

In an embodiment, the cell-wall degradation enzyme is a lysozyme enzyme. In an embodiment, the lysozyme is according to SEQ ID NO. 1. In an embodiment, the cell-wall degradation enzyme has an amino acid sequence greater than 75%, greater than 85%, greater than 95%, greater than 99%, or more identical to an amino acid of SEQ ID NO. 1. In an embodiment, the cell-wall degradation enzyme comprises or consists of an amino acid sequence at least 76%, 77%, 78%, 79%, 80%, 81%, 82%, 83%, 84%, 85%, 86%, 87%, 88%, 89%, 90%, 91%, 92%, 92%, 93%, 94%, 95%, 96%, 97%, 98%, or 99% identical to an amino acid sequence according to SEQ ID NO: 1.

In an embodiment, the methods of the present disclosure include enriching mRNA within the plurality of microbial cells. As discussed further herein, microbial cells, such as bacterial cells, are generally smaller and contain fewer nucleic acid molecules than, for example, other types of cells, such as those found in multicellular organisms. Accordingly, methods previously performed on non-microbial cells may provide better results, when performed on microbial cells, where mRNA within microbial cells is enriched. In an embodiment, enriching mRNA within the plurality of microbial cells comprises adenylating the mRNA within the plurality of microbial cells. In an embodiment, such adenylation is suitable to couple contacted mRNA with extended and/or repeating adenine residues. As also discussed further herein, such adenylation of mRNA is suitable to generate an increased amount of cDNA when used in conjunction with, for example, polyT reverse transcription primers. In an embodiment, such polyT reverse transcription primers include one or more sequences comprising or consisting of repeating thymine residues. Accordingly, in an embodiment, adenylating the mRNA within the plurality of microbial cells comprises contacting the plurality of microbial cells with an adenylating enzyme to provide adenylated mRNA; and contacting the adenylated mRNA with a polyT reverse transcription primer. In an embodiment, reverse transcribing the mRNA comprises reverse transcribing the adenylated mRNA, such as with a polyT reverse transcription primer.

In an embodiment, the adenylating enzyme is selected from the group consisting of prokaryotic and eukaryotic poly A polymerases including E. coli Poly(A) Polymerase 1 (PAP1). In an embodiment, the PAP1 is according to SEQ ID NO. 2. In an embodiment, the adenylating enzyme has an amino acid sequence greater than 75%, greater than 85%, greater than 95%, greater than 99%, or more identical to an amino acid of an amino acid sequence of SEQ ID NO. 2. In an embodiment, the adenylating enzyme comprises or consists of an amino acid sequence at least 76%, 77%, 78%, 79%, 80%, 81%, 82%, 83%, 84%, 85%, 86%, 87%, 88%, 89%, 90%, 91%, 92%, 92%, 93%, 94%, 95%, 96%, 97%, 98%, or 99% identical to an amino acid sequence according to SEQ ID NO: 2.

In an embodiment, enriching mRNA within the plurality of microbial cells comprises selectively enzymatically degrading RNA molecules within the plurality of microbial cells comprising a 5' monophosphate. Such selective degradation can degrade RNA molecules within the plurality of microbial cells that do not generally include mRNA molecules. In this regard, after selectively enzymatically degrading RNA molecules comprising a 5' monophosphate within the plurality of microbial cells, there is a greater proportion of mRNA within the microbial cells than before selectively enzymatically degrading RNA molecules. As used herein, selectively enzymatically degrading RNA refers to preferentially degrading one type of RNA over another, such as preferentially degrading RNA not including mRNA over mRNA.

In an embodiment, selectively enzymatically degrading RNA molecules within the plurality of microbial cells comprising 5' monophosphate comprises contacting the plurality of microbial cells with a Terminator™ 5' phosphate dependent exonuclease (TEX), such as available from LucigenTM. In an embodiment, selectively enzymatically degrading RNA molecules within the plurality of microbial cells comprising 5' monophosphate comprises contacting the plurality of microbial cells with an exonuclease as described in PCT Application No. PCT/US2012/061978, the contents of which are incorporated herein by reference in their entirety.

As above, the methods of the present disclosure include dissociating microbial cell aggregates within a suspension comprising the plurality of microbial cells. Microbial cells, such as bacterial cells, tend to aggregate without dissociation. Accordingly, if left in an aggregated state, when sequenced, such as after in situ barcoding, sequence data may indicate that barcoded cDNA from many cells in the aggregate originated from a single cell. As discussed further herein, the methods of the present disclosure further include combinatorially labelling cDNA to provide labelled cDNA. If two or more cells are aggregated together, such two or more cells could have labelled cDNA comprising the same barcode sequences, indicating incorrectly that the cDNA from the two or more cells are from a single cell. Accordingly, dissociating the microbial cell aggregates is important for uniquely labelling nucleic acid molecules in each cell of the plurality of microbial cells.

In an embodiment, dissociating the microbial cell aggregates comprises agitating the suspension to provide a disaggregated suspension. Such agitation can be at an intensity and for a time sufficient to disaggregate or otherwise dissociate aggregates of microbial cells, such as can be determined by microscopic methods, dynamic light scattering, or other techniques known in the art. In an embodiment, dissociating the microbial cell aggregates comprises vortexing, sonicating, shaking, or otherwise agitating the plurality of microbial cells, or a combination thereof.

In an embodiment, dissociating the microbial cell aggregates comprises filtering the disaggregated suspension with one or more filters to provide a filtered, disaggregated suspension. Such filtration of disaggregated cells can further ensure that microbial cells are not aggregated, i.e. are in an individual state and not coupled to another cell, and the combinatorially labelled cells are combinatorially labelled individually, rather than as aggregates. In an embodiment, dissociating the microbial cell aggregates includes a combination of agitating and filtering the plurality of microbial cells to remove or reduce microbial cell aggregates.

In an embodiment, dissociating the microbial cell aggregates includes dissociating the microbial cell aggregates before reverse transcribing the mRNA. In an embodiment, the method includes dissociating microbial cell aggregates in a suspension of the plurality of microbial cells after reverse transcribing the mRNA. Cells can tend to get sticky or prone to aggregation during reverse transcription. Accordingly, dissociating the cells after reverse transcription, such as before combinatorially labelling the microbial cells, can be particularly important in uniquely labelling the individual microbial cells.

The methods of the present disclosure include reverse transcribing mRNA within the plurality of microbial cells to provide cDNA. Reverse transcription can be conducted or performed on the plurality of microbial cells. In certain embodiments, reverse transcription can be conducted on a fixed and/or permeabilized plurality of microbial cells. In some embodiments, variants of M-MuLV reverse transcriptase can be used in the reverse transcription. Any suitable method of reverse transcription is within the scope of this disclosure. For example, a reverse transcription mix can include a reverse transcription primer including a 5' overhang and the reverse transcription primer can be configured to initiate reverse transcription and/or to act as a binding sequence for nucleic acid tags. In some other embodiments, a portion of a reverse transcription primer that is configured to bind to RNA and/or initiate reverse transcription may comprise one or more of the following: a random hexamer, a septamer, an octomer, a nonamer, a decamer, a poly(T) stretch of nucleotides, and/or one or more gene specific primers.

In some embodiments, the reverse transcription primer can be configured to reverse transcribe all, or substantially all, RNA in a cell (e.g., a random hexamer with a 5' overhang). In some other embodiments, the reverse transcription primer can be configured to reverse transcribe RNA having a poly(A) tail (e.g., a poly(dT) primer, such as a dT(15) primer, with a 5' overhang). In yet some other embodiments, the reverse transcription primer can be configured to reverse transcribe predetermined RNAs (e.g., a transcript-specific primer). For example, the reverse transcription primer can be configured to barcode specific transcripts such that fewer transcripts can be profiled per cell, but such that each of the transcripts can be profiled over a greater number of cells.

As above, the method of the present disclosure includes combinatorially labelling the cDNA within the plurality of microbial cells. As used herein, "combinatorial labelling" refers to a process in which nucleic acid molecules, such as cDNA molecules, within a cell, such as a microbial cell, are sequentially labelled with a number of nucleic acid tags. As described further herein, by contacting individual cells, and the nucleic acid contents of such cells, of a plurality of microbial cells with a unique sequential combination of nucleic acid tags, the nucleic acid molecules within individual cells can be uniquely labelled. As discussed further herein with respect to the Examples of the present disclosure, such combinatorial labelling is suitable to uniquely identify and profile RNA transcription of single microbial cells in a large population of microbial cells. In this regard, the methods of the present disclosure are suitable to identify RNA transcription of rare cells amongst a large population of more typical or predominant cells, thus, for example, identifying transcription pathways activated in those rare cells.

As above, combinatorial labelling occurs within the microbial cells. Such combinatorial labelling within the cells, i.e. within boundaries of the microbial cell walls, is in contrast to, for example, labelling cDNA outside of the microbial cells walls after lysing the cells. By labelling cDNA within the cells, the cDNA of single microbial may be sequentially labelled with a series of nucleic acid tags using the cell wall as a vessel to carry the cDNA during the labelling process.

In an embodiment, such combinatorial labelling includes dividing the plurality of microbial cells into at least two primary aliquots, the at least two primary aliquots comprising a first primary aliquot and a second primary aliquot; providing primary nucleic acid tags to the at least two primary aliquots, wherein the primary nucleic acid tags provided to the first primary aliquot are different from the primary nucleic acid tags provided to the second primary aliquot; coupling adapter sequences on the cDNA within each of the at least two primary aliquots with the provided primary nucleic acid tags; combining the at least two primary aliquots; dividing the combined primary aliquots into at least two secondary aliquots, the at least two secondary aliquots comprising a first secondary aliquot and a second secondary aliquot; providing secondary nucleic acid tags to the at least two secondary aliquots, wherein the secondary nucleic acid tags provided to the first secondary aliquot are different from the secondary nucleic acid tags provided to the second secondary aliquot; and coupling the primary nucleic acid tags within each of the at least two secondary aliquots with the provided secondary nucleic acid tags.

As above, the methods of the present disclosure include dissociating microbial cell aggregates within a suspension comprising the plurality of microbial cells. In an embodiment, such methods of dissociation include one or more of dissociating microbial cell aggregates in the at least two primary aliquots; and dissociating microbial cell aggregates in the at least two secondary aliquots. In this regard, the microbial cells in the primary aliquot and/or secondary aliquot are dissociated, such as to disaggregate the microbial cells, and microbial cells therein can be uniquely and/or individually labelled with nucleic acid tags. By dissociating aggregates within the primary and secondary aliquots, the methods ensure that microbial cells are contacted individually with nucleic acid tags, rather than in an aggregated form.

In certain embodiments, each nucleic acid tag comprises a first strand including a 3' hybridization sequence extending from a 3' end of a labeling sequence and a 5' hybridization sequence extending from a 5' end of the labeling sequence. In an embodiment, each nucleic acid tag may also comprise a second strand including an overhang sequence. Such a configuration is illustrated in, for example, FIG. 6. The overhang sequence can include (i) a first portion complementary to at least one of the 5' hybridization sequence and the 5' overhang sequence and (ii) a second portion complementary to the 3' hybridization sequence. In some embodiments, the nucleic acid tag (e.g., the final nucleic acid tag) comprises a capture agent such as, but not limited to, a 5' biotin. A cDNA labelled with a 5' biotin-comprising nucleic acid tag allows or permits the attachment or coupling of the cDNA to a streptavidin-coated magnetic bead. In some other embodiments, a plurality of beads can be coated with a capture strand (i.e., a nucleic acid sequence) that is configured to hybridize to a final sequence overhang of a barcode. In yet some other embodiments, cDNA can be purified or isolated by use of a commercially available kit (e.g., an RNEASY™ kit).

In various embodiments, the steps of dividing the plurality of microbial cells, providing primary nucleic acid tags to the at least two primary aliquots, coupling adapter sequences on the cDNA within each of the at least two primary aliquots with the provided primary nucleic acid tags, and combining the at least two primary aliquots can be repeated a number of times sufficient to generate a unique series of labeling sequences for the cDNAs in the plurality of microbial cells. Stated another way, these steps can be repeated a number of times such that the cDNAs in a first cell of the plurality of microbial cells has a first unique series of labeling sequences, the cDNAs in a second cell has a second unique series of labeling sequences, the cDNAs in a third cell has a third unique series of labeling sequences, and so on. In this regard, the methods of the present disclosure provide for the labeling of cDNA sequences from single cells with unique barcodes, wherein the unique barcodes may serve to identify or aid in identifying the cell from which the cDNA originated. In other words, a majority, or substantially all of the cDNA from a single cell may have the same barcode, and that barcode may not be repeated in cDNA originating from one or more other cells in a sample (e.g., from a second cell, a third cell, a fourth cell, etc.).

In certain embodiments, the steps of dividing the plurality of microbial cells, providing primary nucleic acid tags to the at least two primary aliquots, coupling adapter sequences on the cDNA within each of the at least two primary aliquots with the provided primary nucleic acid tags, and combining the at least two primary aliquots are repeated a number of times wherein the number of times is selected from 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, etc. In certain other embodiments, these steps are repeated a sufficient number of times such that the cDNAs of each cell would be likely to be bound to a unique barcode. The number of times can be selected to provide a greater than 50% likelihood, greater than 90% likelihood, greater than 95% likelihood, greater than 99% likelihood, or some other probability that the cDNAs in each cell are bound to a unique barcode. In yet other embodiments, the noted steps are repeated some other suitable number of times.

In some embodiments, barcoded or combinatorially labelled cDNA can be mixed together and sequenced (e.g., using NGS), such that data can be gathered regarding RNA expression at the level of a single microbial cell, such as from an ensemble of microbial cells, all of which may themselves be combinatorially labelled. For example, certain embodiments of the methods of the present disclosure can be useful in assessing, analyzing, or studying the transcriptome (i.e., the different RNA species transcribed from the genome of a given cell) of one or more individual microbial cells.

In this regard, in an embodiment, the methods comprise lysing the plurality of microbial cells (i.e., breaking down the cell structure) to release the cDNAs from within the plurality of microbial cells, for example, after combinatorially labelling the plurality of microbial cells. Accordingly, in an embodiment, the method includes lysing the cells; amplifying the combinatorially labelled cDNA molecules to provide amplicons thereof; and sequencing the amplicons of the combinatorially labelled cDNA molecules. Such amplifying and sequencing steps can be according to any such methods known in the art.

In some embodiments, the plurality of microbial cells is lysed in a lysis solution (e.g., 10 mM Tris-HCl (pH 7.9), 50 mM EDTA (pH 7.9), 0.2 M NaCl, 2.2% SDS, 0.5 mg/ml ANTI-RNase (a protein ribonuclease inhibitor; AMBION®) and 1000 mg/ml proteinase K (AMBION®)), for example, at about 55° C. for about 1-3 hours with shaking (e.g., vigorous shaking). In some other embodiments, the plurality of microbial cells is lysed using ultrasonication and/or by being passed through an 18-25 gauge syringe needle at least once. In yet some other embodiments, the plurality of microbial cells is lysed by being heated to about 70-90° C. For example, the plurality of microbial cells is lysed by being heated to about 70-90° C. for about one or more hours. The cDNAs may then be isolated from the lysed cells. In some embodiments, RNase H can be added to the cDNA to remove RNA.

The methods may further comprise ligating at least two of the nucleic acid tags that are bound to the released cDNAs.

Figure 6:
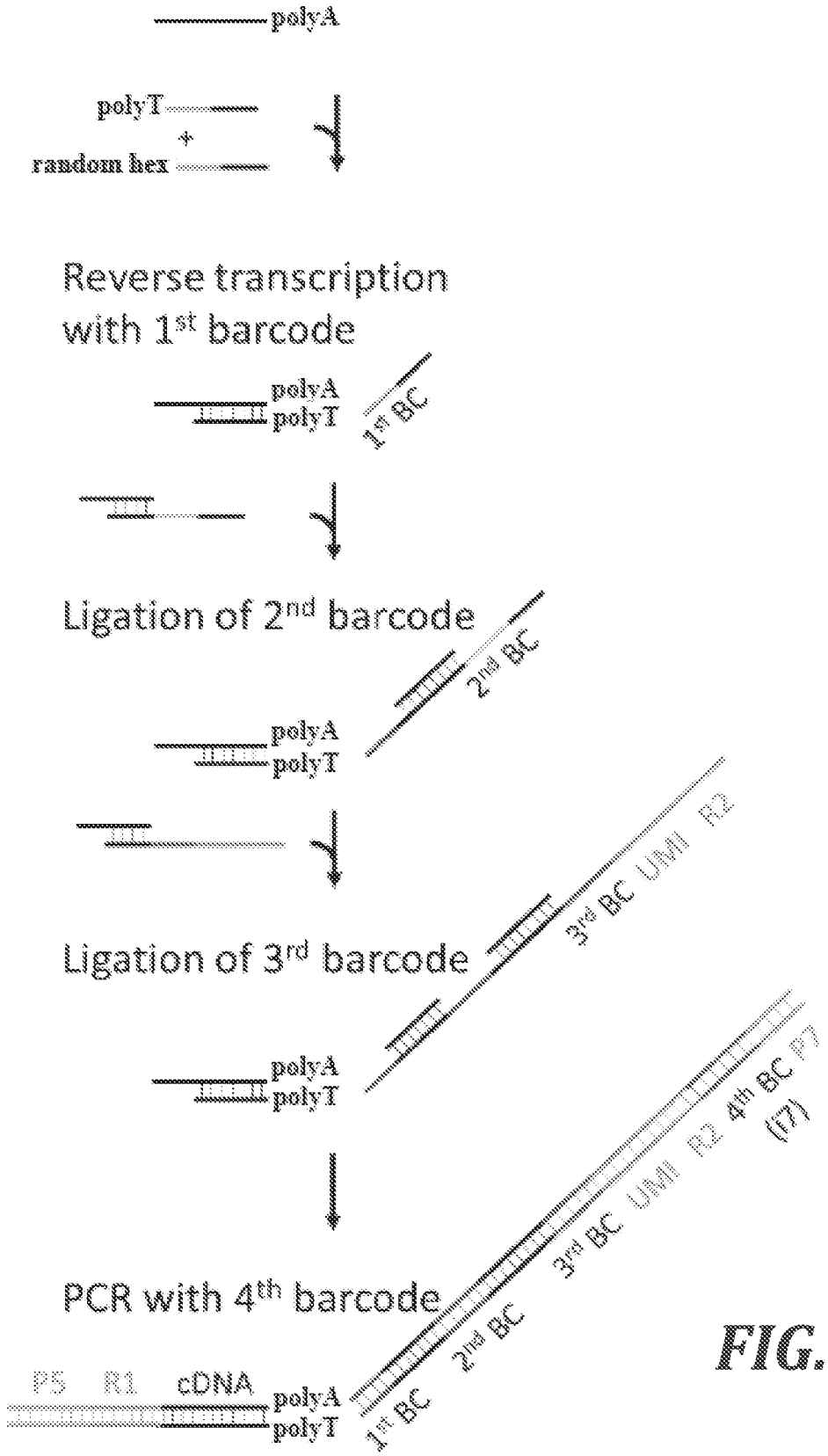
FIG. 6 schematically illustrates a method of uniquely labeling nucleic acid molecules within a plurality of microbial cells, in accordance with an embodiment of the present disclosure.

See, for example, FIG. 6. In some other embodiments, the methods of labeling nucleic acids in the first cell may comprise ligating at least 3, 4, 5, 6, 7, 8, 9, 10, 11, 12, 13, 14, 15, 16, 17, 18, 19, 20, 21, 22, 23, 24, 25, 30, 35, 40, 45, 50, etc. of the nucleic acid tags that are bound to the cDNAs. In an embodiment, coupling the adapter sequences with the primary nucleic acid tags and coupling the primary nucleic acid tags with the secondary nucleic acid tags comprises enzymatically ligating the adapter sequences to the primary nucleic acid tags and enzymatically ligating the primary nucleic acid tags to the secondary nucleic acid tags within the plurality of microbial cells.

As discussed above, an aliquot or group of microbial cells can be separated into different reaction vessels or containers and a first set of nucleic acid tags can be added to the plurality of cDNA transcripts. Vessels or containers can also be referred to herein as receptacles, samples, and wells. Accordingly, the terms vessel, container, receptacle, sample, and well can be used interchangeably herein. The aliquots of microbial cells can then be regrouped, mixed, and separated again and a second set of nucleic acid tags can be added to the first set of nucleic acid tags. In various embodiments, the same nucleic acid tag can be added to more than one aliquot of microbial cells in a single or given round of labeling. However, after repeated rounds of separating, tagging, and re-pooling, the cDNAs of each microbial cell can be bound to a unique combination or sequence of nucleic acid tags that form a barcode. In some embodiments, microbial cells in a single sample can be separated into a number of different reaction vessels. For example, the number of reaction vessels may include four 1.5 ml microcentrifuge tubes, a plurality of wells of a 96-well plate, or another suitable number and type of reaction vessels.

In another aspect, the present disclosure provides a kit for labelling nucleic acids within a microbial cell. In an embodiment, the kit comprises a reverse transcriptase enzyme; a cell wall-degradation enzyme; at least one reverse transcription primer comprising a 5' overhang sequence; a plurality of first nucleic acid tags. In an embodiment, first nucleic acid tags of the plurality of first nucleic acid tags comprise: a first strand comprising a 3' hybridization sequence extending from a 3' end of a first labeling sequence and a 5' hybridization sequence extending from a 5' end of the first labeling sequence, and a second strand comprising an overhang sequence, the overhang sequence comprising (i) a first portion complementary to at least one of the 5' hybridization sequence and the 5' overhang sequence of the reverse transcription primer, and (ii) a second portion complementary to the 3' hybridization sequence; and a plurality of second nucleic acid tags, wherein each second nucleic acid tag comprises: a first strand comprising a 3' hybridization sequence extending from a 3' end of a second labeling sequence and a 5' hybridization sequence extending from a 5' end of the second labeling sequence, and a second strand comprising an overhang sequence, the overhang sequence comprising (i) a first portion complementary to at least one of the 5' hybridization sequence and the 5' overhang sequence of the reverse transcription primer, and (ii) a second portion complementary to the 3' hybridization sequence, wherein the first labeling sequence is different from the second labeling sequence.

The kit may further comprise a plurality of second nucleic acid tags. Each second nucleic acid tag may comprise a first strand. The first strand may include a 3' hybridization sequence extending from a 3' end of a second labeling sequence and a 5' hybridization sequence extending from a 5' end of the second labeling sequence. Each second nucleic acid tag may further comprise a second strand. The second strand may comprise an overhang sequence, wherein the overhang sequence may comprise (i) a first portion complementary to at least one of the 5' hybridization sequence and the 5' overhang sequence of the reverse transcription primer and (ii) a second portion complementary to the 3' hybridization sequence. In some embodiments, the first labeling sequence can be different from the second labeling sequence.

In some embodiments, the kit may also comprise one or more additional pluralities of nucleic acid tags. Each nucleic acid tag of the one or more additional pluralities of nucleic acid tags may comprise a first strand. The first strand may include a 3' hybridization sequence extending from a 3' end of a labeling sequence and a 5' hybridization sequence extending from a 5' end of the labeling sequence. Each nucleic acid tag of the one or more additional pluralities of nucleic acid tags may also comprise a second strand. The second strand may include an overhang sequence, wherein the overhang sequence comprises (i) a first portion complementary to at least one of the 5' hybridization sequence and the 5' overhang sequence of the reverse transcription primer and (ii) a second portion complementary to the 3' hybridization sequence. In some embodiments, the labeling sequence can be different in each given additional plurality of nucleic acid tags.

In an embodiment, each of the nucleic acid tags comprises: a first strand comprising: a barcode sequence comprising a 3' end and a 5' end; and a 3' hybridization sequence and a 5' hybridization sequence flanking the 3' end and the 5' end of the barcode sequence, respectively; and a second strand comprising: a first portion complementary to at least one of the 5' hybridization sequence and the adapter sequence; and a second portion complementary to the 3' hybridization sequence.

In an embodiment, the adenylating enzyme is selected from the group consisting of prokaryotic and eukaryotic poly A polymerases including E. coli Poly(A) Polymerase 1 (PAP1). In an embodiment, the PAP1 is according to SEQ ID NO. 2. In an embodiment, the adenylating enzyme has an amino acid sequence greater than 75%, greater than 85%, greater than 95%, greater than 99%, or more identical to an amino acid of an amino acid sequence of SEQ ID NO. 2. In an embodiment, the adenylating enzyme comprises or consists of an amino acid sequence at least 76%, 77%, 78%, 79%, 80%, 81%, 82%, 83%, 84%, 85%, 86%, 87%, 88%, 89%, 90%, 91%, 92%, 92%, 93%, 94%, 95%, 96%, 97%, 98%, or 99% identical to an amino acid sequence according to SEQ ID NO: 2.

In an embodiment, the cell-wall degradation enzyme is a lysozyme enzyme. In an embodiment, the lysozyme is according to SEQ ID NO. 1. In an embodiment, the cell-wall degradation enzyme has an amino acid sequence greater than 75%, greater than 85%, greater than 95%, greater than 99%, or more identical to an amino acid of SEQ ID NO. 1. In an embodiment, the cell-wall degradation enzyme comprises or consists of an amino acid sequence at least 76%, 77%, 78%, 79%, 80%, 81%, 82%, 83%, 84%, 85%, 86%, 87%, 88%, 89%, 90%, 91%, 92%, 92%, 93%, 94%, 95%, 96%, 97%, 98%, or 99% identical to an amino acid sequence according to SEQ ID NO: 1.

In an embodiment, the kit further comprises a 5' phosphate dependent exonuclease, such as a Terminator™ 5' phosphate dependent exonuclease (TEX), such as available from Lucigen™. As described further herein, a 5' phosphate dependent exonuclease is suitable to selectively enzymatically degrading RNA molecules within the plurality of microbial cells comprising 5' monophosphate. In an embodiment, the exonuclease is an exonuclease as described in PCT Application No. PCT/US2012/061978, the contents of which are incorporated herein by reference in their entirety.

In various embodiments, the kit may further comprise at least one of a reverse transcriptase, a fixation agent, a permeabilization agent, a ligation agent, and/or a lysis agent. In certain embodiments, the kit further comprises additional reagents for performing one or more methods of the present disclosure, such as a buffer, dNTPs, containers for aliquots, and the like.

As will be understood by one of ordinary skill in the art, each embodiment disclosed herein can comprise, consist essentially of, or consist of its particular stated element, step, ingredient, or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components, and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e., denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context.

Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Definitions and explanations used in the present disclosure are meant and intended to be controlling in any future construction unless clearly and unambiguously modified in the following examples or when application of the meaning renders any construction meaningless or essentially meaningless in cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

The term "binding" is used broadly throughout this disclosure to refer to any form of attaching or coupling two or more components, entities, or objects. For example, two or more components can be bound to each other via chemical bonds, covalent bonds, ionic bonds, hydrogen bonds, electrostatic forces, Watson-Crick hybridization, etc.

EXAMPLES

Example 1

Experimental Methods

Purification of cDNA cDNA purification and bonding to streptavidin beads was performed according to the SPLiT-seq protocol. See, for example, A. B. Rosenberg, C. M. Roco, R. A. Muscat, A. Kuchina, P. Sample, Z. Yao, L. Gray, D. J. Peeler, S. Mukherjee, W. Chen, S. H. Pun, D. L. Sellers, B. Tasic, G. Seelig, Single-cell profiling of the developing mouse brain and spinal cord with split-pool barcoding. Science, eaam8999 (2018).

Template Switch

Streptavidin beads with bound cDNA molecules were resuspended in a solution containing 99 μl nuclease-free water, 44 μL of 5X Maxima RT buffer (ThermoFisher), 33 μL of 50% PEG8000 solution, 22 μL of 10 mM dNTPs each (ThermoFisher), 5.5 μL of RNase Inhibitor (Enzymatics), 11 μL of Maxima H Minus Reverse Transcriptase (ThermoFisher), and 5.5 μL of 100uM of a template switch primer (BC_0127). The template switch primer contains two ribonucleic guanines followed by a locked nucleic acid guanine at the end of the primer (Exiqon). The beads were incubated at room temperature for 30 minutes and then at 42° C. for 90 minutes with gentle shaking.

PCR

The on-beads PCR followed by the qPCR to amplify the product were performed according to the SPLiT-seq protocol. A. B. Rosenberg, C. M. Roco, R. A. Muscat, A. Kuchina, P. Sample, Z. Yao, L. Gray, D. J. Peeler, S. Mukherjee, W. Chen, S. H. Pun, D. L. Sellers, B. Tasic, G. Seelig, Single-cell profiling of the developing mouse brain and spinal cord with split-pool barcoding. Science, eaam8999 (2018).

Illumina Sequencing

Libraries were sequenced on MiSeq or NextSeq systems (Illumina) using 150 nucleotide (nt) kits and paired-end sequencing. Read 1 (74 nt) covered the transcript sequences. Read 2 (86 nt) covered the UMI and barcode combinations. The index read (6 nt), serving as the fourth barcode, covered the sublibrary indices introduced after fragmentation.

Fragmentation

Following cDNA amplification, molecules were fragmented with a subsequent adaptor ligation step using a protocol modified from Enzymatics. Briefly, 110 ng of amplified cDNA was placed into a 50 uL reaction containing 5 uL of 10× Fragmentation Buffer (Enzymatics) and 10 uL of 5X WGS Fragmentation Mix (Enzymatics). Samples were placed into a thermocycler with the following steps: 32 C for 10 min, 65 C for 30 min, 4 C hold. Following fragmentation, a double sided SPRI bead size selection with bounds of 0.6x-0.8x was performed, with the final elution step using a volume of 50 uL. This 50 uL of eluant was placed into a 100 uL reaction containing 20 uL of 5X Rapid Ligation Buffer (Enzymatics), 10 uL of WGS Ligase (Enzymatics), and 2.5 uL of a pre-annealed adaptor duplex consisting of BC_243 and BC_244 at a concentration of 100 uM in 50uM NaCl. This adaptor ligation mix was incubated at 20 C for 15 minutes. This was followed by a 0.8x SPRI size selection with final elution in 20 uL. Next, 18.5 uL of eluant was placed into a 50 uL qPCR reaction containing 25 uL of 2X Kapa HiFi Master Mix, 2.5 uL of 20X Evagreen, 2 uL of BC 0027 (10 uM), and 2 uL of BC_0076-BC_0083 (10 uM). This PCR mix was placed in a thermocycler with following conditions: 95 C for 3 minutes, beginning cycling of 98 C for 20 s, 67 C for 20 s, and 72 C for 3 min. Cycles were allowed to continue on a qPCR machine until reaction neared saturation, as denoted by the exit of exponential phase in amplification. Finally, samples were incubated at 72 C for 5 min once sufficient cycling occurred. After this reaction, a double-sided SPRI size selection was performed with bounds of 0.5x-0.7x, where resulting 20 uL eluant was a sequencing-ready library.

Construction of Reporter Strains

IolA promoter was defined as 448 bp sequence upstream of the iolA gene including binding sites for CcpA, SigA, and IolR. IolR promoter was defined as 422 bp sequence upstream of iolR gene including binding sites for SigA and IolR. Optimized RBS+linker (AAGGAGGAAAGTCA-CATT) and codon-optimized YFP or CFP for best expression in low-GC gram-positive organisms were used. Two terminators (CGTCGGGCGGAT-TACTCGCCCGAAAAAA and CAAAACGAAAGGCCCAGTCTTTCGACT-GAGCCTCG) were added at the 3' end of $P_{iolA}$-YFP and $P_{iolR}$-CFP constructs which were obtained as gBlocks (Integrated DNA Technologies). $P_{iolA}$-YFP gBlock was amplified with MS0009 and MS0010, while $P_{iolR}$-CFP gBlock was amplified with MS0012 and MS0010. Amplicons were used in a 2-part Gibson assembly (NEB cat. E2611L) with the EcoRI-HF (NEB cat. R3101S) digested plasmid pDG1730 (accession number U46199, BGSCID ECE115) designed for integration into the amyE locus.

iolT homologous region for native integration was defined as bases 332-1419 of the iolT coding sequence, excluding the first 331 bp and the stop codon. iolT homologous region was amplified from B. subtilis PY79 gDNA template using primers MS0044 and MS0045, adding a B. subtilis codon optimized (Integrated DNA Technologies Codon Optimization Tool) 3xGS linker to the 3' end (GGCTCAGGGTCAGGTAGC). mScarlet-I sequence was amplified from pEB2-mScarlet-I (Addgene cat. 104007) template with primers MS0046 and MS0047 adding the 3xGS linker to the 5' end. A two terminator (CGTCGGGCG-GATTACTCGCCCGAAAAAA and CAAAACGAAAGGCCCAGTCTTTCGACT-GAGCCTCG) sequence was amplified from $P_{iolA}$-YFP gBlock template using primers MS0048 and MS0049. Amplicons were used in a 4-part Gibson assembly (NEB cat. E2611L) with the HindIII-HF (NEB cat. R3104S) and NdeI (NEB cat. R0111S) digested plasmid pBGSC6 (accession number DQ483056, BGSCID ECE22) designed for native integration.

The assembled plasmid was transformed into B. subtilis PY79. In short, 5 mL of transformation media (25g/L $K_2HPO_4.3H_2O$, 6 g/L $KH_2PO_4$, 1 g/L trisodium citrate, 0.2 g/L $MgSO_4.7H_2O$, 2 g/L $Na_2SO_4$ (pH 7.0), 50 µM $FeCl_3$, 2 µM $MnSO_4$, 0.4% glucose, 0.2% glutamate) was inoculated with one colony and incubated at 37 C with shaking until reaching OD 0.5. About 1 µg of pDG1730-$P_{iolA}$-YFP, pDG1730-$P_{iolR}$-CFP or pBGSC6-iolT-mScarlet-I plasmids was then added to 1 mL of OD 0.5 culture and incubated at 37 C with shaking for 40 minutes. Then, 1 mL of 2xYT media (16 g/L tryptone, 10 g/L yeast extract, 5 g/L NaCl) was added and the mixture was incubated at 37 C with shaking for 45 minutes. 100 µL of mixture was spread onto LB plate with spectinomycin (100 ng/µL) or chloramphenicol (5 ng/µL), and left to grow overnight at 37 C. Integration was confirmed by Sanger sequencing (Genewiz).

Fluorescence Microscopy and Flow Cytometry

Overnight cultures of B. subtilis PY79 strains AmyE:: $P_{iolA}$-YFP, AmyE::$P_{iolR}$-CFP, and IolT-mScarlet-I were grown in either 1.25x LB Lennox (Sigma-Aldrich), M9+0.02% casamino acids+0.5% glucose or M9+0.02% casamino acids+0.5% myo-inositol (Sigma-Aldrich) before inoculation into respective fresh media (LB at 1:100 and M9+0.02% casamino acids+0.5% glucose or 0.5% myo-inositol at 1:50). All cultures were grown at 37 C with shaking. LB cultures were sampled at OD 0.7, 2.0, and 4.0, while M9 cultures were sampled at OD0.5. Samples from all strains were imaged and only AmyE::$P_{iolA}$-YFP sample was measured by flow cytometry. Samples for imaging were fixed in 4% formaldehyde for 10 minutes on ice, quenched with 100 mM Tris pH 7.0, and resuspended in PBS, while samples for flow cytometry were resuspended in PBS. Imaging samples were spotted on 1% low-melting agarose M9 pads, placed into a 35 mm coverslip-bottom dish (Ibidi, cat. 81156) and imaged with Leica DMI6000 inverted microscope at 100× (University of Washington—W. M. Keck Microscopy Center). Flow cytometry was performed on the BD Accuri C6. Cytometry data were analyzed using the Bioconductor R packages flowCore and flowViz. A rectangular gate was established using the forward and side scatter data from the M9 inositol controls with log(coordinates) on forward and side scatter of (10.5,2), (13,2), (13, 12), (10.5, 12). This gate was applied to all subsequent cytometry data analysis. Fluorescence measurements are shown as density histograms for each OD or media conditions.

Bacterial Culture

*Escherichia coli* MW1255, a derivative of MG1655, and *Bacillus subtilis* PY79 overnight cultures were inoculated into fresh 1.25× LB Lennox medium (Sigma-Aldrich) at 1:1000 or 1:250, respectively, and grown at 37 C with shaking (200 rpm). For the heat shock experiment, upon reaching the $OD_{600}$=0.5, half of each culture was transferred to the separate 37° C. incubator where the temperature was increased to 47° C., and kept there with shaking (200 rpm) for 8 minutes from the time the temperature stabilized. Both control and heat-treated samples then were immediately centrifuged at 4° C., 5000 rcf for 5 minutes, and resuspended in cold formaldehyde. Since we found a cluster in these data that may represent an artifact of the cold centrifugation conditions, the *B. subtilis* growth curve samples were instead centrifuged at room temperature, 10,000 rpm for 1 minute before fixation.

Fixation and Permeabilization

For the steps below, centrifugation was performed at 4° C., 5000 rcf for 5 minutes. Following centrifugation, the bacterial pellet was resuspended in 1mL of fresh, cold, 4% formaldehyde solution (in 1× PBS) and incubated at 4° C. overnight. The next morning, cells were centrifuged and resuspended in 1 ml cold 100 mM Tris-HCL+RI ('RI' indicates that SUPERase-In RNase Inhibitor, ThermoFisher, was added to a final concentration of 0.1 U/uL). Cells were centrifuged and resuspended in 250 ul of 0.04% Tween-20 in 1× PBS, then permeabilized for 3 min on ice. We then added 1ml of cold PBS+RI, centrifuged the cells and resuspended in 200 ul lysozyme mix per sample on ice as follows: 0.1M Tris-HCL pH7, 0.05M EDTA, 2.5 mg/ml lysozyme, 0.25U/ml SUPERase-In. We incubated the samples at 37 C in the thermocycler for 15 minutes as we found that precise timing of lysozyme incubation is critical to maintaining cell integrity at later stages of the protocol. Following the cell wall digestion step, we immediately added 1ml of cold PBS+RI, centrifuged the cells and counted the cells stained with SYTO9 using Accuri C6 flow cytometer. For the species-mixing experiment, we mixed the *E. coli* and *B. subtilis* cells at equal proportions and took 0.6M cells for each of heat shocked and control samples. For the *B. subtilis* growth curve experiments, we took 0.25M cells for each OD sample.

In-Cell Polyadenylation

In order to enrich for mRNA capture, we performed in situ polyadenylation with *E. coli* Poly(A) Polymerase I (PAP) from NEB. For 0.25M cell samples, the reaction proceeded in 50 μl volume, and in 100 μl volume for the 0.6M cell samples. For each 0.6M cells bacterial pellet, we added 66 μl of water, 4 μl of SUPERase-In, 10 μl of 10× PAP Buffer, 10 μl of 10 mM ATP, and 10 μl of PAP. The reaction mixture was incubated at 37 C for 30 min, then centrifuged upon addition of 1 ml cold PBS+RI. We also added 1 μL of 10% Tween-20 in order to make the cells easier to pellet. The cells then were resuspended in 0.5 ml of cold PBS+RI.

Reducing Aggregate Formation

Two steps were crucial to break down cell aggregates and reduce the doublet rate: first, we vortexed and double-filtered the bacterial cells prior to reverse transcription; and second, we performed sonication with double filtration right after the reverse transcription.

Following the polyadenylation step, cells in 500 ul of PBS-RI were vortexed for 1 minute on the highest setting, filtered through 10 μm pluriStrainer (pluriSelect) by pipetting through the membrane, then filtered again through 1 μm pluri Strainer with gentle suction, and finally, right before adding to the reverse transcription wells, vortexed again on the highest setting for 1 minute.

Following the reverse transcription step and after resuspension in 2 mL of cold PBS+RI, cells were vortexed for 1 minute on the highest setting, filtered through 10 μm and 1 μm pluriStrainer as above, and briefly sonicated at 10% power for 5s on ice for 1 pulse (Sharpertek Ultrasonic Cell Crusher) followed by immediate distribution to the ligation plate. We found that the sonication step can be replaced by a second vigorous vortexing step, with the roughly 2-fold increase in resulting detected doublet rate (0.7% to 1.3%).

In-Cell Reverse Transcription

Like in SPLiT-seq, the first round of barcoding occurs through an in situ reverse transcription (RT) reaction. Cells are split into up to 48 wells, each containing barcoded well-specific reverse transcription primers. We used both random hexamer and anchored poly$(dT)_{15}$ barcoded RT primers in each well at the ratio of 1:2 (2.5 μM random hexamer+5 μM poly$(dT)_{15}$). In addition to primers, each RT well had a mix of 1× RT Buffer, 0.25U/μL RNase Inhibitor (Enzymatics), 0.25U/μL SUPERase-In RNase Inhibitor, 500 μM dNTPs each (ThermoFisher), 7.5% of PEG8000, 20U/μL of Maxima H Minus Reverse Transcriptase (ThermoFisher). We pipetted 4 μL of cells at about 1M cells per mL in PBS-RI into every well, in the total resulting RT reaction volume of 20 ul. The plate was incubated in a thermocycler for 10 min at 23° C. followed by 50° C. for 50 min. RT reactions were pooled back together and after adding 9.6 μL of 10% Triton X-100, cells were centrifuged for 5 min at 3000 g at 4° C. in a swinging bucket rotor centrifuge. The supernatant was removed and cells were resuspended in 2 mL of cold 1× PBS-RI. The cells then underwent two rounds of filtration and sonication as described above.

In-Cell Ligations

The oligonucleotide plates for the second and third barcoding round were prepared as previously described. See A. B. Rosenberg, et al., Single-cell profiling of the developing mouse brain and spinal cord with split-pool barcoding. *Science*, eaam8999 (2018). We prepared a 2.04 mL ligation mix containing 727.5 μL of RNase-free water, 500 μL 10× T4 Ligase buffer (NEB), 20 μL T4 DNA Ligase (2000 U/μL, NEB), 30 μL RNase inhibitor (40 U/μL, Enzymatics), 12.5 μL Superaseln RNase Inhibitor (20 U/μL), and 750 μL of 50% PEG8000. This ligation mix and the 2 mL of sonicated and filtered cells in 1× PBS were added to a basin and mixed thoroughly to make a total of 4.04 mL. The ligation steps were performed as in the SPLiT-seq protocol, except we did vigorous vortexing combined with the double filtration technique as described above where the protocol called for a filtration step.

Lysis and Sub-Library Generation

After the third round of barcoding, we performed a final vigorous vortexing and double filtration step as described above. Then 70 μL of 10% Triton-X100 was added to the cell solution before spinning it down for 5 min at 3000 G and 4° C. We carefully aspirated the supernatant, leaving about 30 μL to avoid removing the pellet. We then resuspended the cells in 4 mL of wash buffer (4 mL of 1× PBS, 40 μL of 10% Triton X-100 and 10 μL of SUPERase-In RNase Inhibitor) and spun down for 5 min at 3000 G and 4° C. We then aspirated the supernatant and resuspended in 50 μL of PBS+RI. After counting cells, we aliquoted them into sub-libraries (in 1.7 mL tubes). After adding the desired number of cells to each sublibrary, we brought the volume of each to 50 µL by adding 1× PBS and froze the cells at −80 C overnight. Next morning, we flash-thawed the cells and added 50 µL of 2× lysis buffer (20 mM Tris (pH 8.0), 400 mM NaCl, 100 mM EDTA (pH 8.0), and 4.4% SDS) and 10 µL of proteinase K solution (20 mg/mL). We incubated cells at 55° C. for 2 hours with shaking at 200 rpm to lyse the cells and reverse the formaldehyde crosslinks.

Example 2

Computational Methods Alignment and Generation of Cell-Gene Matrices

We chose to use the parent strain *B. subtilis* 168 genome since the respective annotation file had more features including ncRNA and provided gene names, which the PY79 strain annotation file lacked. However, we note that using PY79 genome and annotation (ASM49748v1.44) and MG1655 genome and annotation (ASM584v2) did not significantly affect the number of detected genes or the findings.

The data preprocessing and alignment was performed using a modified SPLiT-seq pipeline, where the cDNA reads were mapped to either a combined *B. subtilis-E. coli* genome (ASM904v1.45 and ASM80076v1.37 from EnsemblBacteria) or only the *B. subtilis* 168 genome (ASM904v1.45 from EnsemblBacteria) using STAR with the splicing isoform detection switched off. In addition, we kept the highest-scored multimapping reads, assigning a fractional count based on the number of equally good alignments, since bacterial genomes are known to contain overlapping CDSs. We then generated a matrix of gene counts for each cell (N×K matrix, with N cells and K genes).

Processing of Data From the Heat Shock Experiment

We applied standard Scanpy normalization and scaling, dimensionality reduction, and clustering as described in the Scanpy tutorial and below, using 9 PCA components and 45 neighbors for computing the neighborhood graph of cells. For plotting the heat map of the top 6 enriched genes for the heat shock experiment clusters, we additionally filtered the genes by keeping only the genes expressed in at least 40% of the cluster, with a minimum fold change of 2 and in at most 30% of the rest of the data. For making the half-volcano plots of enriched genes in the *E. coli* heat shock cluster, for better clarity we omitted the outlier norR gene with a very high fold change but low significance.

Clustering and data analysis for the species-mixing experiment with heat shock treatment was performed using Scanpy. We only kept transcriptomes with the number of total reads higher than 200. Then, we removed the ribosomal and tRNA reads from the data, retaining only reads representing the mRNA counts for both species. We further filtered cells based on the mRNA counts, retaining cells expressing >100 reads and >100 genes, and additionally filtered the genes retaining the genes expressed in >5 cells. We then applied standard Scanpy normalization and scaling, dimensionality reduction, and clustering as described in the Scanpy tutorial. The clusters were produced by Louvain graph-clustering method and manually inspected for the top differentially expressed genes. After inspection, three pairs of transcriptionally similar clusters with fewer differentially expressed genes were merged, resulting in clusters 1, 2 and 3 in FIG. 1D.

Processing of *B. subtilis* Data from the Growth in Rich Media Experiment

We chose to omit the high variance gene selection since the number of genes we detected (on the order of 3,000) was much lower than what is typically detected for mammalian cells and permitted analysis without confining the gene set. In addition, restriction to high variance genes did not result in a major change in the final clustering output. We followed with standard Scanpy normalization and scaling, dimensionality reduction, and clustering. Briefly, we computed the neighborhood graph of cells using the top 16 PCA components of the data matrix (n-neighbors=8). We then used Louvain graph-clustering method to produce the global clustering of the data. For the two-dimensional embedding of the data, we chose to use the t-distributed Stochastic Neighbor Embedding (t-SNE) using a scikit-learn implementation of the Barnes-Hut t-SNE algorithm. Top enriched genes for each cluster were computed by Wilcoxon rank-sum test with Benjamin-Hochberg correction.

Clustering and data analysis for the combined 10 samples of B.S. grown in rich medium was performed using Scanpy and verified with Seurat v3 and UNCURL. Experiment 1 sampled OD points 0.5, 1.0, 1.7, 2.0, 2.8, and 3.2, while in experiment 2 we collected OD points 0.5, 1.0, 1.3, 1.7, 2.8, 3.5, 5.3, and 6.0. For the data from both experiments separately, we discarded any transcriptomes with the number of total reads fewer than 200. Then, we filtered the data and retained only reads representing the mRNA counts (excluding the ribosomal and tRNA reads). Finally, we combined the data matrices together. Since the read depth decreased for the higher OD samples, for selecting the highest quality data, we implemented differential thresholds for each OD in the combined matrix, retaining top 75% of the cells by read counts for each OD sample. This resulted in retention of 25,214 transcriptomes from both experiments. Finally, we performed batch correction through Scanpy, using a python implementation of ComBat. Cells that passed the QC were clustered using a pipeline described in previous studies.

Sub-Clustering of the Late OD Samples

For finding the finer grain structure within the late OD point data, we took filtered read matrices from cells belonging to OD 5.3 and 6.0 groups and re-run the processing pipeline as described above. Because of the smaller numbers of cells, we chose to use the UMAP algorithm to embed the data.

Calculation of Sigma Factors and Transcriptional Regulators Activity

To generate the profiles of activities of sigma factors and transcriptional regulators (TR), we used the SubtiWiki resource. For the TR analysis, each regulon was divided into "positive" and "negative" subregulons based on the mode of regulation (we omitted the rare more complex interactions and focused on the more straightforward transcriptional activation or repression), and we then calculated the average expression of genes within each subregulon for each cluster.

Example 3

Microsplit Generates High-Quality Single-Cell RNA-Seq Data

Figure 1B:
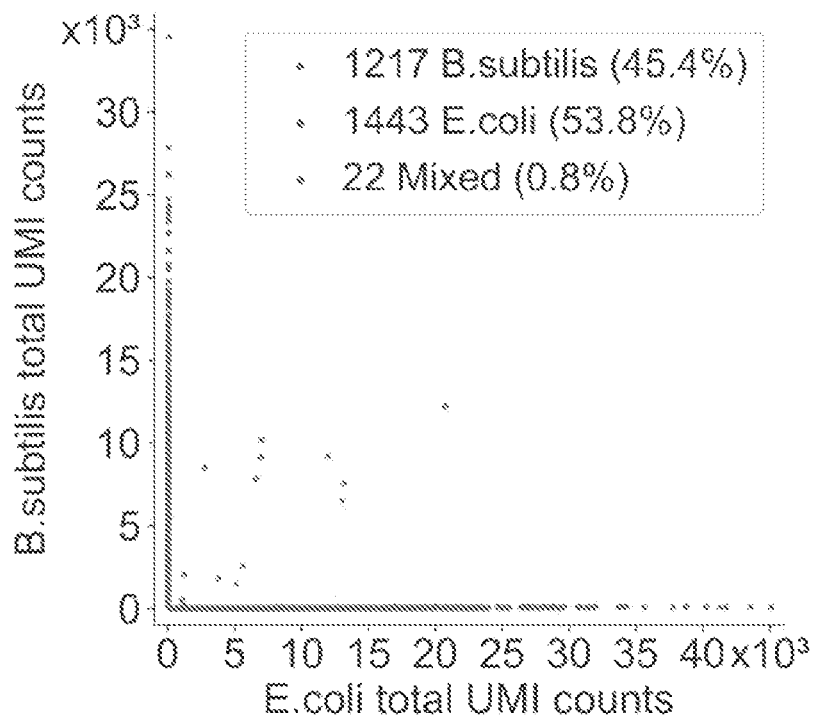
FIG. 1B is a barnyard plot for the *E. coli* and *B. subtilis* species-mixing experiment, wherein each dot corresponds to a putative single-cell transcriptome and total UMI (unique molecular identifier) counts for all types of RNA are plotted, in accordance with an embodiment of the disclosure.
Figure 1C:
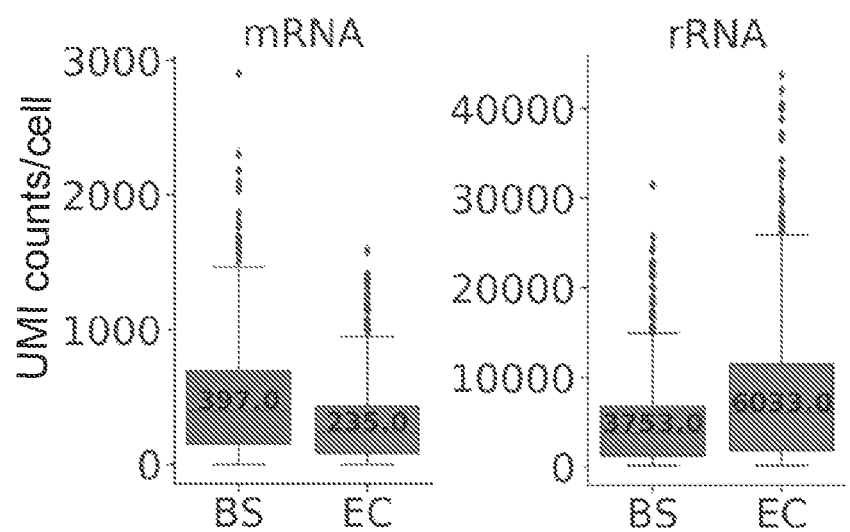
FIG. 1C illustrates mRNA and rRNA UMI counts per cell for both species, in accordance with an embodiment of the disclosure, where error bars represent 95% confidence intervals.

In order to validate microSPLiT performance on a mixture of gram-positive and gram-negative organisms, we grew *E. coli* MW1255 and *B. subtilis* PY79 cells to $OD_{600}$=0.5 and subjected half of each culture to a brief 47° C. heat-shock. We performed a microSPLiT experiment on both samples, using the first barcode as a sample identifier. We prepared and sequenced a cDNA library from 2682 total bacteria from heat-shocked and control treatments and aligned the reads to a combined *B. subtilis E. coli* genome. 99.2% of the putative single cell transcriptomes were unambiguously assigned to a single species (FIG. 1B). The rest is attributed to multi-species cellular aggregates, with true aggregate frequency including same-species aggregates expected to be double the multi-species one (1.6%). We sampled a median of 235 mRNA transcripts per cell for *E. coli* and 397 for *B. subtilis* (FIG. 1C), or approximately 5-10% of the estimated total mRNA, and 3.7% and 9.5% of all detected RNA molecules per cell for each respective species. We also detected a median count of 3753 and 6033 rRNA per cell for *B. subtilis* and *E. coli* (FIG. 1C) as well as a median number of 18 and 20 tRNA molecules per cell. We observed 230 median unique genes per cell for *B. subtilis* and 138 for *E. coli*. The majority of detected genes for both species had on average between 0 and 5 UMIs per gene. The summed *E. coli* expression data was correlated with independently published bulk transcriptomic data (r=0.736). The most highly expressed genes detected only in the bulk assay but not with microSPLiT encode tRNA species. When we discarded multiply aligned reads, the proportion of mRNA reads increased to 90.5% for *B. subtilis* and 28.2% for *E. coli*, while mRNA UMI counts per cell were not strongly affected.

Even with in-cell polyadenylation, the majority of rRNA and mRNA molecules were captured by random hexamer primers, while tRNA were predominantly retrieved by poly-T primers. The mRNA and rRNA UMI counts in each cell were highly correlated (r=0.97 and 0.94), as were UMI counts of each detected mRNA captured by poly-T and random hexamer primers (r=0.87 and 0.94). tRNA UMI counts captured by poly-T and random hexamer primers displayed lower correlation which could be due to the transient native polyadenylation of some tRNA species. We found that the 23S and 16S rRNA abundances were highly correlated with each other, while correlation with 5S rRNA was lower. We also quantified the effect of sequencing depth on gene and UMI detection by subsampling analysis, suggesting that additional sequencing would only modestly increase UMI counts.

Figure 1D:
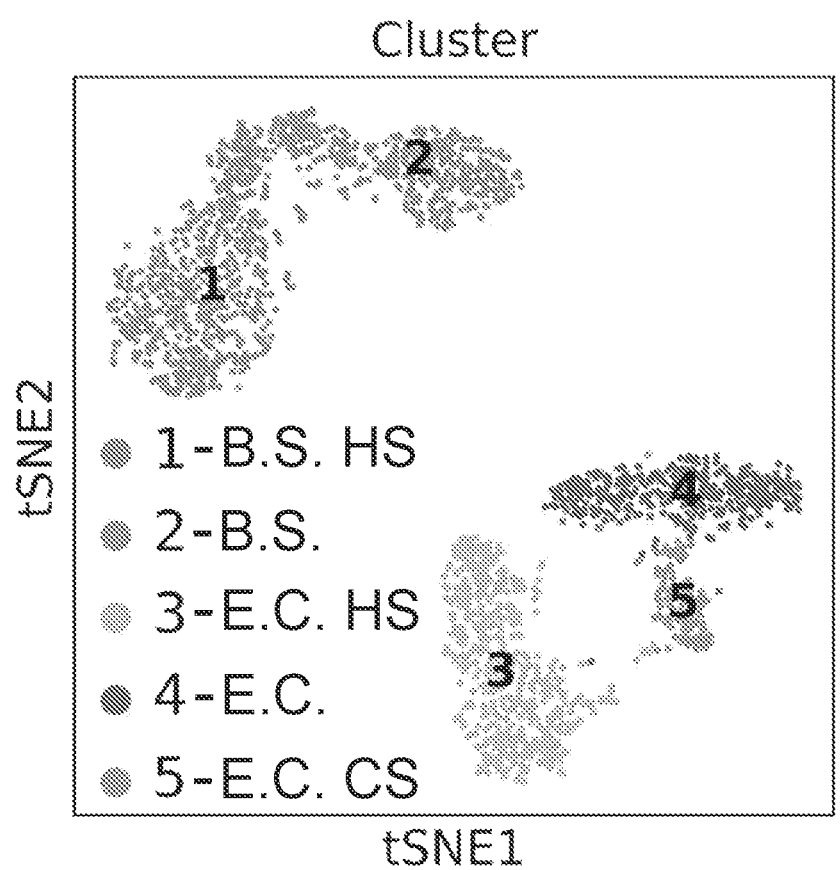
FIG. 1D illustrates t-stochastic neighbor embedding (t-SNE) of data from heat shock experiments showing distinct clusters, "HS" (heat shock), and "CS" (cold shock), in accordance with an embodiment of the present disclosure.

Next, we tested whether microSPLiT could detect transcriptional responses to heat shock. Unsupervised clustering identified five distinct clusters which were visualized by t-distributed stochastic neighbor embedding (t-SNE) (FIG. 1D). The first barcode identified two pairs of clusters corresponding to the heat treated and control cultures, and gene expression analysis within each pair further labelled them as corresponding to *B. subtilis* and *E. coli* cells. Enriched within each heat shock cluster were classical heat shock genes differentially expressed in each of the *E. coli* and *B. subtilis* heat treated clusters as compared to the control clusters.

Unexpectedly, we found an additional small cluster, representing *E. coli* cells from both control and heat-treated samples that expressed a different signature of DEAD-box helicase deaD induction as well as cold shock genes cspA-G, consistent with a transcriptional response to cold. This subpopulation of *E. coli* might be displaying a very rapid response to cold from a brief cold centrifugation step performed as the first step in sample preparation before formaldehyde fixation and is thus likely an artifact of the workflow.

Example 4

Transcriptional Patterns During *B. subtilis* Growth in Rich Medium

Figure 2A:
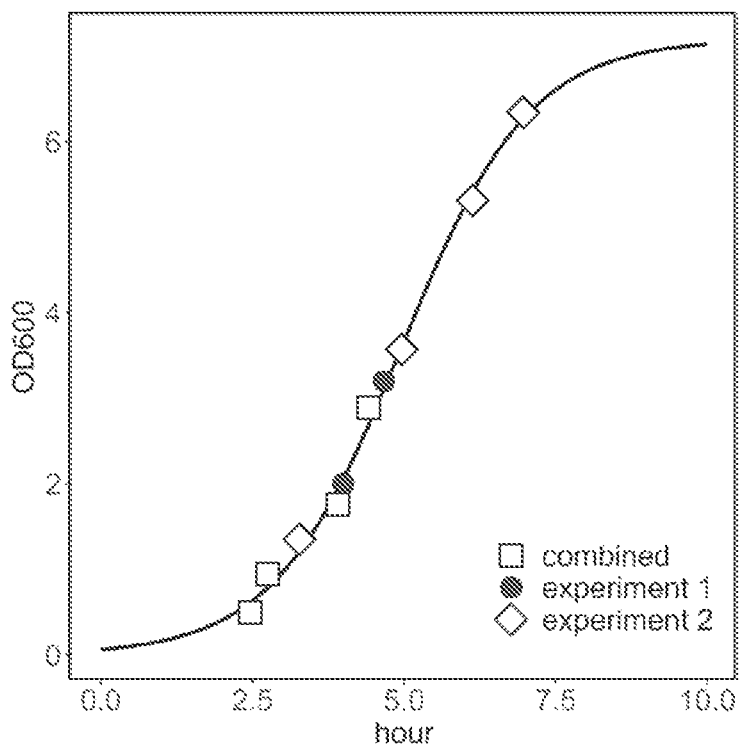
FIG. 2A illustrates optical density (OD) points sampled in two experiments overlaid on the growth curve from a second experiment, in accordance with an embodiment of the present disclosure.

Next, we applied microSPLiT to capture transcriptional states across the *B. subtilis* growth curve in a rich medium (LB). In total, we sampled ten optical density (OD) points along the growth curve of the laboratory strain PY79 ranging from OD0.5 (early exponential phase) to OD6.0 (early stationary phase), with one replicate of 4 OD points (FIG. 2A). We retained all optical density measurements, however, the time data from the first experiment was not recorded. We fit the growth curve in FIG. 2A to the time-stamped OD samples from the second experiment using the formula for a sigmoidal curve: $L/(1+\exp(-k(t-t0)))$. To plot the OD points from the first experiment, we set the fit to the recorded OD curve and solved for time.

Figure 2B:
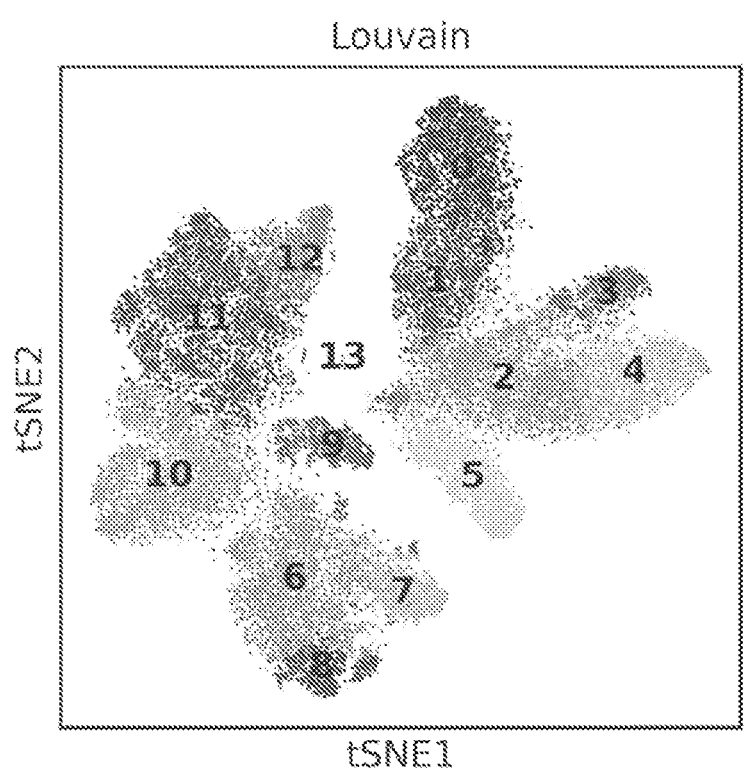
FIG. 2B illustrates t-SNE embedding of the combined growth curve data shaded by cluster OD, in accordance with an embodiment of the present disclosure.
Figure 2C:
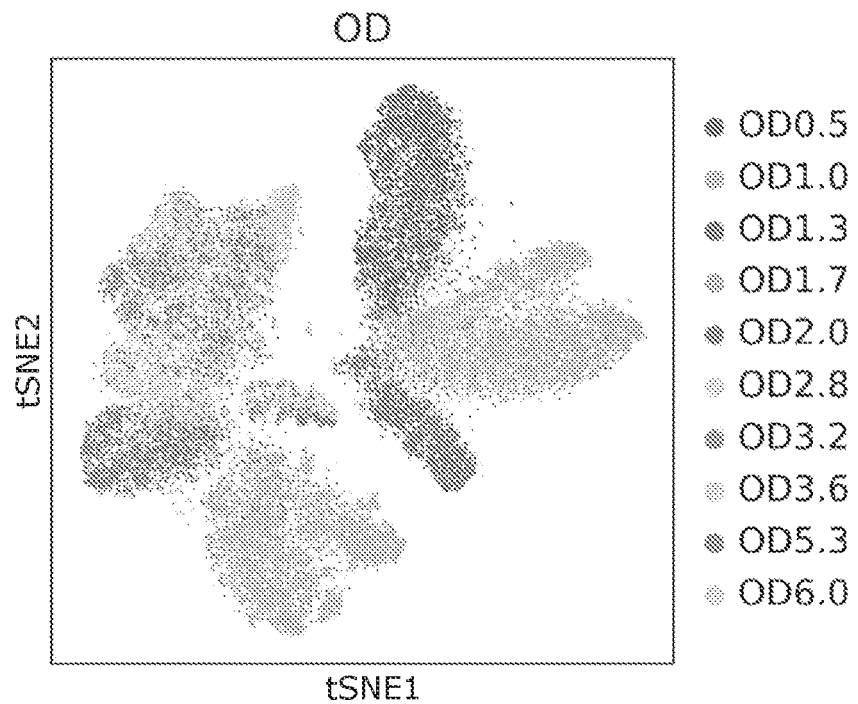
FIG. 2C illustrates t-SNE embedding of the combined growth curve data shaded by cluster OD, in accordance with an embodiment of the present disclosure.

The first barcode was used to record sample identity (i.e. OD) and the replicates are consistent and produced a combined dataset of 25,214 cells (FIGS. 2B and 2C).

Unsupervised clustering of the combined datasets revealed 14 clusters (FIG. 2B), most of which overlapped with a single OD (FIG. 2C). The most notable exceptions are two smaller clusters that contain cells from multiple ODs: cluster 9 with cells from OD2-3.2 that differentially express myo-inositol metabolism pathway genes, and a very small cluster 13 containing only 36 cells from 5 different OD points uniquely expressing genes associated with the defective PBSX prophage (FIG. 2B).

Figure 2D:
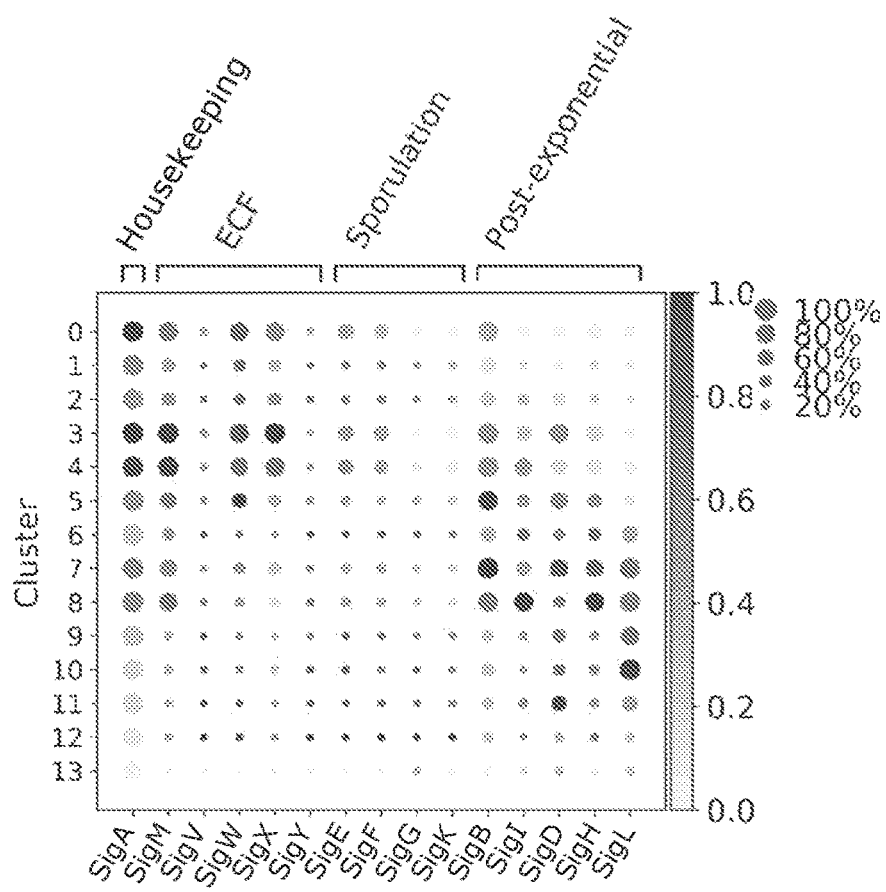
FIG. 2D illustrates inferred normalized sigma factor activity for each cluster, calculated from averaged expression of genes regulated by each sigma factor, where a size of each dot indicates the proportion of cells in the cluster in which the sigma factor is active, while the shade indicates the average activity normalized from 0 to 1 across all clusters for each sigma factor, in accordance with an embodiment of the present disclosure.

We then turned to an analysis of alternative sigma factors which are the primary regulators of prokaryotic RNA polymerase specificity and thus directly shape transcriptional changes in response to environmental conditions. To understand whether microSPLiT could capture variation in sigma factor utilization across different growth stages, we averaged expression of genes regulated by each sigma factor, recording for each cluster, both the percentage of cells expressing at least one gene regulated by a given sigma factor and the average intensity of gene expression (FIG. 2D). The patterns of sigma factor utilization are largely consistent with the literature, with housekeeping $\sigma^A$ activity highest at the early growth stage relative to other time points, and the activity of general stress response sigma factor $\sigma^B$ rising as cells begin to exit from exponential phase (clusters 3-4, OD1.3-1.7) and then declining as cells approach stationary phase (FIG. 2D). Sporulation sigma factors were more active at later ODs, but in a small fraction of cells (clusters 10-12, FIG. 2D) and the extracellular function (ECF) sigma factors were divided into two groups with different patterns of activities (FIG. 2D). Additionally, correlations between the sigma factor regulons largely agreed with the concept of molecular time sharing, i.e. the idea that sigma factors compete for RNA polymerases.

Figure 2E:
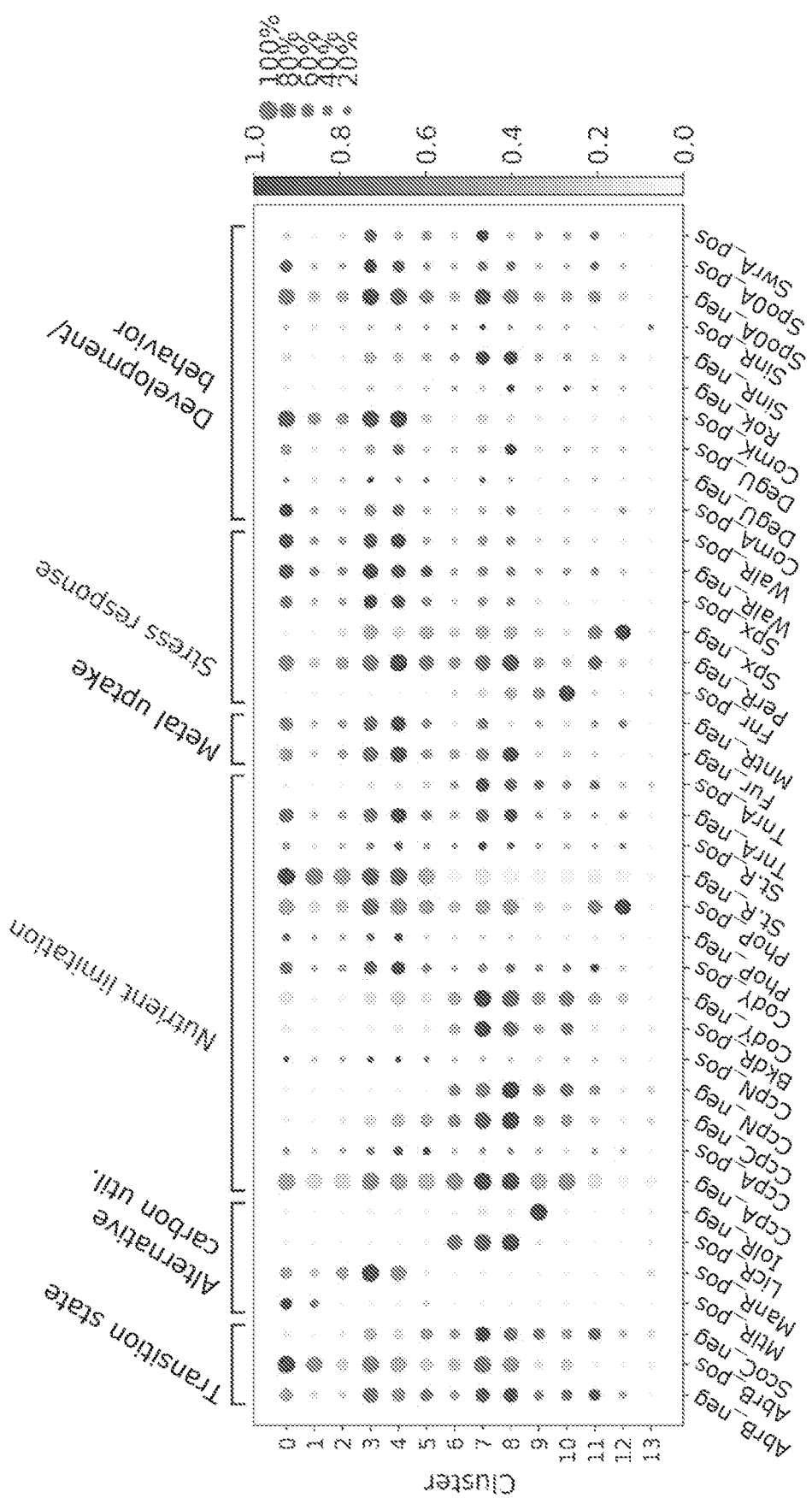
FIG. 2E illustrates inferred activity of select transcriptional regulators per cluster, calculated and normalized for all clusters as above, plotted as in FIG. 2D, where "neg" indicates that activity was calculated for the genes known to be negatively regulated by this TR, and "pos" indicates the activity was calculated for the genes positively regulated by the given TR, in accordance with an embodiment of the present disclosure.

To obtain an even finer-grained picture, we inferred the activity profiles of select transcriptional regulators from expression of the genes in their respective regulons (FIG. 2E). This revealed changes in regulation of carbon utilization, stress responses, metal uptake, developmental decisions and more (FIG. 2E). For example, we observe cellular response to a variety of intrinsic and cell-envelope stresses, as well as temporal activation patterns of a battery of developmental regulators (FIG. 2E). These data indicate that microSPLiT captures known regulatory programs and reveals heterogeneity in a wide range of cellular pathways.

We observe that the housekeeping $\sigma^A$ activity is highest at OD0.5 (cluster 0), while the activity of general stress response sigma factor $\sigma^B$ rises as cells begin to exit from exponential phase (clusters 3-4, OD1.3-1.7) and then declines as cells approach stationary (FIG. 2D). Sporulation sigma factors $\sigma^F$, $\sigma^G$ and $\sigma^K$ were induced at later ODs; but in a small fraction of cells (clusters 10-12, FIG. 2D). This is consistent with the heterogeneous initiation of sporulation. The extracellular function (ECF) sigma factors $\sigma^M$, $\sigma^W$ and σ$^X$ implicated in maintaining cell envelope function reached maximal activity at OD 1.0 in a large proportion of cells (clusters 3-4, FIG. 2D), consistent their basal activity in logarithmic phase in non-stressed cells. Meanwhile, the remaining ECF sigma factors σ$^V$, raising defenses against lytic endoglycosidases, and σ$^Y$ increased in activity towards later OD points were observed in a small subpopulation of cells (clusters 10-12, FIG. 2D), similar to the sporulation sigma factors. σ$^I$ and σ$^H$ activities, regulating heat response and post-exponential behavior respectively, peak in cluster 8 which represents a subgroup of cells at OD 1.7 (FIGS. 2B and 2D). In contrast, σ$^B$ and σ$^D$ regulating general stress response and motility are most active in cluster 7, a second distinct subgroup of OD 1.7 cells (FIGS. 2B and 2D). Finally, σ$^L$, implicated in utilization of arginine, acetoin and fructose as well as regulation of the cold shock response, peaks in cells at OD 2-2.8 represented in cluster 10 (FIGS. 2B and 2D), likely due to the highly enriched acetoin utilization genes in this cluster. Additionally, correlations between the sigma factor regulons largely agreed with the concept of molecular time sharing, i.e. the idea that sigma factors compete for RNA polymerases.

The activity of genes negatively regulated by the main transition state regulator AbrB is increased after OD1.0 (clusters 3-4) compared to the activity of genes positively regulated by AbrB, indicating that the preferred carbon sources, such as glucose, begin to be depleted (FIG. 2E). Toward the intermediate growth stages, the cells sense carbon, nitrogen and phosphate limitations: clusters 7 and 8 (OD 1.7) display a change in carbon metabolism indicated by the expression of genes repressed by the carbon catabolite control proteins (FIG. 2E). Similarly, the regulator of nitrogen assimilation TnrA becomes activated at OD1.7 (clusters 7-8), while PhoP, regulating the phosphate metabolism, becomes active at three different growth stages: OD1.0, OD1.7 and later on at OD6.0 (clusters 3-4, 7-8 and 12, FIG. 2E). In addition, cells respond to metal deficiency, switching off the negative regulators of iron and manganese uptake Fur and MntR after OD1.0 (clusters 3-4, FIG. 2E).

Surprisingly, we also observe an upregulation of ComK-regulated genes in a high proportion of cells in the early ODs which is not consistent with the primary role of this transcription factor in a rare developmental state of competence (FIG. 2E). This observation could be explained by the fact that a large cohort of ComK-induced genes are involved in metabolism and DNA repair and can be activated by other regulators.

Example 5

Figure 3A:
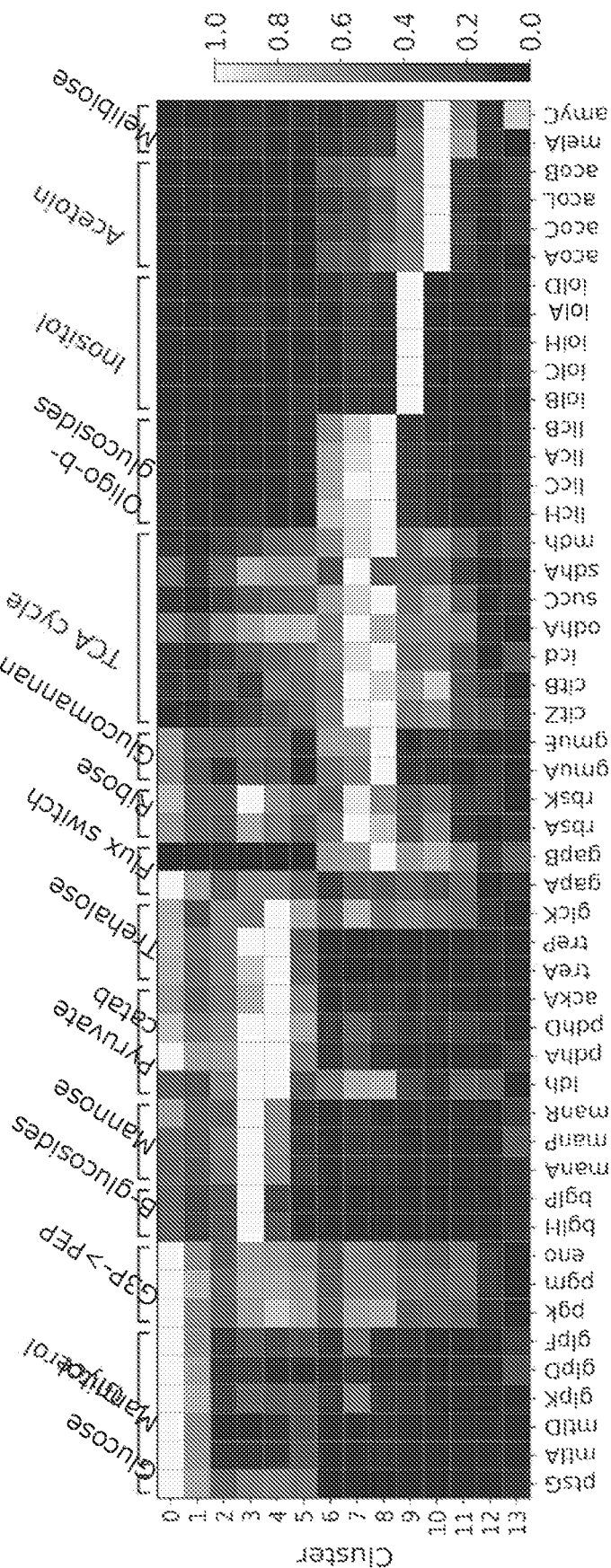
FIG. 3A illustrated normalized expression of genes from select metabolic pathways and central carbon metabolism during B. subtilis growth shown per cluster, where gene expression shows distinct carbon utilization programs associated with different clusters and growth states, in accordance with an embodiment of the present disclosure.

Central Carbon Metabolism Changes and Transient Activation of Alternative Carbon Utilization Pathways Given the changes in regulation of carbon utilization observed in our analysis of transcriptional regulators, we turned to a more comprehensive examination of carbon metabolism genes enriched in each cluster (FIG. 3A). When glucose and other preferred sugars are present, they are converted to pyruvate during glycolysis; the primary metabolic route when these sugars are abundant. In these conditions promoting rapid growth, pyruvate is then converted to lactate, acetate, acetoin, and other by-products through fermentation. Upon depletion of preferred sugars, cells redirect the fermentation by-products to be metabolized in the TCA cycle generating additional adenosine triphosphate (ATP) and carbon dioxide.

Figure 3B:
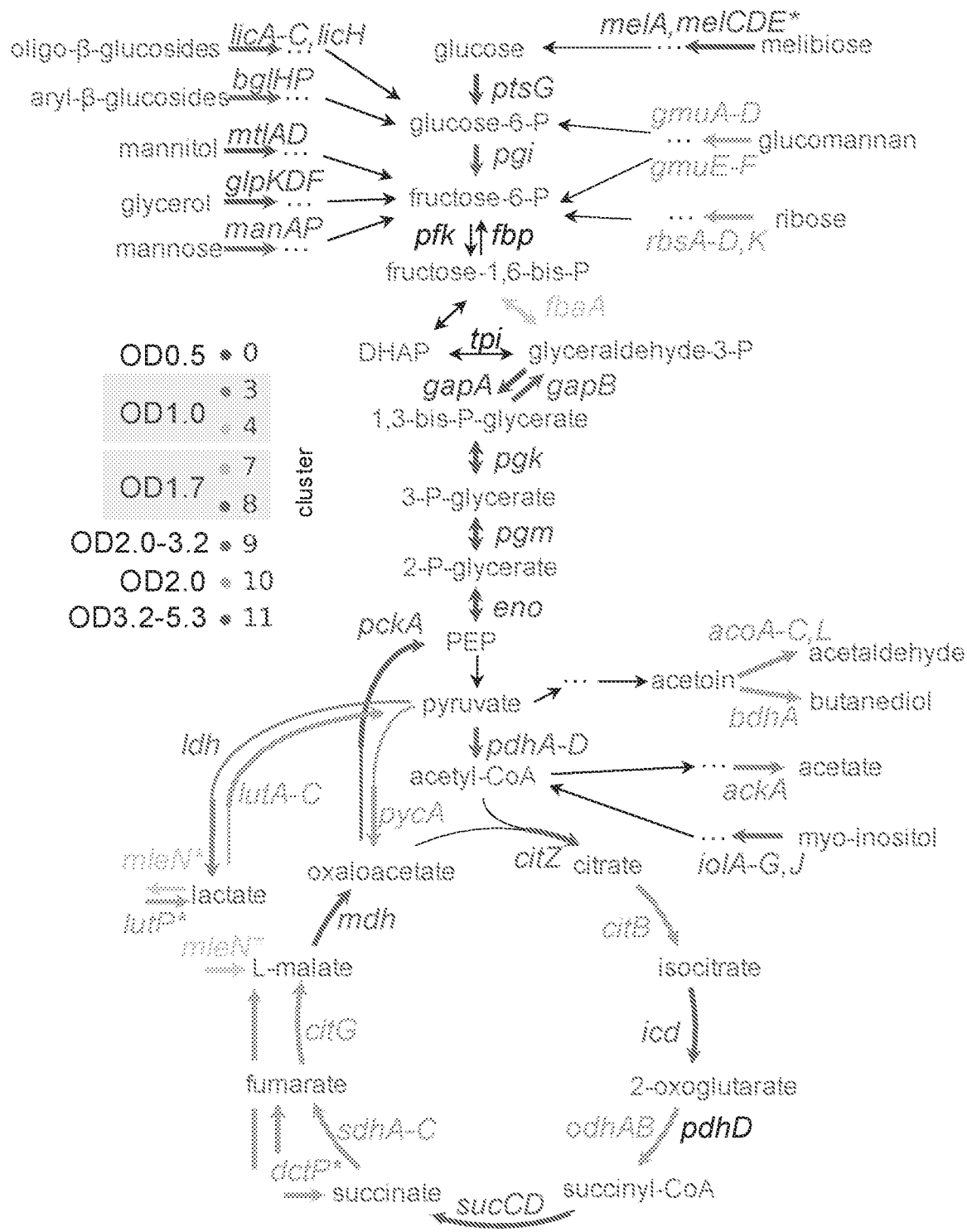
FIG. 3B schematically illustrates the central carbon metabolism pathway of B subtilis showing alternative carbon sources, metabolic products and genes in the pathway, in accordance with an embodiment of the disclosure.
Figure 3C:
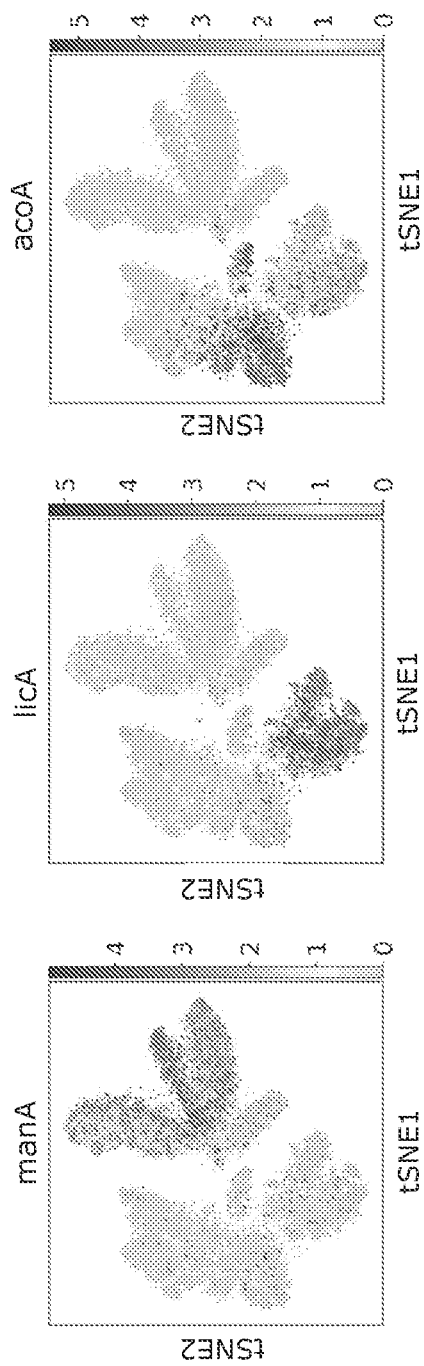
FIG. 3C illustrates expression of select genes from FIG. 3A overlaid on the t-SNE plot to illustrate the differential patterns of activation, in accordance with an embodiment of the present disclosure.

As expected, in the clusters corresponding to early ODs (clusters 0-4) we observe peak expression of genes involved in glycolysis such as glucose permease (ptsG), and genes involved in rapid growth and fermentation such as lactate dehydrogenase (ldh), pyruvate dehydrogenase (pdhA) and acetate kinase (ackA) (FIGS. 3A and 3B). At OD1.7 cells appear to undergo a dramatic transition from glycolysis to gluconeogenesis with multiple genes from the gluconeogenetic pathway activated in clusters 7 and 8 (FIGS. 3A-3C). We also find a different pattern of pyruvate production and utilization, together with catabolism of acetoin, another fermentation product, and additional nutrient fluxes into the TCA cycle (FIGS. 3A-3C).

Additionally, we observe expression of pathways responsible for uptake and utilization of different carbon sources. As the preferred sources of carbon are depleted, the major repressor of alternative carbon utilization pathways CcpA becomes inactive, permitting the cells to catabolize a variety of carbohydrates (FIGS. 3A-3C). We find that the activation and suppression of these pathways happen in varying proportions of the cells in each OD sample and appear to follow a temporal order (FIGS. 3A-3C).

In the exponential phase (clusters 0 and 1, OD0.5), as expected, we find high expression of ptsG, a glucose permease which transports and phosphorylates glucose. The enzymes in the gapA operon constituting the metabolic pathway from glyceraldehyde-3P to phosphoenolpyruvate (PEP) were also upregulated in cluster 0 (FIGS. 3A and 3B).

At OD0.5 we observe increased expression of mtlA-D and glpK,D,F genes responsible for utilization of mannitol and glycerol, respectively (FIGS. 3A and 3B). Cells in clusters 3 and 4 (OD1.0) activate catabolism of mannose and aryl-β-glucosides (manA,P and bglH,P, FIGS. 3A and 3B). In cluster 7 (OD1.7) we observe the upregulation of genes for utilization of glucomannan (gmuA-F) and the ribose transporter (rbsA-D) (FIGS. 3A and 3B). Finally, at even later ODs three additional alternative carbon source utilization programs switch on. Cluster 9 comprising cells from ODs 1.7, 2.0, 2.8, and 3.2 is defined by the expression of genes implicated in the most common stereoisomer of inositol, myo-inositol catabolism (iolA through iolJ, further "iolAJ" operon), while cluster 10 (OD2.0) is enriched for genes responsible for utilization of acetoin (acoABCL, FIG. 3A and 3B). Finally, cluster 11, representing a range of ODs from 3.2 to 5.3, differentially expresses genes for melibiose utilization (melA, melCDE, FIGS. 3A and 3B).

Next, in clusters 3 and 4 (OD1.0) we observe transcriptional patterns suggesting an increase in flux from pyruvate either being converted to lactate by ldh which is then exported via a malate antiporter mleN or converted to acetate via intermediates by pdhAD and ackA (FIG. 3A and 3B). These observations are consistent with transient medium acidification via acetate production during rapid fermentative *B. subtilis* growth.

In cluster 7, in contrast to clusters 3 and 4, instead of excretion we now observe uptake of lactate via lutP and conversion to pyruvate by lutAC. The conversion of pyruvate to oxaloacetate is also upregulated by increased expression of pycA. In addition, acetoin, a product of acetate metabolism, in this cluster is actively converted into butanediol by action of bdhA. Cells in this cluster also express more dctP implicated in direct import of TCA cycle intermediates succinate, fumarate, malate and oxaloacetate. In cluster 8, we additionally find enrichment of pckA converting oxaloacetate to PEP (FIG. 3B).

There are two glyceraldehyde-3-phosphate dehydrogenases in *B. subtilis*: GapA and GapB, mediating the flux of carbon either from glucose to the TCA cycle or vice versa. The glucose and intermediates generated by the gluconeogenetic pathway under conditions of glucose limitation are then used for synthesis of necessary structural constituents. We observe the switch from GapA to GapB expression in clusters 7 and 8 along with an upregulation of most of the TCA cycle enzymes (FIGS. 3A and 3B).

Example 6

Heterogeneous Activation of Myo-Inositol Catabolism Pathway at Intermediate Growth Stages Inositol is an abundant resource in soil, and *B. subtilis* is able to subsist on inositol as its sole carbon source. While LB medium is not typically expected to contain myo-inositol (further "inositol"), heterogeneous inositol utilization pathway activation is observed in a small (3-15% across OD1.7-3.2) subpopulation in both of our independent LB growth experiments (cluster 9, see FIGS. 3A, 3D, 3E). The inositol catabolism intermediate, 2-deoxy-5-keto-D-gluconic acid 6-phosphate (DKGP), is responsible for the pathway induction. We hypothesize that these results arise from trace amounts of inositol present in the LB medium, potentially from the yeast extract since yeast is capable of inositol production as a precursor to the essential membrane component, phosphatidylinositol.

Figure 3D:
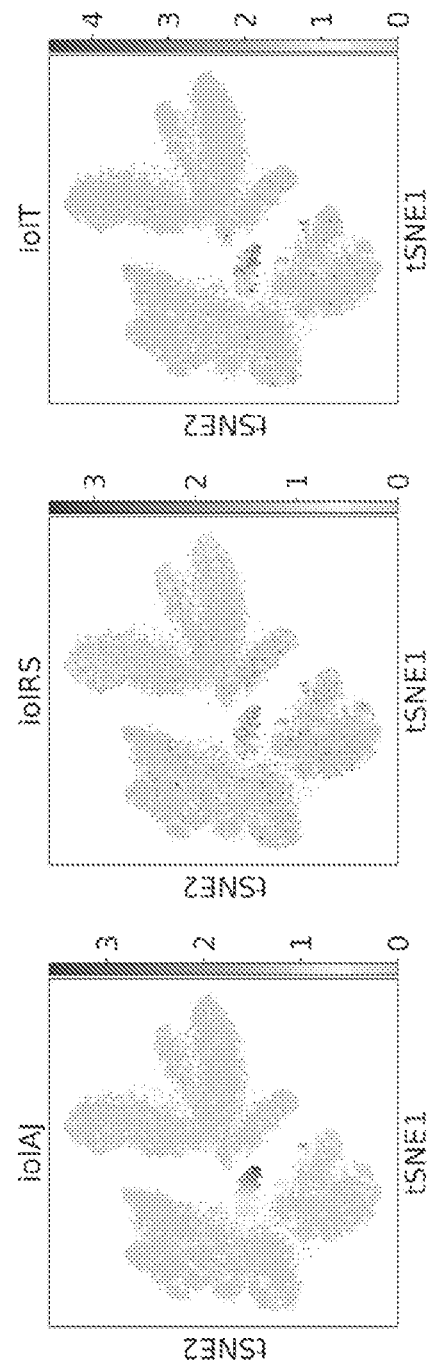
FIG. 3D illustrates expression of each of the three inositol utilization operons, averaged across all genes in a given operon, and overlaid on the t-SNE plot, in accordance with an embodiment of the present disclosure.
Figure 3E:
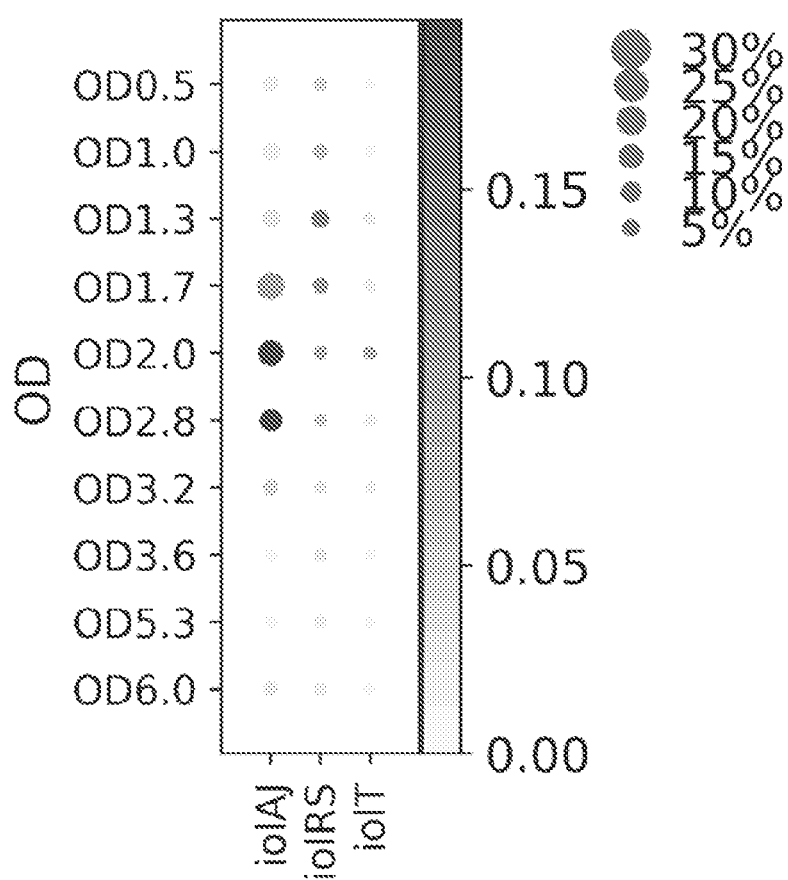
FIG. 3E illustrates activities of the three inositol utilization operons across ODs, in accordance with an embodiment of the present disclosure, where a size of each dot indicates the proportion of cells in each OD sample expressing any of the genes in the selected operon, while the shade shows the average expression of the genes in a given operon.

There are three operons involved in inositol utilization, iolT (main transporter), iolRS (the first gene is a repressor and the second is a likely dehydrogenase), and iolA through J (metabolic enzymes, further "iolAJ"), with IolC producing and IolJ cleaving the pathway-activating DKGP intermediate. iolRS and iolAJ are normally transcribed by $\sigma^A$ through divergent transcription. In the absence of the inducer, IolR suppresses transcription of all three operons. In addition, CcpA represses the iolAJ operon in the presence of glucose. Interestingly, we observe that the pathway suppressor iolR gene is more broadly expressed both outside and inside of cluster 9 (FIGS. 3D and 3E).

Figure 3F:
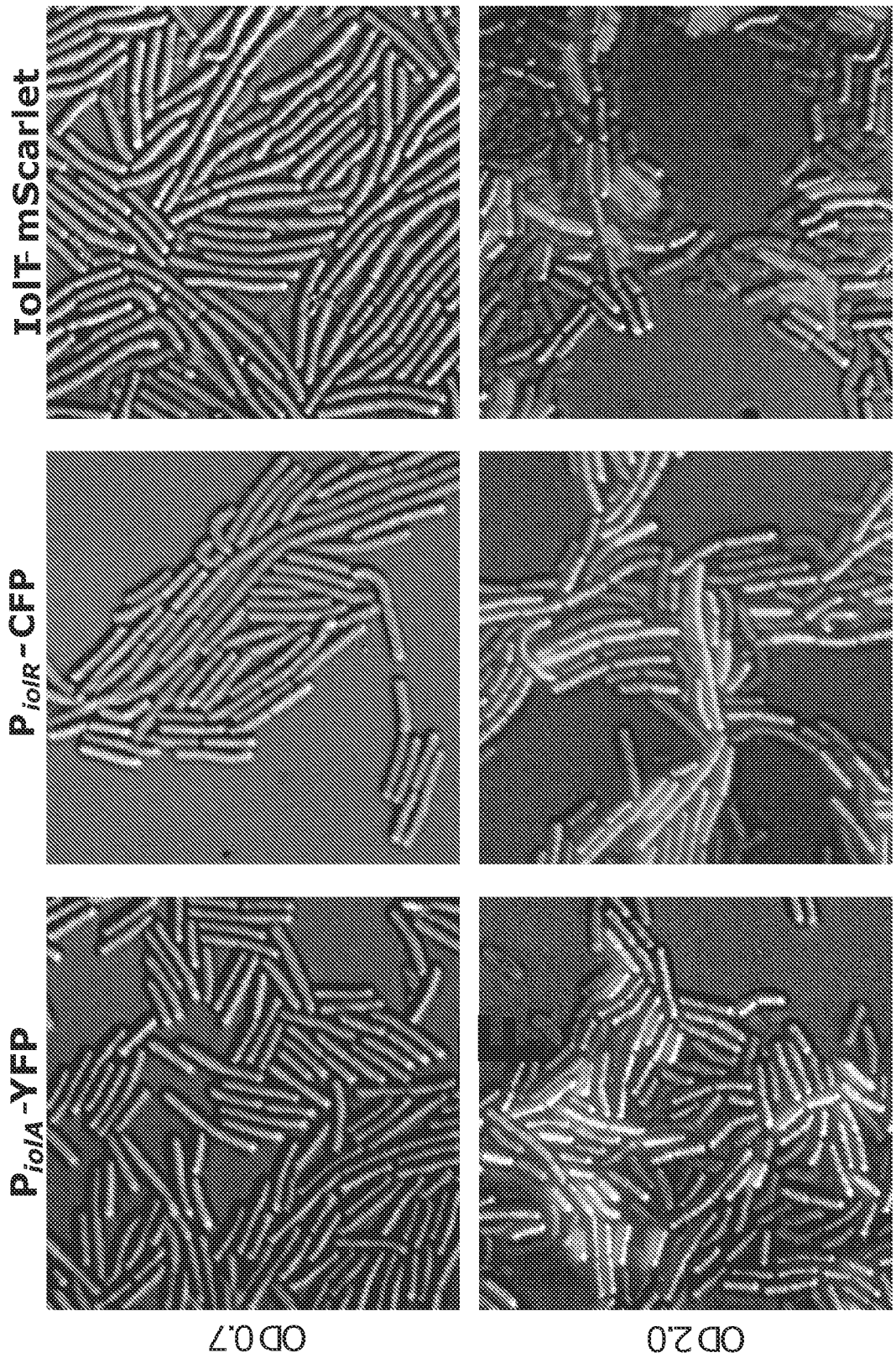
FIG. 3F includes fluorescence and DIC microscopy overlays of B. subtilis expressing PiolA-YFP (left), PiolR-CFP (middle) or IolT-mScarlet-I (right) grown in LB to OD0.7 (top row) or OD2.0 (bottom row), in accordance with an embodiment of the present disclosure.
Figure 3G:
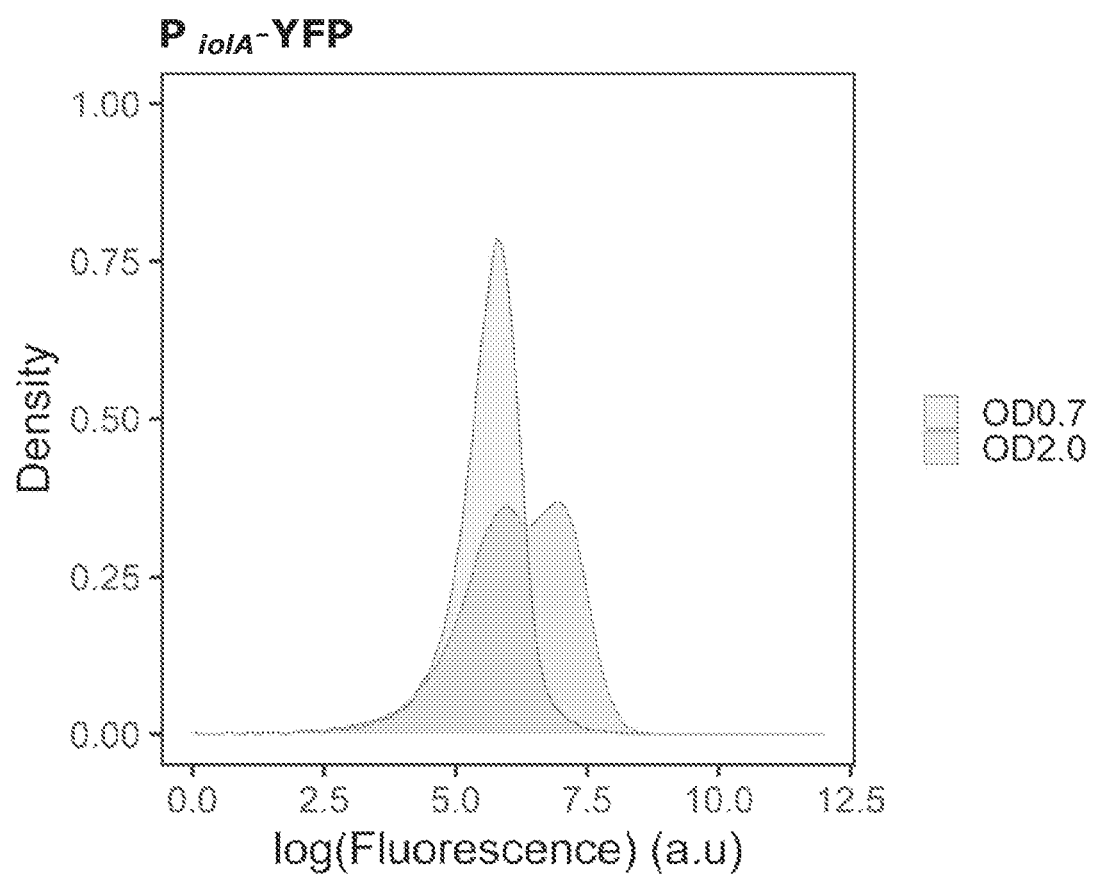
FIG. 3G illustrates flow cytometry of PiolA-YFP strain grown to OD0.7 or 2.0, in accordance with an embodiment of the present disclosure.

To validate our findings, we constructed fluorescent reporters of all three operons in the inositol metabolism pathway (transcriptional reporters $P_{iolA}$-YFP and $P_{iolR}$-CFP and protein fusion IolT-mScarlet-I,). As expected, we observed widespread expression of all three operons in the presence of inositol as a sole carbon source. In agreement with our clustering analysis (FIG. 3E), *B. subtilis* cells grown in LB show heterogeneous expression of $P_{iolA}$-YFP in 22.7% of cells at OD2 and in 44% of cells at OD4, as opposed to cells grown in LB to OD0.7 (threshold set to 1% positive cells in the "off" state OD0.7, FIGS. 3F and 3G). While microSPLiT data shows that the proportion of cells expressing inositol metabolism genes (belonging to cluster 9) drops from 5% at OD3.2 to 0.3% at OD5.3, the accumulation of YFP expressing cells at OD4 is consistent with the delay in fluorescent protein maturation and with the high stability of fluorescent proteins which mainly get cleared from cells by dilution during cell division.

Altogether, our transcriptomics and fluorescent reporter data indicate that the transcription of genes in the inositol metabolism pathway is activated in a heterogeneous fashion in a subpopulation of cells grown in LB between logarithmic and early stationary phases. The source of the activating molecule, as well as the underlying gene regulatory network architecture behind this behavior remain to be determined.

Example 7

Motility, Antimicrobials Production, Stress Response, and Metal Ion Import

Figure 4A:
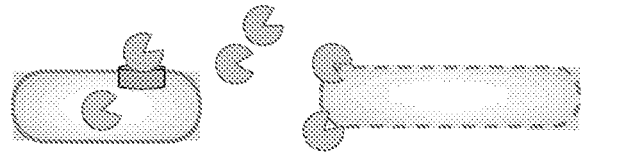
FIG. 4A schematically illustrates a pathway diagram of antimicrobial agents (subtilosin (albA) and bacillaene (pksJ)) and endoA toxin-antitoxin system (top), illustrates overlays of expression of genes representative of each pathway on the t-SNE (middle), and illustrates a fraction of cells expressing at least one of the genes in the indicated operon as a function of OD (bottom), in accordance with an embodiment of the present disclosure.
Figure 4A:
Figure 4A:
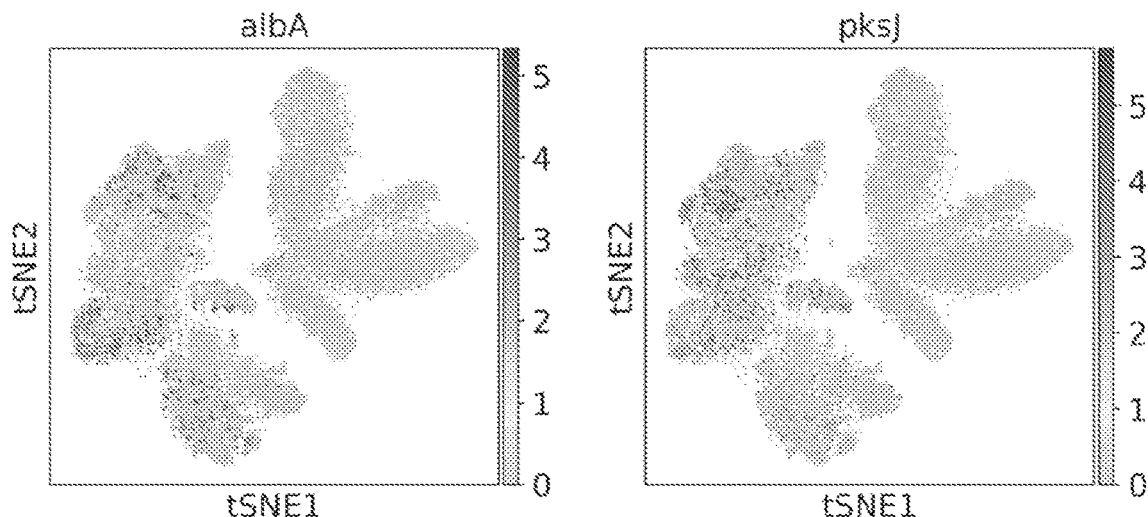
Figure 4A:
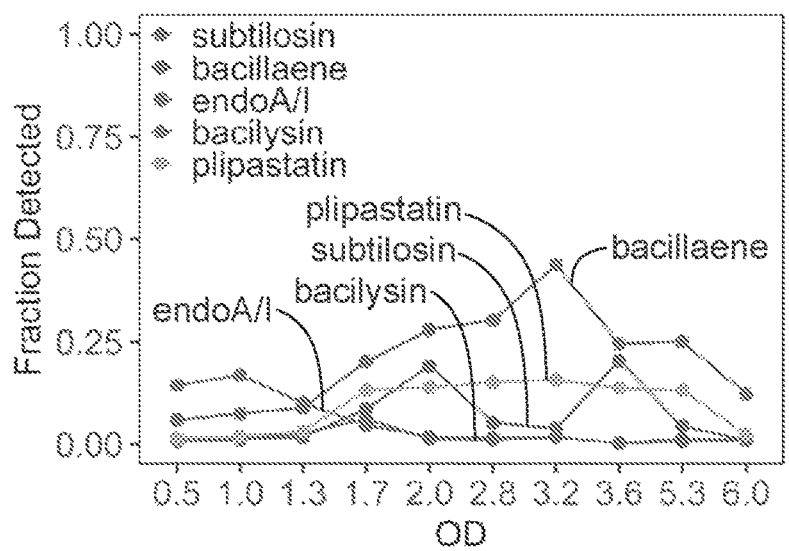

Next, we turned to examine a variety of *B. subtilis* behaviors thought to enhance survival in adverse conditions. Bacteria universally produce peptide and small molecule antimicrobials that are meant to target both closely and distantly related organisms (FIG. 4A). We observe the expression of at least three broad spectrum antimicrobials—subtilosin, bacillaene, and plipastatin—in various fractions of cells across ODs (FIG. 4A). We also see a rise in spore killing factor (SKF) and spore delay protein (SDP) in the last three ODs.

Figure 4B:
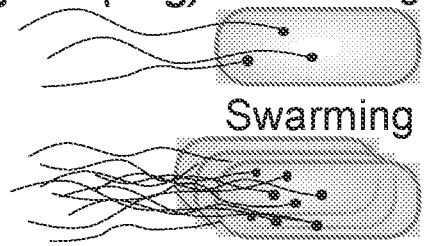
FIG. 4B schematically illustrates a pathway diagram of swarming and motility (surfactin (srfAA) and flagellin (hag)) (top), illustrates overlays of expression of genes representative of each pathway on the t-SNE (middle), and illustrates a fraction of cells expressing at least one of the genes in the indicated operon as a function of OD (bottom), in accordance with an embodiment of the present disclosure.
Figure 4B:
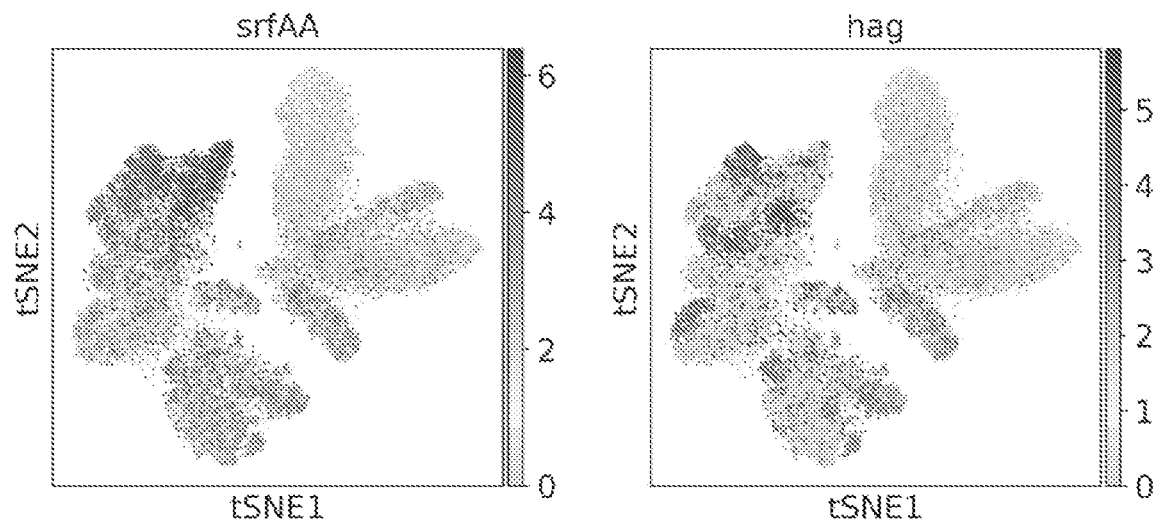
Figure 4B:
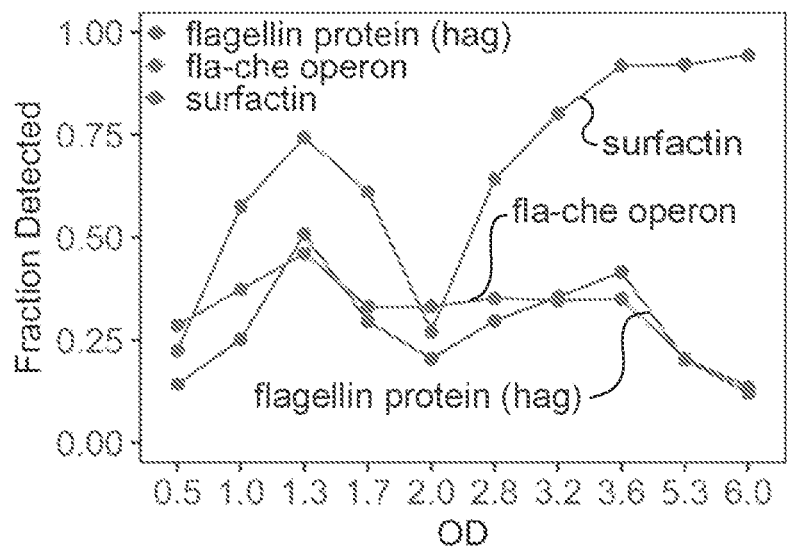

During active growth, *B. subtilis* can morphologically present as filamentous sessile cells or smaller motile cells. Similarly, *B. subtilis* populations are expected to be differentiated into surfactin-producing and extracellular matrix-producing bacteria as cell density increases. We profiled the fraction of cells expressing motility genes (fla-che operon and flagellin encoded by hag), which noticeably declines at OD6.0. Meanwhile, surfactin (srfA-D) reaches almost 100% detection at OD6.0, consistent with the PY79 strain having defective matrix production genes that cannot negatively regulate srfA-D expression (FIG. 4B).

Figure 4C:
FIG. 4C schematically illustrates a pathway diagram of Intrinsic stress and unfolded protein response (UPR) (GroEL chaperonin (groEL) and ClpCP protease (clpC)) (top), illustrates overlays of expression of genes representative of each pathway on the t-SNE (middle), and illustrates a fraction of cells expressing at least one of the genes in the indicated operon as a function of OD (bottom), in accordance with an embodiment of the present disclosure.
Figure 4C:
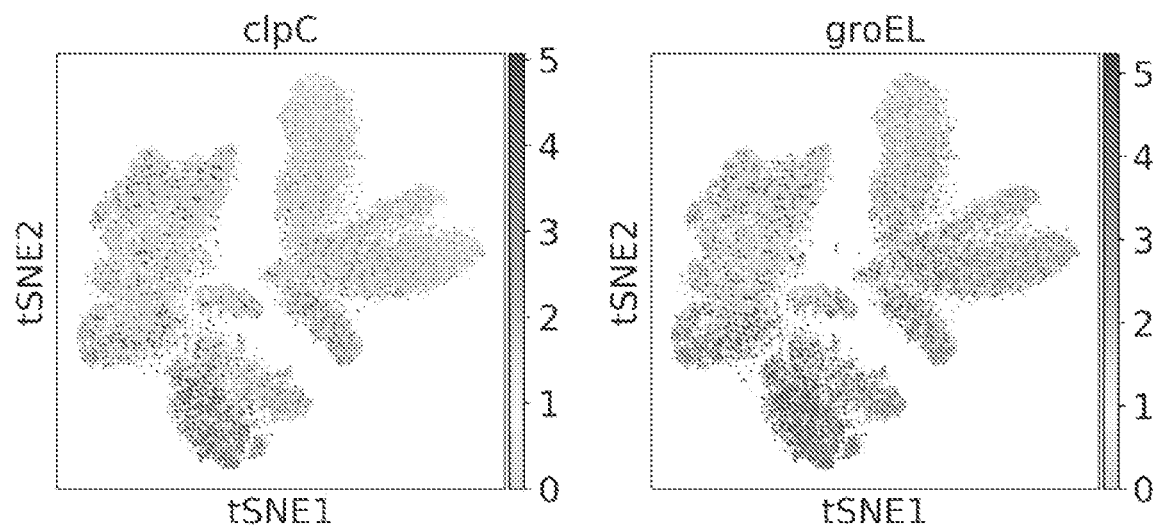
Figure 4C:
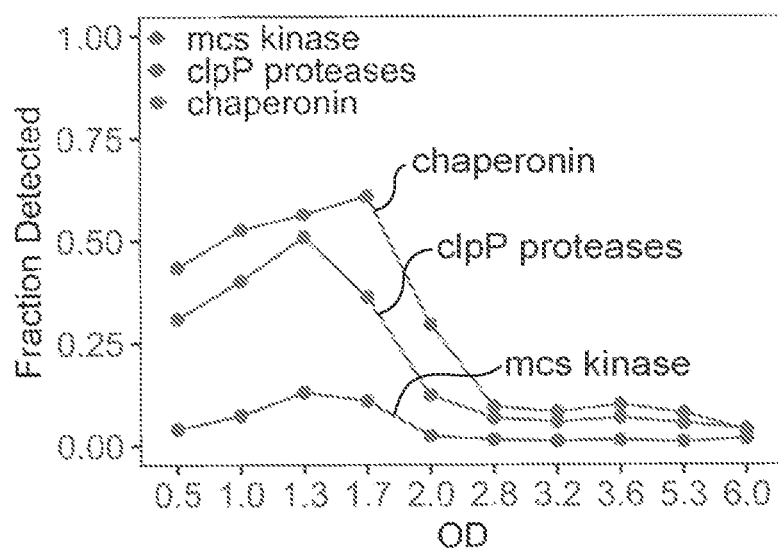
Figure 4D:
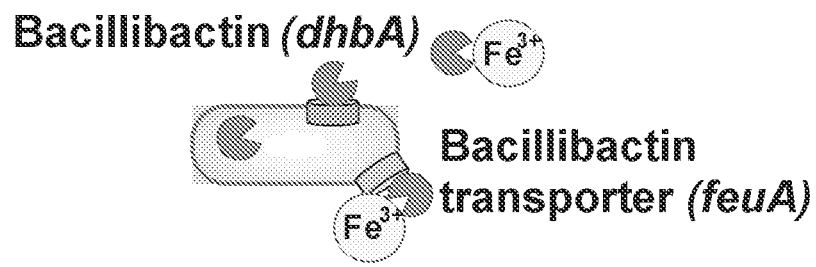
FIG. 4D schematically illustrates a pathway diagram of Iron (bacillibactin (dhbA) and siderophore transporter (feuA)) and manganese uptake (top), illustrates overlays of expression of genes representative of each pathway on the t-SNE (middle), and illustrates a fraction of cells expressing at least one of the genes in the indicated operon as a function of OD (bottom), in accordance with an embodiment of the present disclosure.
Figure 4D:
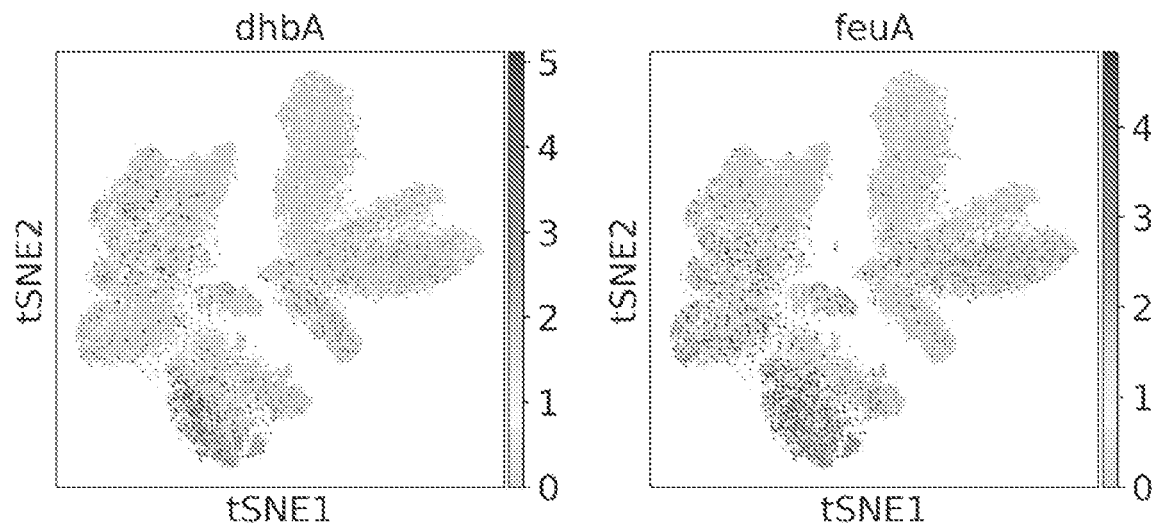
Figure 4D:
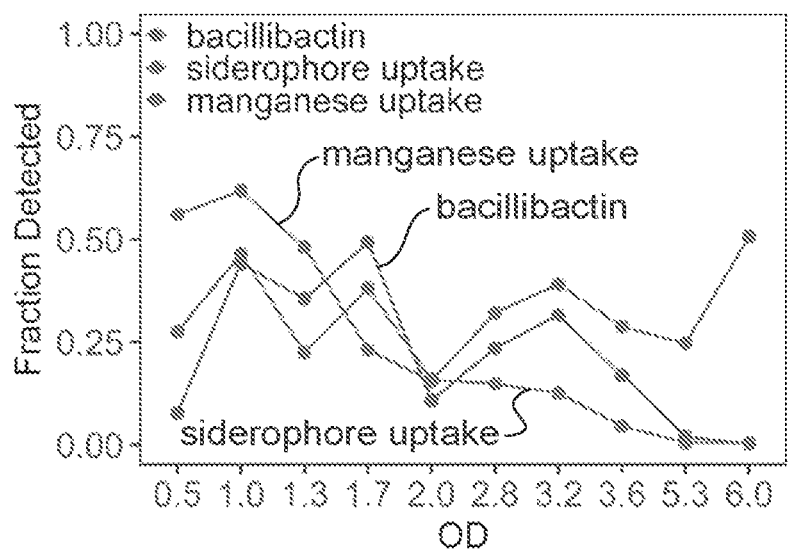

We also found that genes involved in the unfolded protein response such as ClpP associated proteases (clpP,C,X,E), McsA and McsB kinases (mcsA,B), and chaperonins (groEL,ES) peak at OD1.7, the same time as the cells switch from glycolysis to gluconeogenesis (FIG. 4C). A transient increase in the regulatory sigma factor, $\sigma^B$, inducing expression of these genes, occurs during normal exponential growth and attributed to intrinsic cellular stresses (FIG. 2D). Additionally, we profiled expression of genes associated with metal uptake such as siderophore bacillibactin (dhbA) with associated transporter (feuA) and manganese transporter (mntA-D) (FIG. 4D).

Example 8

Microsplit Quantifies a Rare Stress Response

Figure 5A:
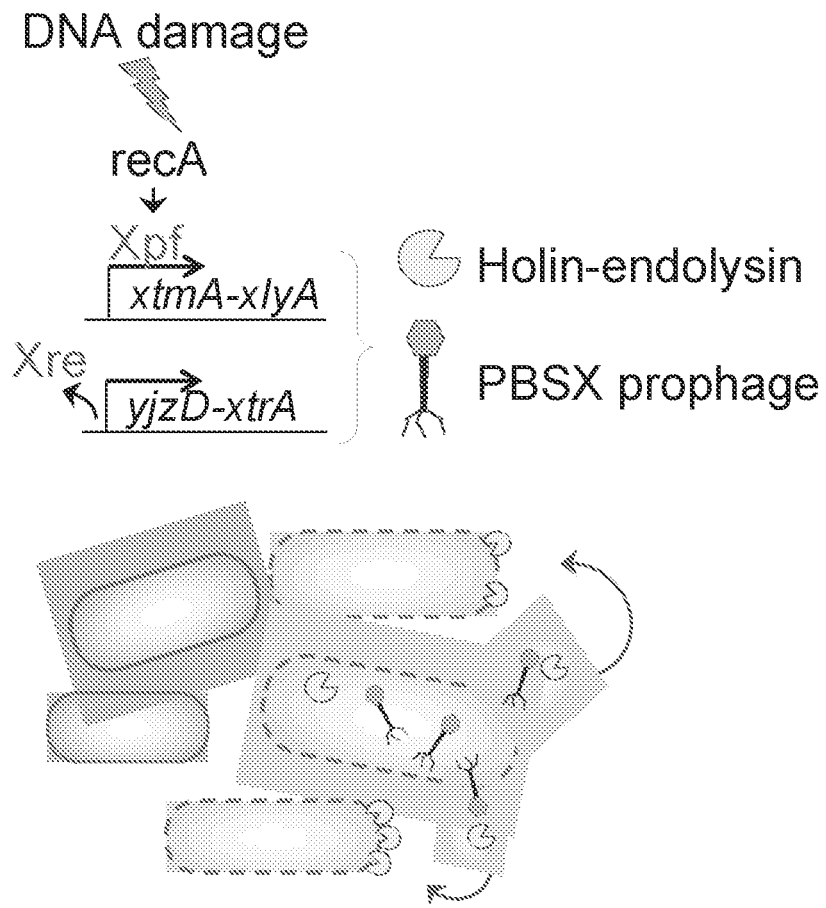
FIG. 5A illustrates an overview of PBSX prophage induction, in accordance with an embodiment of the present disclosure.
Figure 5B:
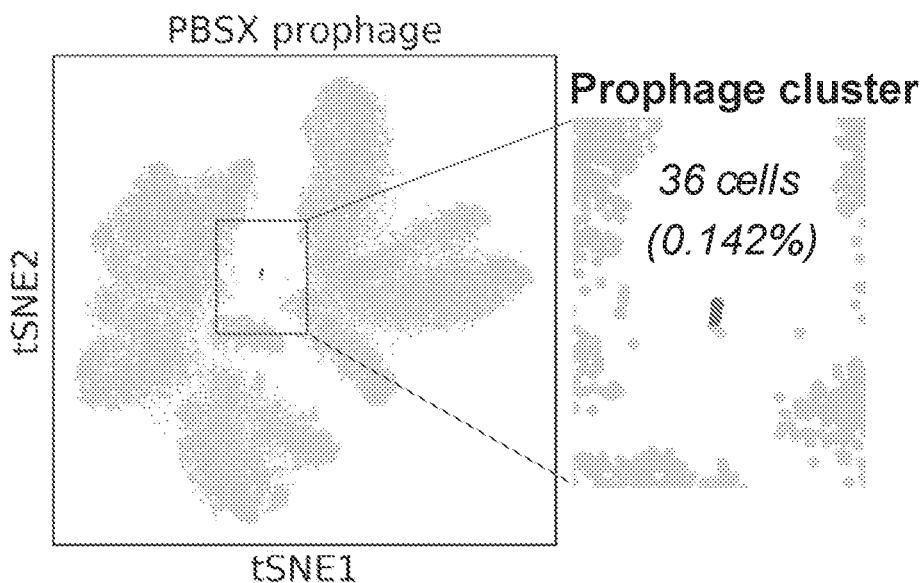
FIG. 5B illustrates PBSX prophage cluster (36 cells) shown on the t-SNE plot, in accordance with an embodiment of the present disclosure.
Figure 5C:
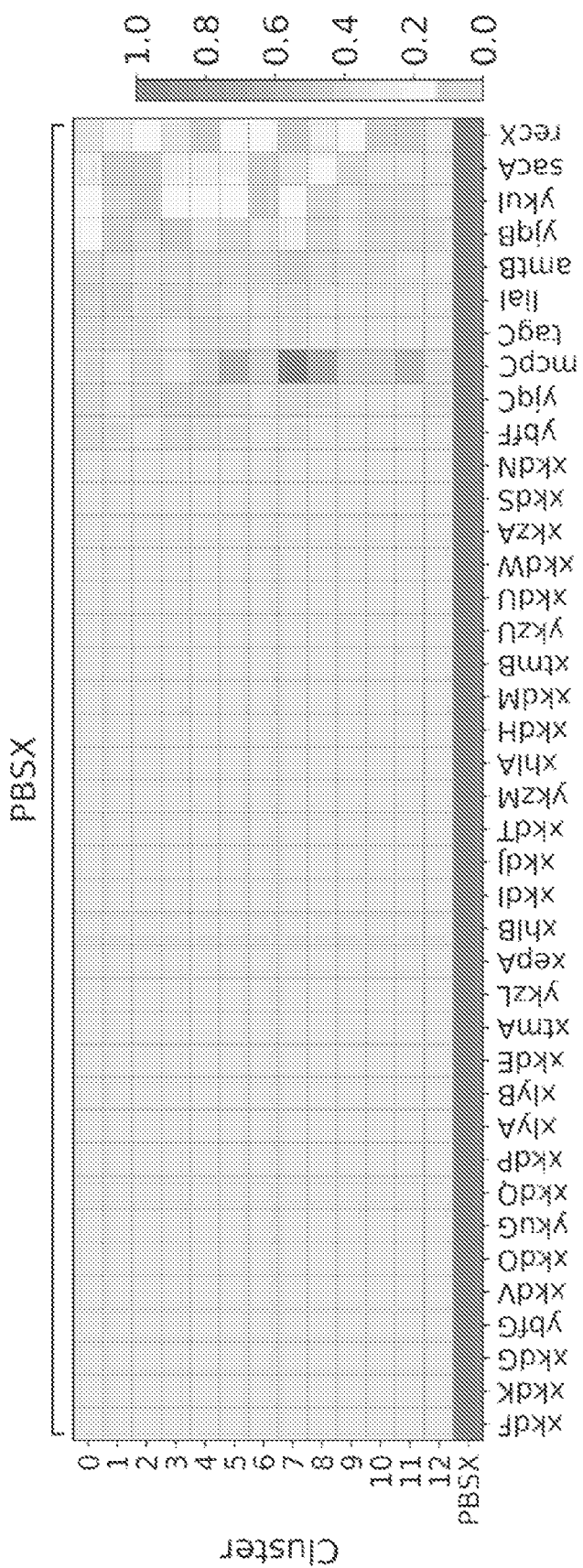
FIG. 5C illustrates a normalized averaged expression of genes enriched in the PBSX prophage cluster, including both prophage and host genes (underscored), in accordance with an embodiment of the present disclosure.

Cluster 13 (36 cells, or 0.142% of total cells, representing ODs between 0.5 and 2.8) contains a rare subpopulation of cells expressing PBSX prophage genes (FIG. 5A). The PBSX element is a defective prophage that is non-infectious but upon induction causes the release of phage-like particles containing 13 kb of random fragmented chromosomal DNA. Prophage gene expression is induced by DNA damage and is known to activate in a small fraction of cells during exponential growth (FIG. 5B). The majority of genes differentially expressed in cluster 13 represent known PBSX prophage genes with functions in PBSX prophage-mediated lysis (xlyA,B, xhlA,B), phage release (xepA), and phage replication (xtmA,B), and many PBSX-associated genes of unknown function (FIG. 5C). Thus, we not only identify a rare subpopulation of cells in the state of prophage induction, but also capture the expression of major phage-associated operons. We also identified eleven host genes with known or putative functions expressed in the PBSX prophage cluster (FIG. 5C). Five of these genes have previously been shown to be induced only in PBSX-harboring strains of *B. subtilis* after DNA damage. The rest, including a chemoreceptor (mcpC), an ATP-binding cassette transporter (liaL), a cell wall binding protein (ykuG), an ammonium transporter (amtB), a sucrose-6-phospate hydrolase (sacA), and a regulatory protein of homologous recombination (recX), have not previously been linked to prophage induction.

Two of the host genes enriched in cluster 13, mcpC and amtB, are linked to the GlnR regulon which responds to excess nitrogen for nitrogen assimilation (FIG. 5C). We also observe increased expression of sacA (FIG. 5C), which is involved in carbohydrate uptake. The other genes identified, liaL, ykuG (syn. fadG), and recX (FIG. 5C), have been shown to be involved in the LiaRS membrane damage response, fatty acid degradation response, and homologous recombination respectively.

In the competence cluster, we observe enrichment of genes related to DNA processing (FIG. 5F) such as topA encoding topoisomerase A and holA, delta subunit of DNA polymerase III which is a part of the replisome. These genes are not in the annotated ComK regulon but have been tentatively identified in the microarray data comparing gene expression between mecA strain, in which essentially all cells express ComK, and a double mutant mecA comK strain. This coordinated upregulation of topA and holA is consistent with RecA binding to the SsbA\SsbB coated ssDNA and forming a complex with the replisome during competence. In addition, we found four genes not previously linked to the competent state: ywfM (unknown), hemQ (coproheme decarboxylase), tlpC (an orphan membrane-bound chemotaxis receptor), and trmF, a folate- and FAD-dependent tRNA methyltransferase (FIG. 5F).

Notably, we detected prior unidentified enrichment of ywfM and hemQ in the competence cluster. ywfM whose product is unknown is located very close but in an opposite orientation to hemQ encoding a coproheme decarboxylase implicated in heme biosynthesis. It was prior hypothesized that ComK could be activating divergent transcription by binding to the palindromic site between yfmK and hemQ, however, yfmK and yfmM were not previously reported to be co-transcribed. In a similar vein, we detected enrichment of nth and tlpC with the latter previously not reported to be ComK-induced. HemQ product, coproheme decarboxylase, functions in heme biosynthesis. Various intermediary metabolism genes are known to be upregulated by ComK but they were not previously known to include the heme biosynthetic pathway. Finally, another gene not hitherto connected to K-state but enriched in the competence cluster is trmF, a folate- and FAD-dependent tRNA methyltransferase involved in tRNA maturation. This finding is in line with another methyltransferase gidB acting on 16S rRNA which has been found enriched in competent cells previously.

Example 9

Microsplit Captures a Rare Stochastically Induced Developmental State

Figure 5D:
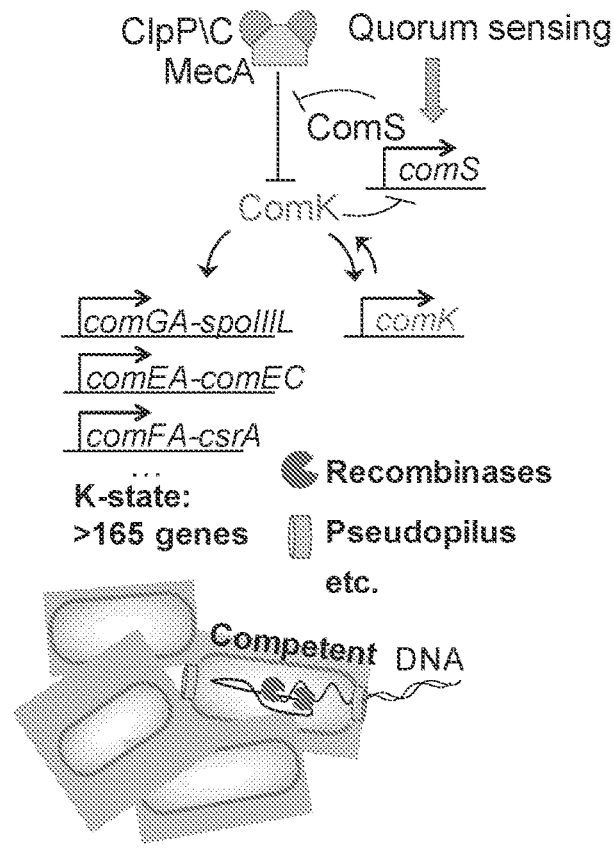
FIG. 5D illustrates an overview of competence development, in accordance with an embodiment of the present disclosure.
Figure 5E:
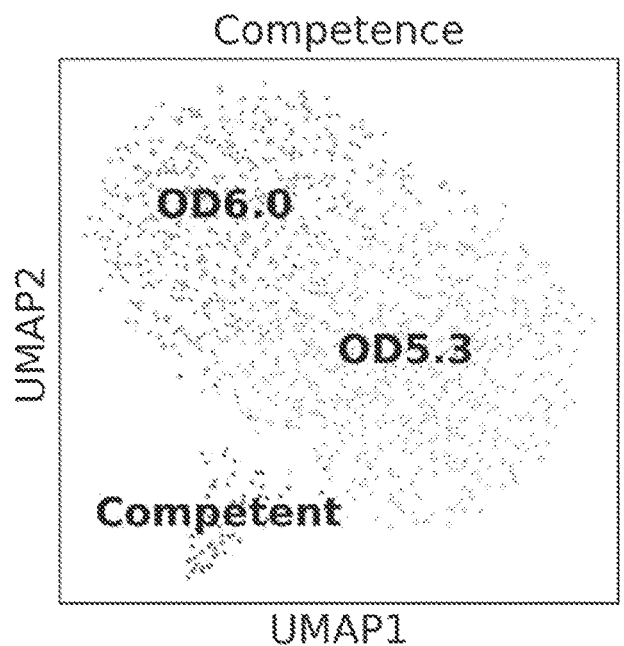
FIG. 5E illustrates UMAP embedding of the subclustered OD5.3 and 6.0 samples, showing the competence cluster (62 cells), in accordance with an embodiment of the present disclosure.
Figure 5F:
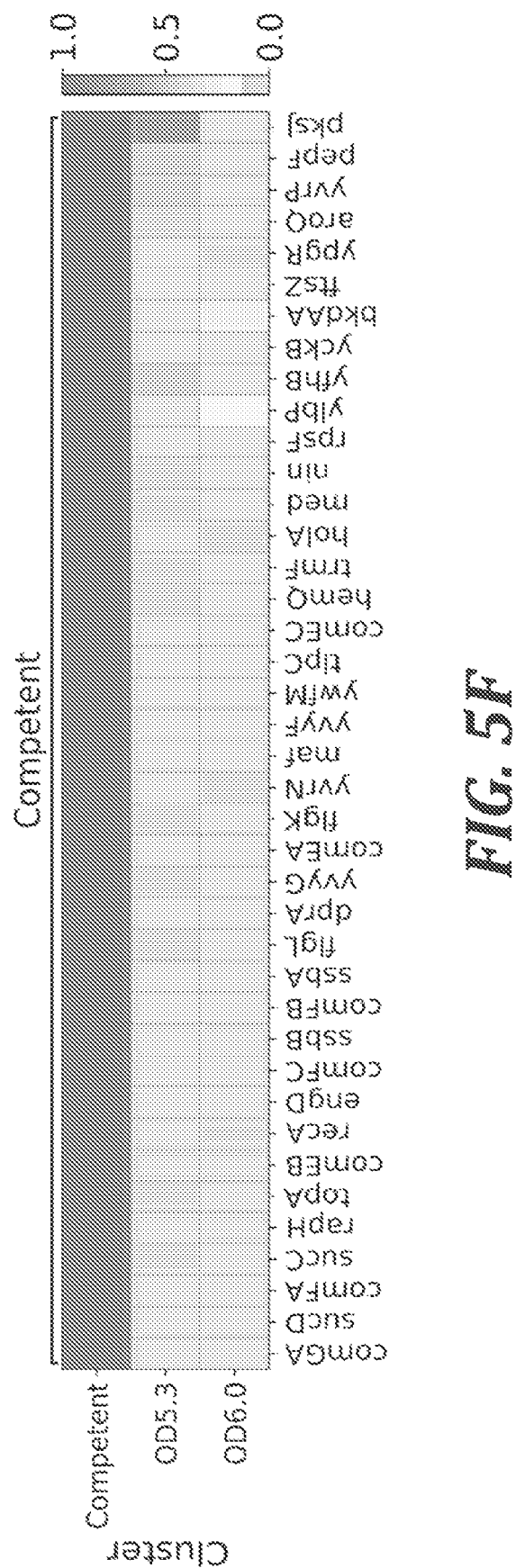
FIG. 5F illustrates a normalized averaged expression of genes enriched in the discovered competence cluster relative to the rest of the cells in OD5.3 and 6.0 samples, in accordance with an embodiment of the present disclosure.

Under stress or nutrient limitation, a small fraction (2-5%) of *B. subtilis* cells undergoes stochastic transient differentiation into a state of natural competence, characterized by the ability to uptake extracellular DNA and integrate it into the chromosome (FIG. 5D). The master transcriptional regulator of competence ComK is activated via a positive feedback loop, inducing expression of a suite of >165 genes involved in a variety of cellular processes in addition to DNA uptake. Competence is expected to naturally occur under nutrient limitation. We thus separately subclustered the last two OD points (OD5.3 and 6.0). UMAP embedding revealed a small cluster (62 cells, or 4.6% of cells at OD 5.3 and 6) expressing a distinct transcriptional signature of the competent state, or K-state (FIGS. 5E and 5F). The observed frequency of competence is comparable to previous reports (3-10%,). The most enriched gene was comGA, as expected from prior transcriptomic data, followed by the succinyl-CoA synthetase (sucCD) operon which is induced in competent cells. We also see enrichment of genes encoding the DNA uptake machinery: comF and comE operons, the response regulator (rapH) which represses sporulation development in competent cells, genes necessary for processing of internalized ssDNA such as recA along with genes for single-strand DNA binding proteins SsbA and SsbB, and other genes related to DNA processing (FIG. 5F). Overall, we capture the majority of genes associated with the state of competence as defined in two previous microarray studies as well as other approaches. In addition, we found four genes not previously linked to the competent state (FIG. 5F).

Discussion

We applied microSPLiT to *B. subtilis* cells growing in liquid rich medium, which is not associated with cellular heterogeneity. Nevertheless, we found a variety of subpopulations displaying differential gene expression of select metabolic, stress response or developmental pathways. In particular, we identified a myo-inositol catabolism pathway, which was activated only in a fraction of cells at later OD points in a distinct temporal fashion. We anticipate microSPLiT to be broadly useful in identifying heterogeneous cell states in more varied environments, such as in multi-species biofilms and natural microbiota.

We were able to detect subpopulations of cells as rare as 0.142% (FIG. 5A), pointing to microSPLiT's potential to uncover physiologically relevant rare cell states, such as persistence, that are hard to study by bulk or low-throughput methods. A conceptually similar method based on combinatorial barcoding for prokaryotic scRNA-seq, published during formal review of this paper, also reported observations of a rare subpopulation of *S. aureus* cells undergoing prophage induction. The regulators for many such states, are not well known and currently reporters or mutants producing the desired state at a higher frequency cannot be engineered. Even for better understood and inducible states, such as prophage induction by UV irradiation, microSPLiT and similar technologies can produce state-specific transcriptional signatures free of artifacts introduced by the perturbation.

In order to use microSPLiT on complex natural communities, the protocol will likely need to be further optimized, particularly the permeabilization and mRNA enrichment steps as cell wall and membrane composition vary among bacteria. However, alternate treatment for different subsamples may still provide optimal results. In addition, we experienced lower mRNA counts from bacteria in stationary phase as opposed to logarithmic growth phase, consistent with their slower growth rate and smaller cell size at this stage. Although the resulting data still reliably identified rare cell states, such as the K-state, further improvement of the protocol should increase sensitivity for applications to slower dividing bacteria or challenging environmental conditions. Finally, it can become desirable to increase cell retention, currently about 25% between the RT step and sub-library preparation, as the method is applied to sparse natural communities rather than lab-grown cultures. Still, we expect microSPLiT to provide an exciting new dimension to studies of bacterial gene expression heterogeneity and community behavior facilitated by the potential scalability to millions of bacterial cells and single-cell resolution without the need for constructing reporters.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method of uniquely labeling nucleic acid molecules within a plurality of microbial cells, the method comprising:
   fixing and permeabilizing the plurality of microbial cells;
   dissociating microbial cell aggregates within a suspension comprising the plurality of microbial cells;
   reverse transcribing mRNA within the plurality of microbial cells to provide cDNA; and
   combinatorially labelling the cDNA to provide labelled cDNA.

2. The method of claim 1, wherein permeabilizing the plurality of microbial cells comprises:
   contacting the plurality of microbial cells with a detergent; and
   contacting the plurality of microbial cells with a cell wall-degradation or a permeabilization enzyme configured to degrade cell walls of the plurality of microbial cells.

3. The method of claim 2, wherein the cell wall-degradation enzyme is lysozyme.

4. The method of claim 2, wherein contacting the plurality of microbial cells with the detergent occurs before contacting the plurality of microbial cells with the cell-wall degradation enzyme.

5. The method of claim 1, further comprising enriching mRNA within the plurality of microbial cells to provide enriched mRNA.

6. The method of claim 5, wherein enriching mRNA within the plurality of microbial cells comprises adenylating the mRNA within the plurality of microbial cells.

7. The method of claim 6, wherein adenylating the mRNA within the plurality of microbial cells comprises:
   contacting the plurality of microbial cells with an adenylating enzyme to provide adenylated mRNA; and
   contacting the adenylated mRNA with a polyT reverse transcription primer.

8. The method of claim 7, wherein reverse transcribing the mRNA comprises reverse transcribing the adenylated mRNA.

9. The method of claim 7, wherein the adenylating enzyme is selected from the group consisting of prokaryotic and eukaryotic poly A polymerases including *E. coli* Poly (A) Polymerase 1 (PAP1).

10. The method of claim 5, wherein enriching mRNA within the plurality of microbial cells comprises selectively enzymatically degrading RNA molecules within the plurality of microbial cells comprising a 5' monophosphate.

11. The method of claim 10, wherein selectively enzymatically degrading RNA molecules within the plurality of microbial cells comprising 5' monophosphate comprises contacting the plurality of microbial cells with a 5' phosphate dependent exonuclease.

12. The method of claim 1, wherein dissociating the microbial cell aggregates comprises agitating the suspension to provide a disaggregated suspension, and wherein dissociating the microbial cell aggregates comprises filtering the disaggregated suspension with one or more filters to provide a filtered, disaggregated suspension.

13. The method of claim 1, wherein dissociating the microbial cell aggregates includes dissociating the microbial cell aggregates before reverse transcribing the mRNA.

14. The method of claim 1, further comprising dissociating microbial cell aggregates in a suspension of the plurality of microbial cells after reverse transcribing the mRNA.

15. The method of claim 1, wherein combinatorially labelling the cDNA comprises:
dividing the plurality of microbial cells into at least two primary aliquots, the at least two primary aliquots comprising a first primary aliquot and a second primary aliquot;
providing primary nucleic acid tags to the at least two primary aliquots, wherein the primary nucleic acid tags provided to the first primary aliquot are different from the primary nucleic acid tags provided to the second primary aliquot;
coupling adapter sequences on the cDNA within each of the at least two primary aliquots with the provided primary nucleic acid tags;
combining the at least two primary aliquots;
dividing the combined primary aliquots into at least two secondary aliquots, the at least two secondary aliquots comprising a first secondary aliquot and a second secondary aliquot;
providing secondary nucleic acid tags to the at least two secondary aliquots, wherein the secondary nucleic acid tags provided to the first secondary aliquot are different from the secondary nucleic acid tags provided to the second secondary aliquot; and
coupling the primary nucleic acid tags within each of the at least two secondary aliquots with the provided secondary nucleic acid tags.

16. The method of claim 15, further comprising:
dissociating microbial cell aggregates in the at least two primary aliquots; and
dissociating microbial cell aggregates in the at least two secondary aliquots.

17. A method of uniquely labeling nucleic acid molecules within a plurality of microbial cells, the method comprising:
fixing and permeabilizing the plurality of microbial cells;
dissociating microbial cell aggregates within a suspension comprising the plurality of microbial cells;
reverse transcribing mRNA within the plurality of microbial cells to provide cDNA; and
combinatorially labelling the cDNA to provide labelled cDNA by:
dividing the plurality of microbial cells into at least two primary aliquots, the at least two primary aliquots comprising a first primary aliquot and a second primary aliquot;
providing primary nucleic acid tags to the at least two primary aliquots, wherein the primary nucleic acid tags provided to the first primary aliquot are different from the primary nucleic acid tags provided to the second primary aliquot;
coupling adapter sequences on the cDNA within each of the at least two primary aliquots with the provided primary nucleic acid tags by enzymatically ligating the adapter sequences to the primary nucleic acid tags within the plurality of microbial cells;
combining the at least two primary aliquots;
dividing the combined primary aliquots into at least two secondary aliquots, the at least two secondary aliquots comprising a first secondary aliquot and a second secondary aliquot;
providing secondary nucleic acid tags to the at least two secondary aliquots, wherein the secondary nucleic acid tags provided to the first secondary aliquot are different from the secondary nucleic acid tags provided to the second secondary aliquot; and
coupling the primary nucleic acid tags within each of the at least two secondary aliquots with the provided secondary nucleic acid tags by enzymatically ligating the primary nucleic acid tags to the secondary nucleic acid tags within the plurality of microbial cells.

* * * * *